(12) United States Patent
de Sauvage et al.

(10) Patent No.: US 6,531,579 B1
(45) Date of Patent: *Mar. 11, 2003

(54) FUSED POLYPEPTIDES

(75) Inventors: Frederic de Sauvage, Foster City, CA (US); Arnon Rosenthal, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/258,000

(22) Filed: Feb. 25, 1999

Related U.S. Application Data
(60) Provisional application No. 60/076,072, filed on Feb. 26, 1998.

(51) Int. Cl.[7] .................................................. C12P 21/02
(52) U.S. Cl. .................... 530/387.3; 530/350; 530/402; 530/413; 536/23.5; 435/69.1; 435/69.7
(58) Field of Search .............................. 530/350, 387.3; 536/23.5

(56) References Cited

U.S. PATENT DOCUMENTS

| 5,602,171 A | 2/1997 | Tang et al. |
| 5,710,173 A | 1/1998 | Tang et al. |

FOREIGN PATENT DOCUMENTS

| WO | WO 96/35124 | 11/1996 |
| WO | WO 96/40276 | 12/1996 |

OTHER PUBLICATIONS

Akimaru et al., "Drosophila CBP is a co–activator of cubitus interruptus in hedgehog signalling" *Nature* 386:735–738 (Apr. 17, 1997).
Alcedo et al., "The Drosophila smoothened Gene Encodes a Seven–Pass Membrane Protein, a Putative Receptor for the Hedgehog Signal" *Cell* 86:221–232 (1996).
Alexandre et al., "Transcriptional activation of hedgehog target genes in Drosophila is mediated directly by the cubitus interruptus protein, a member of the GLI family of zinc finger DNA–binding proteins" *Genes & Development* 10(16):2003–2013 (Aug. 15, 1996).
Apelqvist et al., "Sonic hedgehog directs specialised mesoderm differentiation in the intestine and pancreas" *Current Biology* 7(10):801–804 (Oct. 1, 1997).
Bellusci et al., "Involvement of Sonic hedgehog (Shh) in mouse embryonic lung growth and morphogenesis" *Development* 124(1):53–63 (Jan. 1997).
Bitgood et al., "Hedgehog and Bmp genes are coexpressed at many diverse sites of cell–cell interaction in the mouse embryo" *Developmental Biology* 172(1):126–138 (Nov. 1995).
Bitgood et al., "Sertoli Cell Signaling by Desert Hedgehog Regulates the Male Germline" *Current Biology* 6(3):298–304 (1996).
Busson et al., "Genetic analysis of viable and lethal fused mutants of Drosophila melanogaster" *Roux's Archives of Developmental Biology* 197:221–230 (1988).
Chen and Struhl, "Dual roles for patched in sequestering and transducing Hedgehog" *Cell* 87(3):553–563 (Nov. 1, 1996).
Chiang et al., "Cyclopia and defective axial patterning in mice lacking Sonic hedgehog gene function" *Nature* 383(6599):407–413 (Oct. 3, 1996).
Chidambaram et al., "Mutations in the human homologue of the Drosophila patched gene in Caucasian and African-American nevoid basal cell carcinoma syndrome patients" *Cancer Research* 56(20):4599–4601 (Oct. 15, 1996).
Dominguez et al., "Sending and receiving the hedgehog signal: control by the Drosophila Gli protein Cubitus interruptus" *Science* 272(5268):1621–1625 (Jun. 14, 1996).
Echelard et al., "Sonic hedgehog, a member of a family of putative signaling molecules, is implicated in the regulation of CNS polarity" *Cell* 75:1417–1430 (1993).
Ekker et al., "Patterning activities of vertebrate hedgehog proteins in the developing eye and brain" *Current Biology* 5(8):944–955 (Aug. 1, 1995).
Ericson et al., "Sonic hedgehog induces the differentiation of ventral forebrain neurons: a common signal for ventral patterning within the neural tube" *Cell* 81(5):747–756 (Jun. 2, 1995).
Fan et al., "Patterning of mammalian somites by surface ectoderm and notochord: evidence for sclerotome induction by a hedgehog homolog" *Cell* 79(7):1175–1186 (Dec. 30, 1994).
Gailani et al., "The role of the human homologue of Drosophila patched in sporadic basal cell carcinomas" *Nature Genetics* 14:78–81 (Sep. 1996).
Hahn et al., "Mutations of the Human Homolog of Drosophila Patched in the Nevoid Basal Cell Carcinoma Syndrome" *Cell* 85:841–851 (1996).
Hammerschmidt et al., "Protein kinase A is a common negative regulator of Hedgehog signaling in the vertebrate embryo" *Genes & Development* 10(6):647–658 (Mar. 15, 1996).
Hanks et al., "Protein kinase catalytic domain sequence database: identification of conserved features of primary structure and classification of family members" *Methods in Enzymology* 200:38–62 (1991).
Hooper and Scott, "The Drosophila patched gene encodes a putative membrane protein required for segmental patterning" *Cell* 59:751–765 (1989).

*Primary Examiner*—Yvonne Eyler
*Assistant Examiner*—Eileen B. O'Hara
(74) *Attorney, Agent, or Firm*—Craig G. Svoboda

(57) ABSTRACT

The present invention relates to nucleotide sequences, including expressed sequence tags (ESTs), oligonucleotide probes, polypeptides, vectors and host cells expressing, immunoadhesins, agonists and antagonists to human & vertebrate fused.

19 Claims, 28 Drawing Sheets

OTHER PUBLICATIONS

Hynes et al., "Control of cell pattern in the neural tube by the zinc finger transcription factor and oncogene Gli–1" *Neuron* 19(1):15–26 (Jul. 1997).

Hynes et al., "Induction of Midbrain Dopaminergic Neurons by Sonic Hedgehog" *Neuron* 15:35–44 (1995).

Ingham et al., "Signalling by hedgehog family proteins in Drosophila and vertebrate development" *Curr. Opin. Genet. Dev.* 5:492–498 (1995).

Jiang and Struhl, "Regulation of the Hedgehog and Wingless singalling pathways by the F–box/WD40–repeat protein Slimb" *Nature* 391:493–496 (Jan. 29, 1998).

Johnson et al., "Ectopic expression of Sonic hedgehog alters dorsal–ventral patterning of somites" *Cell* 79:1165–1173 (1994).

Johnson et al., "Human Homolog of Patched, a Candidate Gene for the Basal Cell Nevus Syndrome" *Science* 272:1668–1671 (1996).

Krauss et al., "A functionally conserved homolog of the Drosophila segment polarity gene hh is expressed in tissues with polarizing activity in zebrafish embryos" *Cell* 75:1431–1444 (1993).

Krishnan et al., "Mediation of Sonic hedgehog–induced expression of COUP–TFII by a protein phosphatase" *Science* 278(5345):1947–1950 (Dec. 12, 1997).

Laufer et al., "Sonic hedgehog and Fgf–4 act through a signaling cascade and feedback loop to integrate growth and patterning of the developing limb bud" *Cell* 79(6):993–1003 (Dec. 16, 1994).

Lee et al., "Gli1 is a target of Sonic hedgehog that induces ventral neural tube development" *Development* 124(13):2537–2552 (Jul. 1997).

Li et al., "A single morphogenetic field gives rise to two retina primordia under the influence of the prechordal plate" *Development* 124(3):603–615 (Feb. 1997).

Macdonald et al., "Midline signalling is required for Pax gene regulation and patterning of the eyes" *Development* 121(10):3267–3278 (Oct. 1995).

Marigo et al., "Biochemical evidence that patched is the Hedgehog receptor" *Nature* 384(6605):176–179 (Nov. 14, 1996).

Marti et al., "Requirement of 19K form of Sonic hedgehog for induction of distinct ventral cell types in CNS explants" *Nature* 375(6529):322–325 (May 25, 1995).

Myers (Human sequence tagged site SHGC–32400. GenBank accession No. G27519) (1996).

Nakano et al., "A protein with several possible membrane–spanning domains encoded by the Drosophila segment polarity gene patched" *Nature* 341:508–513 (1989).

Nusslein–Volhard et al., "Mutations Affecting the Pattern of the Larval Cuticle in Drosophila Melanogaster" *Roux's Archives of Developmental Biology* 193(5):267–282 (1984).

Orenic et al., "Cloning and characterization of the segment polarity gene cubitus interruptus Dominant of Drosophila" *Genes & Development* 4(6):1053–1067 (Jun. 1990).

Oro et al., "Basal cell carcinomas in mice overexpressing sonic hedgehog" *Science* 276(5313):817–821 (May 2, 1997).

Perrimon, N., "Hedgehog and Beyond" *Cell* 80:517–520 (1995).

Pham et al., "The Suppressor of fused gene encodes a novel Pest protein involved in Drosophila segment polarity establishment" *Genetics* 140(2):587–598 (Jun. 1995).

Preat et al., "A putative serine/threonine protein kinase encoded by the segment–polarity fused gene of Drosophila" *Nature* 347(6288):87–89 (Sep. 6, 1990).

Preat et al., "Segmental polarity in Drosophial melanogaster: genetic dissection of fused in a Suppressor of fused background reveals interaction with costal–2" *Genetics* 135(4):1047–1062 (Dec. 1993).

Preat, "Characterization of Suppressor of fused, a complete suppressor of the fused segment polarity gene of Drosophila melanogaster" *Genetics* 132(3):725–736 (Nov. 1992).

Riddle et al., "Sonic hedgehog mediates the polarizing activity of the ZPA" *Cell* 75:1401–1416 (1993).

Robbins et al., "Hedgehog elicits signal transduction by means of a large complex containing the kinesin–related protein costal2" *Cell* 90(2):225–234 (Jul. 25, 1997).

Roberts et al., "Sonic hedgehog is an endodermal signal inducing Bmp–4 and Hox genes during induction and regionalization of the chick hindgut" *Development* 121:3163–3174 (1995).

Roelink et al., "Floor plate and motor neuron induction by different concentrations of the amino–terminal cleavage product of sonic hedgehog autoproteolysis" *Cell* 81(3):445–455 (May 5, 1995).

Sisson et al., "Costal2, a novel kinesin–related protein in the Hedgehog signaling pathway" *Cell* 90(2):235–245 (Jul. 25, 1997).

Stone et al., "The tumour–suppressor gene patched encodes a candidate receptor for Sonic hedgehog" *Nature* 384(14):129–134 (Nov. 1996).

Therond et al., "Functional domains of fused, a serine–threonine kinase required for signaling in Drosophila" *Genetics* 142(4):1181–1198 (Apr. 1996).

Therond et al., "Phosphorylation of the fused protein kinase in response to signaling from hedgehog" *Proc. Natl. Acad. Sci. USA* 93(9):4224–4228 (Apr. 30, 1996).

Unden et al., "Mutations in the human homologue of Drosophila patched (PTCH) in basal cell carcinomas and the Gorlin syndrome: different in vivo mechanism of PTCH inactivation" *Cancer Research* 56(20):4562–4565 (Oct. 15, 1996).

Ungar et al., "Inhibition of protein kinase A phenocopies ectopic expression of hedgehog in the CNS of wild–type and cyclops mutant embryos" *Developmental Biology* 178(1):186–191 (Aug. 25, 1996).

van den Heuvel and Ingham, "Smoothened Encodes a Receptor–Like Serpentine Protein Required for Hedgehog Signalling" *Nature* 382:547–551 (1996).

Wicking et al., "Most germ–line mutations in the nevoid basal cell carcinoma syndrome lead to a premature termination of the Patched protein, and no genotype–phenotype correlations are evident" *American Journal of Human Genetics* 60(1):21–26 (Jan. 1997).

Xie et al., "Activating Smoothened mutations in sporadic basal–cell carcinoma" *Nature* 391(6662):90–92 (Jan. 1, 1998).

Zamecnik et al., "Inhibition of replication and expression of human T–cell lymphotropic virus type III in cultured cells by exogenous synthetic oligonucleotides complementary to viral RNA" *Proc. Natl. Acad. Sci.* 83:4143–4146 (1986).

Blanchet–Tournier, M–F, et al., "The Segment–Polarity Gene Fused is Highly Conserved in Drosophila" *Gene* 161:157–162 (1995).

Hammerschmidt, M. et al., "The world According to Hedgehog" *Trends in Genetics* 13(1):14–21 (1997).

> length: 4880 bp (circular)

```
  1 CCCGGGGATC CTCTAGAGAT CCCTCGACCT CGACCCACGC GTCCGCCCAC GGCGTCCGCC ACGCGTCCGG ATGTTGTGGA ACTGTCCCTG
    GGGCCCCTAG GAGATCTCTA GGGAGCTGGA GCTGGGTGCG CAGGCGGGTG CCGCAGGCGG TGCGCAGGCC TACAACACCT TGACAGGGAC

101 GATCTATAGC TCTTCACCGT CTCTACTTTC TTCCTTCTAA GAGATCCTGA AACCTCTGTC ATGGAAAAGT ACCACGTGTT GGAGATGATT GGAGAAGGCT
    CTAGATATCG AGAAGTGGCA GAGATGAAAG AAGGAAGATT CTCTAGGACT TTGGAGACAG TACCTTTTCA TGGTGCACAA CCTCTACTAA CCTCTTCCGA
  1                                                                M  E  K  Y  H  V  L  E  M  I  G  E  G  S

201 CTTTTGGGAG GGTGTACAAG GGTCGAAGAA AATACAGTGC TCAGGTCGTG GCCCTGAAGT TCATCCCAAA ATTGGGGGCG TCAGAGAAGG AGCTGAGGAA
    GAAAACCCTC CCACATGTTC CCAGCTTCTT TTATGTCACG AGTCCAGCAC CGGGACTTCA AGTAGGGTTT TAACCCCGCG AGTCTCTTCC TCGACTCCTT
 15  F  G  R  V  Y  K  G  R  R  K  Y  S  A  Q  V  V  A  L  K  F  I  P  K  L  G  R  S  E  K  E  L  R  N

301 TTTGCAACGA GAGATTGAAA TCTCTAACTT ATTACGCCCC AGACGCCGTA GGGTTGTAAC ACTGTCGAAA CTTTGACTAT TTCTCCACCA CCACCACTGT
    AAACGTTGCT CTCTAACTTT AGAGATTGAA TAATGCGGGG TCTGCGGCAT CCCAACATTG TGACAGCTTT GAAACTGATA AAGAGGTGGT GGTGGTGACA
 48  L  Q  R  E  I  E  I  M  R  G  L  R  H  P  N  I  V  H  M  L  D  S  F  E  T  D  K  E  V  V  V  T

401 GACTATGCTG AGGAGAGCT CTTTCAGATC CTAGAAGATG ACGGAAAACT TCCTGAAGAC CAGGTTCAGG CCATTGCTGC CCAGTTGGTG TCAGCCCTGT
    CTGATACGAC TCCCTCTCGA GAAAGTCTAG GATCTTCTAC TGCCTTTTGA AGGACTTCTG GTCCAAGTCC GGTAACGACG AGTCGGGACA
 81  D  Y  A  E  G  E  L  F  Q  I  L  E  D  D  G  K  L  P  E  D  Q  V  Q  A  I  A  A  Q  L  V  S  A  L  Y

501 ACTATCTGCA TTCCCACCGC ATCCTACACC GAGATATGAA GCCTCAGAAC ATCCTCCTCG CCAAGGGTGG TGGCATCAAG CTCTGTGACT TTGGATTGC
    TGATAGACGT AAGGGTGGCG TAGGATGTGG CTCTATACTT CGGAGTCTTG TAGGAGGAGC GGTTCCCACC ACCGTAGTTC GAGACACTGA AACCTAAACG
115  Y  L  H  S  H  R  I  L  H  R  D  M  K  P  Q  N  I  L  L  A  K  G  G  I  K  L  C  D  F  G  F  A

601 CCGGGCTATG AGCACCAATA CAATGGTGCT GACATCCATC AAAGGCACAC CACTCTATAT GTCTCCAGAG CTGGTGGAGG AGCGACCATA CGACCACACA
    GGCCCGATAC TCGTGGTTAT GTTACCACGA CTGTAGGTAG TTTCCGTGTG GTGAGATATA CAGAGGTCTC GACCACCTCC TCGCTGGTAT GCTGGTGTGT
148  R  A  M  S  T  N  T  M  V  L  T  S  I  K  G  T  P  L  Y  M  S  P  E  L  V  E  E  R  P  Y  D  H  T

701 GCCGGACCTCT GGTCTGTTGG CTGACATACTA TATGAACTGG CAGTAGGCAC CCCTCCCTTC GGGAGGAAG ATACGATGTT CGTAGAAAGT CGACCAGTCG CTCATTCTCA GTAGTAAGAGT
    CGGCCTGGAGA CCAGACAACC GACGATGGAT ATACTTGACC GTCATCCGTG GGGAGGAAG TATGCTACAA ATACGATGTT CGTAGAAAGT CGACCAGTCG GAGTAAGAGT
181  A  D  L  W  S  V  G  C  I  L  Y  E  L  A  V  G  T  P  P  F  Y  A  T  S  I  F  Q  L  V  S  L  I  L  K
```

```
2601 GGGTGACCTT TGACCTCCAG CCCATGGAAT GGATGGCTGC AGCCACACAT GCCTTGTCTG CCCCTGCAGA GGTTCGGTTG ACTCCACCAG GTAGTTGTGG
     CCCACTGGAA ACTGGAGGTC GGTACCTTA CCTACCGACG TCGGTGTGTA CGGAACAGAC GGGGACGTCT CCAAGCCAAC TGAGGTGGTC CATCAACACC
 815  V  T  F   D  L  Q   P  M  E   W  M  A   A  A  T   H  A  L   S  A  P   A  E  V   R  L  T   P  P  G   S  C  G

2701 ATTCTATGAT GGCCTCCTTA TCCTTCTGTT GCAGCTCCTC ACTGAGCAGG GGAAGGCTAG CCTAATCAGG GATATGTCCA GTTCAGAAAT GTGGACCGTT
     TAAGATACTA CCGGAGGAAT AGGAAGACAA CGTCGAGGAG TGACTCGTCC CCTTCCGATC GGATTAGTCC CTATACAGGT CAAGTCTTTA CACCTGGCAA
 848  F  Y  D   G  L  L   I  L  L   L  Q  L   L  T  E   Q  G  K   A  S  L   I  R  D   M  S  S   E  M  W   T  V

2801 TTGTGGCACC GCTTCTCCAT GGTCCTGAGG CTCCCCGAGG AGGCATCTGC ACAGGAAGGG GAGCTTTCGC TATCCAGTCC ACCAAGCCCT GAGCCAGACT
     AACACCGTGG CGAAGAGGTA CCAGGACTCC GAGGGGCTCC TCCGTAGACG TGTCCTTCCC CTCGAAAGCG ATAGGTCAGG TGGTTCGGGA CTCGGTCTGA
 881  L  W  H  R   F  S  M   V  L  R   L  P  E   E  A  S  A   Q  E  G   E  L  S  L   S  S  P   S  P  E   P  D  W

2901 GGACACTGAT TTCTCCCCAG GGCATGGCAG CCCTGCTGAG CCTGGCCATG GCCACCTTTA CCCAGGAGCC CCAGTTATGC CTGAGCTGCC TGTCCCAGCA
     CCTGTGACTA AAGAGGGGTC CCGTACCGTC GGGACGACTC GGACCGGTAC CGGTGGAAAT GGGTCCTCGG GGTCAATACG GACTCGACGG ACAGGGTCGT
 915  T  L  I   S  P  Q   G  M  A  A   L  L  S   L  A  M   A  T  F  T   Q  E  P   Q  L  C   L  S  C  L   S  Q  H

3001 TGGAAGTATC CTCATGTCCA TCCTGAAGCA TCTGCTTGC CCCTTTGCTT CCCAGCTTCC TGGACATGGA TGCTGACCTC CTTATAGTTG CCCTCAGGAC TCAGAAGTTG
     ACCTTCATAG GAGTACAGGT AGGACTTCGT AGACGAACGA GGGAAACGAA GGGTCGAAGG ACCTGTACCT ACGACTGGAG GAATATCAAC AGAACCGGCT AGTCTTCAAC
 948  G  S  I   L  M  S  I   L  K  H   L  L  C   P  S  F   L  N  Q  L   R  Q  A   P  H  G  S   E  F  L   P  V  V

3101 GTGCTCTCTG TCTGCCAGCT CCCTTTGCTT CCCTTTGCGT ATCTTCCGTT GATGCAAGTG CTACGTTCAC ATGCCAGCCA TCAGCCTTCT CACACGCCTG GCCCTCATGG ATCCCACCTC
     CACGAGAGAC AGACGGTCGA GGGAAACGAA GGGAAACGCA TAGAAGGCAA CTACGTTCAC GATGCAAGTG TACGGTCGGT AGTCGGAAGA GTGTGCGGAC CGGGAGTACC TAGGGTGGAG
 981  V  L  S  V   C  Q  L   P  F  A  L   D  M  D   A  D  L   L  I  V   V  L  A  D   L  R  D   S  E  V  A

3201 CAGCCCATCT GCTGCAGGTC TGCTGCTACC ACGACGTCCAG AGTTGCCCA ACCATCTGCT CGTTTCTCTC AGTTGCCCTC GCCCACTGTT GACCTCCGAC
     GTCGGGTAGA CGACGTCCAG CGACGATGTG TGCTGCAGGTC TCAACGGGT TGGTAGACGA GCAAAGAGAG TCAACGGGAG CGGTGACAA CTGGAGGCTG
 1015 A  H  L   Q  V  C   C  Y  H   L  P  L   M  Q  V   E  L  P  I   S  L  L   T  R  L   A  L  M  D   P  T  S

3301 TCTCAACCAG TTTGTGAACA CAGTGTCTGC CTCCCCTAGA ACCATCGTCT CGTTTCTCTC AGTTGCCCTC GCCCACTGTT GACCTCCGAC AGCCACTGTT GACCTCCGAC
     AGAGTTGGTC AAACACTTGT GTCACAGACG GAGGGGATCT TGGTAGCAGA GCAAAGAGAG TCAACGGGAG CAGTCACACTGG TCGGTGACAA CTGGAGGCTG
 1048 L  N  Q   F  V  N  T   V  S  A   S  P  R   T  I  V  S   F  L  S   V  A  L   L  S  D  Q   P  L  L   T  S  D

3401 CTTCTCTCTC TGCTGGCCCA TACTGCCAGG GTCCTGTCTC CCAGCCACTT GTCCTTTATC CAAGAGCTTC TGGCTGGCTC TGATGAATCC TATCGGCCCC
     GAAGAGAGAG ACGACCGGGT ATGACGGTCC CAGGACAGAG GGTCGGTGAA CAGGAAATAG GTTCTCGAAG ACCGACCGAG ACTACTTAGG ATAGCCGGGG
 1081 L  L  S  L   L  A  H   T  A  R   V  L  S  P   S  H  L   S  F  I   Q  E  L  L   A  G  S   D  E  S   Y  R  P  L

FIG._1D
```

```
3501 TGCGCAGCCT CCTGGGCCAC CCAGAGAATT CTGTGCGGGC ACACACTTAT AGGCTCCTGG ACACTTGCT CCAACACAGC ATGGCCCTGC GTGGGCACT
     ACGCGTCGGA GGACCCGGTG GGTCTCTTAA GACACGCCCG TGTGTGAATA TCCGAGGACC CTGTGAACGA GGTTGTGTCG TACCGGGACG CACCCCGTGA
1115 R  S  L    L  G  H     P  E  N  S    V  R  A    H  T  Y  R    L  L  G     H  L  L     Q  H  S     M  A  L  R    G  A  L

3601 GCAGAGCCAG TCTGGACTGC TCAGCCTTCT GCTGCTTGGG CTTGGAGACA AGGATCCTGT TGTGCGGTGC AGTGCCAGCT TTGCTGTGGG CAATGCAGCC
     CGTCTCGGTC AGACCTGACG AGTCGGAAGA CGACGAACCC GAACCTCTGT TCCTAGGACA ACACGCCACG TCACGGTCGA AACGACACCC GTTACGTCGG
1148 Q  S  Q    S  G  L  L    S  L  L     L  L  G     L  E  D  K    D  P  V     V  R  C     S  A  S  F    A  V  G     N  A  A

3701 TACCAGGCTG GTCCTCTGGG ACCTGCCCTG GCAGCTGCAG TGCCCAGTAT GACCCAGCTG CTTGGAGATC CTCAGGCTGG TATCCGGCGC AATGTTGCAT
     ATGGTCCGAC CAGGAGACCC TGGACGGGAC CGTCGACGTC ACGGGTCATA CTGGGTCGAC GAACCTCTAG GAGTCCGACC ATAGGCCGCG TTACAACGTA
1181 Y  Q  A  G    P  L  G     P  A  L     A  A  A  V    P  S  M     T  Q  L     L  G  D  P    Q  A  G     I  R  R     N  V  A  S

3801 CAGCTCTGGG CAACTTGGGA CCTGAAGTTC TGGAGAGGA GCTGTTACAG TGCGAAGTAC CCCAGCGGCT CCTAGAAATG GCATGTGGAG ACCCCCAGCC
     GTCGAGACCC GTTGAACCCT GGACTTCAAG ACCTCTCCT CGACAATGTC ACGCTTCATG GGGTCGCCGA GGATCTTTAC CGTACACCTC TGGGGGTCGG
1215 A  L  G     N  L  G     P  E  G  L    E  E        L  L  Q     C  E  V  P    Q  R  L     L  E  M     A  C  G  D    P  P  Q  P

3901 AAATGTGAAG GAGGCTGCCC TCATTGCCCT CCGGAGCCTG CAACAGGAGC CTGGCATCCA TCAGGTACTG GTGTCCCTGG GTGCCAGTGA GAAACTATCC
     TTTACACTTC CTCCGACGGG AGTAACGGGA GGCCTCGGAC GTTGTCCTCG GACCGTAGGT AGTCCATGAC CACAGGGACC CACGGTCACT CTTTGATAGG
1248 N  V  K    E  A  A  L    I  A  L     R  S  L     Q  Q  E  P    G  I  H     Q  V  L     V  S  L  G    A  S  E     K  L  S

4001 TTGCTCTCTC TGGGAATCA  GTCACTGCCA AACCCTTAGT CACTGCAGGA CACAGCAGTC CCTCCTGAGG AACTCATTCA CCTCCTGAGG CCAGCCCATA
     AACGAGAGAG ACCCCTTAGT CAGTGACGGT TTGGGAATCA GTGACGTCCT GTGTCGTCAG GGAGGACTCC TTGAGTAAGT GGAGGACTCC GGTCGGGTAT
1281 L  L  S  L    G  N  Q     S  L  P     H  S  S  P    R  P  A     S  A  K     H  C  R  K    L  I  H     L  L  R     P  A  H  S
```

FIG._1E

```
4101 GCATGTGATT CCAGATTCCT GCGGTCCAGC CTCCAACTTT GGTGCCAGCT CTTTCTTATN TAATACACAA GCGCCAAYTC AACTGAGAGC TAAAGAGACT
     CGTACACTAA GGTCTAAGGA CGCCAGGTCG GAGGTTGAAA CCACGGTCGA GAAAGAATAN ATTATGTGTT CGCGGTTRAG TTGACTCTCG ATTTCTCTGA
1315 M  O

4201 AGAAAAGAGA TAAGCTGCCA ACTCAACTGA GAACAGAAA CTNGAAGAGA TTTATATATA AAGCTTCTTC CTTCTCCCAG ATGCAGGATG TTTTCAACCA
     TCTTTTCTCT ATTCGACGGT TGAGTTGACT CTTGTCCTTT GANCTTCTCT AAATATATAT TTCGAAGAAG GAAGAGGTC TACGTCCTAC AAAAGTTGGT

4301 GTAAATTTTA TTGCTGTTGG TGCCAGAGAA GAGTCCCTTT TCCAGGGGCC NTTTTCTCCA ATAATGTGCC TTTAACTCTA GGGACCTGCC
     CATTTAAAAT AACGACAACC ACGGTCTCTT CTCAGGGAAA AGGTCCCCGG NAAAAGAGGT TATTACACGG AAATTGAGAT CCCTGGACGG

4401 TCACGGACCT TAGGGAAAAA CCTCAACCTG AGCTCCTTTA ATCTTCCCAG CAGGTTTTTG CCTTAGACGT GCTGGCCCCA
     AGTGCCTGGA ATCCCTTTTT GGAGTTGGAC TCGAGGAAAT TAGAAGGGTC GTCCAAAAAC GGAATCTGCA CGACCGGGT

4501 GGACAGTGAT GAAGACAGAG CCTGTGTCAG CTCTAGGCTG TGCCATCAGT CCCTGTGTATT GAGGGATTAT CCCCTAGCCA ACATTCCTAT
     CCTGTCACTA CTTCTGTCTC GGACAGAGTC GAGATCCGAC ACGGTAGTCA GGGACAATAA CTCCCTAATA GGGAATCGT TGTAAGGATA

4601 CTGTGGGTGG GCGTGGAGAG CGCACCCTC TGTATCTTTT TTTGGGGTGT GTGTGTGTGT ATGTGTGTGT GTTCTGTTTG TAAACTCTTT
     GACACCCACC CGCATGGGAG CGTGGGAG ACATAGAAAA AAACCCCACA TACACATATA CACACACACA CAAGACAAAC ATTGAGAAA

4701 TAATAAAAGT TGTGCCTTCAC CATACTTGAA GCTCCCAGGA CAAGGGTTGA GAGGCTCAAC CCCTCTTTCA GCTTCTATGT GGTGTTGGAG GTGCTGGTAT
     ATTATTTTCA ACACGGAGTG GTATGAACTT CGAGGGTCCT GTTCCCAACT CTCCGAGTTG GGGAGAAAGT CGAAGATACA CCACAACCTC CACGACCATA

4801 CGTGTTCACA CAAAAAAAAAA AAAAAAAAAA AAAAAAAAAA
     GCACAAGTGT GTTTTTTTTT TTTTTTTTTT TTTTTTTTTT
```

FIG._1F

```
CCCGGGCTATGAGCACCAATACAATGGTGCTGACATCCATCAAAGGCACCACTCTATA
TGTCTCCAGAGCTGGTGGAGGAGGACCATACGACCACCACAGCGGACCTCTGGTCTGTTG
GCTGCATACTATATGAACTGGACAGTAGGCACCCTCCCTTCTAATGCTACAAGCATCTTT
CAGCTGGTCAGCC
```

FIG._2 hfused    1  MEKYHVLEMIGEGSFGRVYKGRRKYSAQVVALKFIPKLGRSEKELRNLQR
dfused    1  MDRYAVSSLVGQGSFGCVYKAQRDDDKVVAIKVISKRGRSNRELKNLRR hfused   51  EIEMRGLRHPNIVHMLDSFETDKEVVVTDYAEGELFQILEDDGKLPED
dfused   51  ECDIQARLKHPHVIEMVESFESKFDLFVVTEFALMDLHRYLSFNGAMPEE hfused  101  QVQAIAAQLVSALYYLHSHRILHRDMKPQNILLAKGGGIKLCDFGFARAM
dfused  101  HAQRVVCHLVSALYYLHSNRILHRDLKPQNVLLDKNMHAKLCDFGLARNM hfused  151  STNTMVLTSIKGTPLYMSPELVEERPYDHTADLWSVGCILYELAVGTPPF
dfused  151  TMGTHVLTSIKGTPLYMAPELLAEQPYDHQADMWSLGCIAYESMAGQPPF hfused  201  YATSIFQLVSLILKDPVRWPSTISPCFKNFLQGLLTKDPRQRLSWPDLLY
dfused  201  CATSILHLVKLIKHEDVKWPSTLSSECRSFLQGLLEKDPSMRISWTQLLC

*FIG._3A*

```
hfused  251 HPFIAGHVTI..TEPAGPDLGTPFTSRLPPELQVLKDEQAHRLAPKGNQSR
dfused  251 HPFVEGKL..YIAEVQAAQTSPFINPQLAKDTK..KSQQLRHVGADLGDV.

hfused  301 ILTQAYKRMAEEAMQKKHQNTGPALEQEDKTSKVAPGTAPLPRLGATPQE
dfused  297 LAALKLSDVANENLSTSRDSIN.AIAPSDIEQLETDVEDNVHRL.IVP..

hfused  351 SSLLAGILASELKSSWAKSGTGEVPSAPRENRTTPDC.ERAFPEERPEVL
dfused  343 ...FADISYRELPCG...TAAAARRAGAMPLINSQTCFVSGNSNMILNHL hfused  400 GQRSTDVVDLENEEPDSDNEWQHLLETTEPVPIQLKAPLTLLCNPDFCQR
dfused  387 NDNFAIEAPASSATKSMKSKLKLALNIKQSRSKDLEKRKLSQNLDNFSLR hfused  450 IQSLHEAGGQILKGILEGASHILPAFRVLSSLLSSCSDSVALYSFCREA
dfused  437 LGQSIDIEVQRKTTEMLTQQQAQQLQDRKTQQLKQSMHSTNDEKLSSDN
```

*FIG._3B*

```
hfused  500  GLPGLLSLLR-HSQESNSLQQQSWYGTFLQDLMAVIQAYFACTFNLE-R
dfused  487  SPPCLLPGWDSCDESQSPPIENDEWLAFLHRSIQELLDGEFDSLKQHNLV hfused  548  SQTSDSLQVFQEAANLFLDLLGKLLAQPDDSEQTLQRDSLMCFTVLCEAM
dfused  537  SIIVAPLRNSKAIPKV-LQSVAQLLSLP----FVLAEQHLVAEAI--KGV hfused  598  DGNSRAISKAFYSSLLTTQQVVLDGLLHGLTVPQLPVHTPQGAPQVSQPL
dfused  580  YIDVKLVPNLMYACKLLLSQRHLTD-----SAASLPAGTGVSLSRTVRSC hfused  648  REQSEDIPGAISSALAAICTAPVGLPDCWDAKEQVCWHLAN-QLTEDSSQ
dfused  625  SDLSAEEMSTACSLYELVCHLVHQQQQFL---TQFCDAVAILAVNDMFIN hfused  697  LRPSLISGLQHPILCLHLLKVLYSCCLVSE--GLCRLLGQEPLALE-SLF
dfused  672  FLTHDFKDSRPVRLASCMLF-ALF-CCVLRELPENAELVEKIVFDSRLQLA
```

FIG._3C

```
hfused  744  MLIQGKVKVVDWEESTEVTLYFLSLLVFRLQNLPCG-MEKLGSDVATLFT
dfused  720  VLLQSRHHLL-RQRACQM...LLLARFSLRGVQCIWSGELKSALQAWPM hfused  793  HSHVVSLVSAAACLGQLGQGVTFDLQPMEWMAAATHALSAPAEVRLTP
dfused  766  QQTCQSLREAAQTLDELSQFSF-FVAQATA hfused  843  PGSCGFYDGLLILLLQLLTEQGKASLIRDMSSSEMWTVLWHRFSMVLRLP hfused  893  EEASAQEGELSLSSPPSPEPDWTLISPQGMAALLSLAMATFTQEPQLCLS hfused  943  CLSQHGSILMSILKHLLCPSFLNQLRQAPHGSEFLPVVVLSVCQLLCFPF hfused  993  ALDMDADLLIVVLADLRDSEVAAHLLQVCCYHLPLMQVELPISLLTRLAL
```

*FIG._3D*

```
hfused  1043  MDPTSLNQFVNTVSASPRTIVSFLSVALLSDQPLLTSDLLSLLAHTARVL hfused  1093  SPSHLSFIQELLAGSDESYRPLRSLLGHPENSVRAHTYRLLGHLLQHSMA hfused  1143  LRGALQSQSGLLSLLLLGLGDKDPVVRCSASFAVGNAAYQAGPLGPALAA hfused  1193  AVPSMTQLLGDPQAGIRRNVASALGNLGPEGLGEELLQCEVPQRLLEMAC hfused  1243  GDPQPNVKEAALIALRSLQQEPGIHQVLVSLGASEKLSLLGNQSLPHS hfused  1293  SPRPASAKHCRKLIHLLRPAHSM
```

FIG._3E

```
> length: 5125 bp (circular)

1 CCCACGCGTC CGCCCACGCG TCCGGGGCGT CCCAGATGTT GTGGAACTGT CCCTGGATCT ATAGCTCTTC ACCGTCTCTA CTTTCTTCCT TCTAAGAGAT
     GGGTGCGCAG GCGGGTGCGC AGGCCCCGCA GGGTCTACAA CACCTTGACA TATCGAGAAG TGGCAGAGAT GAAAGAAGGA AGATTCTCTA

101 CCTGAAACCT CTGTCATGGA AAAGTACCAC GTGTTGGAGA TGATTGGAGA AGGCTCTTTT GGGAGGGTGT ACAAGGGTCG AAGAAAATAC AGTGCTCAGG
     GGACTTTGGA GACAGTACCT TTTCATGGTG CACAACCTCT ACTAACCTCT TCCGAGAAAA CCCTCCCACA TGTTCCCAGC TTCTTTTATG TCACGAGTCC
   1              M  E  K  Y  H  V  L  E  M  I  G  E  G  S  F  G  R  V  Y  K  G  R  R  K  Y  S  A  Q  V
                  ^Start of 1st ORF!

201 TCGTGGCCCT GAAGTTCATC CCAAAATTGG GGCGCTCAGA GAAGGAGCTG AACGAGAGAT TGAAATAAATG CGGGGTCTCGC GGCATCCCAA
     AGCACCGGGA CTTCAAGTAG GGTTTTAACC CCGCGAGTCT CTTCCTCGAC TTGCTCTCTA ACTTTATTAC GCCCCAGACG CCGTAGGGTT
  30  V  A  L  K  F  I  P  K  L  G  R  S  E  K  E  L  R  N  L  Q  R  E  I  E  I  M  R  G  L  R  H  P  N

301 CATTGTGCAT ATGCTTGACA GCTTTGAAAC TGATAAAGAG TGCTGAGGGA TGACAGACTA TGCTGAGGGA GAGCTCTTTC AGATCCTAGA AGATGACGGA
     GTAACACGTA TACGAACTGT CGAAACTTTG ACTATTTCTC ACGACTCCCT ACTGTCTGAT ACGACTCCCT CTCGAGAAAG TCTAGGATCT TCTACTGCCT
  63  I  V  H  M  L  D  S  F  E  T  D  K  E  V  V  V  V  T  D  Y  A  E  G  E  L  F  Q  I  L  E  D  D  G

401 AAACTTCCTG AAGACCAGGT TCAGGCCATT GCTGCCCAGT TGGTGTCAGC CCTGTACTAT CTGCATTCCC ACCGCATCCT ACACCGAGAT ATGAAGCCTC
     TTTGAAGGAC TTCTGGTCCA AGTCCGGTAA CGACGGGTCA ACCACAGTCG GGACATGATA GACGTAAGGG TGGCGTAGGA TGTGGCTCTA TACTTCGGAG
  96  K  L  P  E  D  Q  V  Q  A  I  A  A  Q  L  V  S  A  L  Y  Y  L  H  S  H  R  I  L  H  R  D  M  K  P  Q

501 AGAACATCCT CCTCGCCAAG GGTGGTGGCA TCAAGCTCTG AGTTCGAGAC ACTGAAACCT TTTGCCCGGG CTATGAGCAC CAATACAATG GTGCTGACAT CCATCAAAGG
     TCTTGTAGGA GGAGCGGTTC CCACCACCGT AGTTCGAGAC TCAAGCTCTG TGACTTTGGA AAACGGGCCC GATACTCGTG GTTATGTTAC CACGACTGTA GGTAGTTTCC
 130  N  I  L  L  A  K  G  G  G  I  K  L  C  D  F  G  F  A  R  A  M  S  T  N  T  M  V  L  T  S  I  K  G

601 CACACCACTC TATATGTCTC CAGAGCTGGT GGAGGAGGA CCTCCCTCGCT GGTATGCTGG TGTGTCGCCT GGAGACCAGA CCTCTGGTCT GTTGGCTGCA CAACCGACGT TACTATATGA ACTGGCAGTA
     GTGTGGTGAG ATATACAGAG GTCTCGACCA CCTCCTCCT CCAGGGAGCGA CCATACGACC ACACAGCGGA CCTCTGGTCT GGAGACCAGA CAACCGACGT GTTGGCTGCA ATGATATACT TGACCGTCAT
 163  T  P  L  Y  M  S  P  E  L  V  E  E  R  P  Y  D  H  T  A  D  L  W  S  V  G  C  I  L  Y  E  L  A  V
```

FIG.—4A

```
701  GGCACCCCTC CCTTCTATGC TACAAGCATC TTTCAGCTGG TCAGCCTCAT TCTCAAGGAC CCTGTGCGCT GGCCCTCAAC CATCAGTCCC TGCTTTAAGA
     CCGTGGGGAG GGAAGATACG ATGTTCGTAG AAAGTCGACC AGTCGGAGTA AGAGTTCCTG GGACACGCGA CCGGGAGTTG GTAGTCAGGG ACGAAATTCT
196   G  T  P  P   F  Y  A   T  S  I   F  Q  L  V   S  L  I   L  K  D   P  V  R  W   P  S  T   I  S  P   C  F  K  N

801  ACTTCCTGCA GGGACTGCTC ACCAAAGACC CACGGGCAGCG ACTGTCCTGG CCAGACCTCT TATATCACCC CTTTATTGCT GGTCATGTCA CCATAATAAC
     TGAAGGACGT CCCTGACGAG TGGTTTCTGG GTGCCCGTCGC TGACAGGACC GGTCTGGAGA ATATAGTGGG GAAATAACGA CCAGTACAGT GGTATTATTG
230   F  L  Q  G   L  L  L   T  K  D   P  R  Q  R   L  S  W   P  D  L  L   Y  H  P   F  I  A   G  H  V  T   I  I  T

901  TGAGCCAGCA GGCCCAGATT TGGGGACCCC ATTCACCAGC CGCCTACCCC CAGAACTTCA GGTCCTAAAG GACGAACAGG CCCATCGGTT GGCCCCCAAG
     ACTCGGTCGT CCGGGTCTAA ACCCCTGGGG TAAGTGGTCG GCGGATGGGG GTCTTGAAGT CCAGGATTTC CTGCTTGTCC GGGTAGCCAA CCGGGGGTTC
263   E  P  A   G  P  D  L   G  T  P   F  T  S   R  L  P  P  P   E  L  Q   V  L  K   D  E  Q  A   H  R  L   A  P  K

1001 GGTAATCAGT CTCGCATCTT GACTCAGGCC TATAAACGCA TGGCTGAGGA AGCCATGCAG AAGAAACATC AGAACACAGG ACCTGCCCTT GAGCAAGAGG
     CCATTAGTCA GAGCGTAGAA CTGAGTCCGG ATATTTGCGT ACCGACTCCT TCGGTACGTC TTCTTTGTAG TCTTGTGTCC TGGACGGGAA CTCGTTCTCC
296   G  N  Q  S   R  I  L   T  Q  A   Y  K  R  M   A  E  E   A  M  Q   K  K  H  Q   N  T  G   P  A  L   E  Q  E  D

1101 ACAAGACCAG CAAGGTGGCT CCCCTCTGCC CAGAGCTCGG GCCACTCCTC AGGAATCAAG CCTCCTGGCC GGGATCTTAG CCTCAGAATT
     TGTTCTGGTC GTTCCACCGA GGGGAGACGG GTCGAGCCC CGGTGAGGAG TCCTTAGTTC GGAGGACCGG CCCTAGAATC GGAGTCTTAA
330   K  T  S   K  V  A   P  G  T  A   P  L  P   R  L  G   A  T  P  Q   E  S  S   L  L  A   G  I  L  A   S  E  L

1201 GAAGAGCAGC TGGGCTAAAT CAGGGACTGG AGAGGTGCCC TCTGCACCTC GATTGTGAAC GACCACCCCA AGTGACAATG AGTGGCAGCA CCTGCTAGAG AGAGGAGAGG
     CTTCTCGTCG ACCCGATTTA GTCCCTGACC TCTCCACGGG AGACGTGGAG CTAACACTTG CTGGTGGGGT TCACTGTTAC TCACCGTCGT GGACGATCTC TCTCCTCTCC
363   K  S  S   W  A  K  S   G  T  G   E  V  P   S  A  P  R   E  N  R   T  T  P   D  C  E  R   A  F  P   E  E  R

1301 CCAGAGGTGC TGGCCAGCG ACCCGGTCGC CTCGTGACTA CATCCAGAG GCATCCAGAG TTCTGCCAGC GCATCCAGAG TCAGCTGCAT GAAGCTGGAG GGCAGATCCT
     GGTCTCCACG ACCGGTCGC TGGGCCAGCG GTAGCAGTGAT GTAGGTCTC CGTAGGTCG AAGACGGTG GCGTAGGTCG CGTAGGTCTC AGTCGACCTC CCGTCTAGGA
396   P  E  V  L   G  Q  R   S  T  D   V  V  D  L   E  N  E   E  P  D   S  D  N  E   W  Q  H   L  L  E   T  T  E  P

1401 CTGTGCCTAT TCAACTGAAG AGTTGACTTC CGAGAGAGT GAACGACAC ATTAGGACTG TTCTGCCAGC AAGACGGTG CGTAGGTC CGGAGAGTCTC CCGTCTAGGA
     GACACGGATA AGTTGACTTC CGAGAGAGT GAACGACAC ATTAGGACTG TTCTGCCAGC AAGACGGTG CGTAGGTC CGGAGAGTCTC CCGTCTAGGA
430   V  P  I   Q  L  K   A  P  L  T   L  L  C   N  P  D   F  C  Q  R   I  Q  S   Q  L  H   E  A  G  G   Q  I  L

1501 GAAAGGCATC TTGGAGGGTG CTTCCCACAT CCTGCCTGCA TTCCCGGGTCC TGAGCAGTCT TCTCTCCAGC AAGGCCCAGG ACTCGTCAGA AGAGAGGTCG AGTCACTAA GACAACGGAA CATAAGGAAG
     CTTTCCGTAG AACCTCCCAC GAAGGGTGTA GGACGGACGT AAGGGCCCAG GACTCGTCGA AGAGAGTCT TCTCGGGTCC TGCCGGGTCC CCGTGGTTAC GCTGTTGCCTT GTATTCCTTC
463   K  G  I   L  E  G  A   S  H  I   L  P  A   F  R  V  L   S  S  L   L  S  S   C  S  D  S   V  A  L   Y  S  F
```

FIG._4B

```
1601 TGCCGGGAGG CAGGGCTTCC TGGGCTGCTG CTGAGTCTAC TCAGGCACAG AACAGCCTCC AGCAGCAATC TTGGTATGGG ACCTTCTTAC
     ACGGCCCTCC GTCCGAAGG  ACCCGACGAC GACTCAGATG AGTCCGTGTC AGTCCTCTCG TTGTCGGAGG TCGTCGTTAG AACCATACCC TGGAAGAATG
 496  C  R  E  A  G  L  P   G  L  L   L  S  L  L   R  H  S    Q  E  S  N   S  L  Q  Q   Q  S  W  Y   G  T  F  L  Q

1701 AGGACCTGAT GGCTGTGATT CAGGCCTACT TTGCCTGTAC CTTCAATCTG GAGAGGAGCC AGACAAGTGA CAGCCTGCAG GTGTTTCAGG AGGCTGCCAA
     TCCTGGACTA CCGACACTAA GTCCGGATGA AACGGACATG GAAGTTAGAC CTCTCCTCGG TCTGTTCACT GTCGGACGTC CACAAAGTCC TCCGACGGTT
 530  D  L  M  A  V  I   Q  A  Y  F   A  C  T    F  N  L  E   R  S  Q   T  S  D   S  L  Q   V  F  Q  E    A  A  N

1801 CCTTTTTCTG GACCTGTTGG GGAAACTGCT GGCCCAACCA GATGACTCTG AGCAGACTTT GCAGAGGGAC AGCCTTATGT GCTTTACTGT CCTGTGCGAA
     GGAAAAAGAC CTGGACAACC CCTTTGACGA CCGGGTTGGT CTACTGAGAC TCGTCTGAAA CGTCTCCCTG TCGGAATACA CGAAATGACA GGACACGCTT
 563  L  F  L  D  L  L  G   K  L  L   A  Q  P    D  D  S  E   Q  T  L   Q  R  D   S  L  M  C    F  T  V    L  C  E

1901 GCCATGGATG GGAACAGCCG GGCCATCTCC AAAGCCTTTT ACTCCAGCTT GCTGACGACA CAGCAGGTTG TCTTGGATGG GCTCCTTCAT GGCTTGACAG
     CGGTACCTAC CCTTGTCGGC CCGGTAGAGG TTTCGGAAAA TGAGGTCGAA CGACTGCTGT GTCGTCCAAC AGAACCTACC CGAGGAAGTA CCGAACTGTC
 596  A  M  D  G  N  S  R   A  I  S   K  A  F  Y   S  S  L   L  T  T    Q  Q  V  V    L  D  G   L  L  H    G  L  T  V

2001 TTCCACAGCT CCCTGTCCAC ACTCCCCAAG GTAACCAGAG TGGAGAAGGG AGTTCTCTT  GACTTACTTG TTGCATAGGT CAGGCTCCGC TCTTTCTATT
     AAGGTGTCGA GGGACAGGTG TGAGGGGTTC CATTGGTCTC ACCTCTTCCC TCAAGAGAA CTGAATGAAC AACGTATCCA GTCCGAGGCG AGAAAGATAA
 630  P  Q  L  P  V  H    T  P  Q  G   N  Q  S    G  E  G    R  F  S  Q       ^Start of intron sequence 2101 GCCATCACCT AGATCGCACC TGGCATTAG  TAGGTGCTCA ATAAATAACT GTGAACTGAG AGAATGAATG GGGATCTGAG GGAAACAAAC AGACCTCATC
     CGGTAGTGGA TCTAGCGTGG ACCGTAATC ATCCACGAGT TATTATTGA  CACTTGACTC TCTTACTTAC CCCTAGACTC CCTTTGTTTG TCTGGAGTAG 2201 CTGCATTCTT CCCACTCCCT TAGGTTCCCT ACTCCTGCTG GCTATTGTCT CCATGTCGGT AGGGCAAGAG CCTCAGGCCT TTGGAGTTGG AACCTCAATG
     GACGTAAGAA GGGTGAGGGA ATCCAAGGGA TGAGGACGAC CGATAACAGA GGTACAGCCA CTCATGACCA TCCCGTTCTC GGAGTCCGGA AACCTCAATG
   1                                                                                                    S  Y
                                                                                           2nd ORF starts from here!^

2301 TCTTTGCTTT TCTCCACAGG AGCCCCGCAA GTGAGCCAGC CACTGCGAGA GGAGAGTGAG GCAGAGTGAG GATATACCTG GAGCCATTTC CTCTGCCCTG GCAGCCATAT
     AGAAACGAAA AGAGGTGTCC TCGGGGCGTT CACTCGGTCG GTGACGCTCT CCTCTCACTC CGTCTCACTC CTATATGGAC CTCGGTAAAG GAGACGGGAC CGTCGGTATA
   3  S  L  L  F  S  T  G   A  P  Q   V  S  Q  P   L  R  E   Q  S  E    D  I  P  G    A  I  S   S  A  L    A  A  I  C

2401 GCACTGCTCC TGTGGGACTC CCCGACTGCT GGGATGCCAA TGTTGGCATT TGGCAAATCA GCTAACTGAA ACCGTTTAGT CGATTGACTT CGTCGTCGG TCGAGTCCGG
     CGTGACGAGG ACACCCTGAG GGGCTGACGA CCCTACGGTT ACAACCGTAA ACCGTTTAGT CGATTGACTT CGATTGACTT GCTAACTGAA GCAGCAGCC AGCTCAGGCC
   37 T  A  P  V  G  L    P  D  C  W   D  A  K    E  Q  V  C   W  H  L   A  N  Q    L  T  E  D   S  S  Q    L  R  P
```

FIG._4C

```
2501 ATCCCTCATC TCTGGCCTGC AGCATCCCAT CCTGTGCCTG CACCTTCTCA AGTTCTATA CTCCTGCCTG CTTGTCAGTG AGGGCCTGTG CCGTCTTCTG
     TAGGGAGTAG AGACCGGACG TCGTAGGGTA GGACACGGAC GTGGAAGAGT TCCAAGATAT GAGGACGACG GAACAGTGAC TCCCGGACAC GGCAGAAGAC
 70   S   L   I   S   G   L   Q   H   P   I   L   C   L   H   L   L   K   V   L   Y   S   C   C   L   V   S   E   G   L   C   R   L   L

2601 GGGCAGGAGC CCCTGGCCTT GGAATCCCTG TTTATGTTGA TTCAGGGCAA GGTAAAAGTA CTAGGACAGTG AAGAGTCTAC TGAAGTGACA CTCTACTTCC
     CCCGTCCTCG GGGACCGGAA CCTTAGGGAC AAATACAACT AAGTCCCGTT CCATTTCAT CATCCAGATG TTCTCACTGT ACTTCACTGT GAGATGAAGG
103   G   Q   E   P   L   A   L   E   S   L   F   M   L   I   Q   G   K   V   K   V   D   W   E   E   S   T   E   V   T   L   Y   F   L

2701 TCTCCCTTCT TGTCTTTTCG CTCCAAAACC TGCCTTGTGG AATGGAGAAG CTAGGCAGTG ACGTTGCTAC TCTCTTTACC CATTCGCATG TCGTCTCTCT
     AGAGGGAAGA ACAGAAAGC GAGGTTTTGG ACGGAACACC TTACCTCTTC GATCCGTCAC TGCAACGATG AGAGAAATGG GTAAGCGTAC AGCAGAGAGA
137   S   L   L   V   F   R   L   Q   N   L   P   C   G   M   E   K   L   G   S   D   V   A   T   L   F   T   H   S   H   V   V   S   L

2801 TGTGAGTGCA GCAGCCTGTC TATTGGGACA CAAGGGGTGA GCTTGGTCAG CCAGCCCATG CCTTTGACCT GAATGGATGG CTGCAGCCAC ACATGCCTTG
     ACACTCACGT CGTCGGACAG ATAACCCTGT GTTCCCCACT CGAACCAGTC GGTCGGGTAC GGAAACTGGA CTTACCTACC GACGTCGGTG TGTACGGAAC
170   V   S   A   A   C   L   L   G   Q   Q   G   V   T   F   D   L   Q   P   M   E   W   M   A   A   A   T   H   A   L

2901 TCTGCCCCTG CAGAGGTTCG GTTGACTCCA CCAGGTAGTT GTGGATTCTA TGATGGCCTC CTTATCCTTC TGTTGCAGCT CCTCACTGAG CAGGGGAAGG
     AGACGGGGAC GTCTCCAAGC CAACTGAGGT GGTCCATCAA CACCTAAGAT ACTACCGGAG GAATAGGAAG ACAACGTCGA GGAGTGACTC GTCCCCTTCC
203   S   A   P   A   E   V   R   L   T   P   P   G   S   C   G   F   Y   D   G   L   L   I   L   L   Q   L   T   E   Q   G   K   A

3001 CTAGCCTAAT CAGGGGATATG TCCAGTTCAG AAATGTGGAC CGTTTTGTGG GCAAAACACC CACCGCTTCT CCATGGTCCT GAGGCTCCCC GAGGAGGCAT CTGCACAGGA
     GATCGGATTA GTCCCTATAC AGGTCAAGTC TTTACACCTG GCAAAACACC CGTTTTGTGG GTGGCGAAGA GGTACCAGGA CTCCGAGGG CTCCTCCGTA GACGTGTCCT
237   S   L   I   R   D   M   S   S   S   E   M   W   T   V   L   W   H   R   F   S   M   V   L   R   L   P   E   E   A   S   A   Q   E

3101 AGGGGAGCTT TCGCTATCCA GTCCACCAAG CCCTGAGCGC GACTGGACAC TGATTTCTCC CCAGGGCATG GCAGCCCTGC TGAGCCTGGC CATGGCCACC
     TCCCCTCGAA AGCGATAGGT CAGGTGGTTC GGGACTCGCT CTGACCTGTG ACTAAAGAGG GGTCCCGTAC CGTCGGGACG ACTCGGACCG GTACCGGTGG
270   G   E   L   S   L   S   S   P   P   S   P   E   P   D   W   T   L   I   S   P   Q   G   M   A   A   L   L   S   L   A   M   A   T

3201 TTTACCCAGG AGCCCCAGTT ATGCCTGAGC TGCCTGTCCC AGCATGGAAG TATCCTTCATG TCCATCCTGA AGCATCTGCT TTGCCCCCAGC TTCCTGAATC
     AAATGGGTCC TCGGGGTCAA TACGGACTCG ACGGACAGGG TCGTACCTTC ATAGGAGTAC AGGTAGGACT TCGTAGACGA AGCATCTGCT TTGCCCCCAGC TTCCTGAATC
303   F   T   Q   E   P   Q   L   C   L   S   Q   H   G   S   I   L   M   S   I   L   K   H   L   L   C   P   S   F   L   N   Q

3301 AACTGCGCCA GGCGCCTCAT GGGTCTGAGT TTCTCCCTGT CTGTGTGCTC AGTCCTTTG CTTCCCCCTTT GCGCTGGACA TGGATGCTGA
     TTGACGCGGT CCGCGGAGTA CCCAGACTCA AAGAGGGACA GACACGACGAG TCGAGGAAAC GAAGGGGAAA CGCGACCTGT ACCTACGACT
337   L   R   Q   A   P   H   G   S   E   F   L   P   V   V   L   S   V   C   Q   L   L   C   F   P   F   A   L   D   M   D   A   D
```

*FIG._4D*

```
3401  CCTCCTTATA GTTGTCTTGG CCGACCTCAG GGACTCAGAA GTTGCAGCCC ATCTGCTGCA GGTCTGCTGC TACCATCTTC CGTTGATGCA AGTGGAGCTG
      GGAGGAATAT CAACAGAACC GGCTGGAGTC CCTGAGTCTT CAACGTCGGG TAGACGACGT CCAGACGACG ATGGTAGAAG GCAACTACGT TCACCTCGAC
370   L  L  I    V  V  L  A    D  L  R    D  S  E    V  A  A  H    L  L  Q    V  C  C    Y  H  L  P    L  M  Q    V  E  L

3501  CCCATCAGCC TTCTCACACG CCTGGCCCTC ATGGATCCCA CCCTCTCTCAA CCAGTTTGTG AACACAGTGT CTGCCCTCCC TAGAACCATC GTCTCGTTTC
      GGGTAGTCGG AAGAGTGTGC GGACCGGGAG TACCTAGGGT GGAGAGAGTT GGTCAAACAC TTGTGTCACA GACGGGAGGG ATCTTGGTAG CAGAGCAAAG
403   P  I  S    L  L  T  R    L  A  L    M  D  P  T    L  T  S    Q  F  V    N  T  V  S    A  S  P    R  T  I    V  S  F  L

3601  TCTCAGTTGC CCTCCTGAGT GACCAGCCAC TGTTGACCTC CGACCTTCTC TCTCTGCTGG CCCATACTGC CAGGGTCCTG TCTCCCAGCC ACTTGTCCTT
      AGAGTCAACG GGAGGACTCA CTGGTCGGTG ACAACTGGAG GCTGGAAGAG AGAGACGACC GGGTATGACG GTCCCAGGAC AGAGGGTCGG TGAACAGGAA
437   S  V  A    L  L  S    D  Q  P  L    L  T  S    D  L  L    S  L  L  A    H  T  A    R  V  L    S  P  S  H    L  S  F

3701  TATCCAAGAG CTTCTGGCTG GCTCCTGATGA ATCCTATCGG CCCATCCCAGAG GCCTCCTGGG GGGCACACAC CCCGTGTGTG TTATAGGCTC
      ATAGGTTCTC GAAGACCGAC CGAGACTACT TAGGATAGCC GGGGACCGT CGGAGGACCC CCGTGTGTG AATATCCGAG
470   I  Q  E    L  L  A  G    S  D  E    S  Y  R    P  L  R  S    L  L  G    H  P  E    N  S  V  R    A  H  T    Y  R  L

3801  CTGGACACT TGCTCCAACA CAGCATGGCC CTGCTCAGAG CCAGTCTGGA GCTGGTCCTC TGGGACCTGC CCTGGCAGCT GCAGTGCCCA GACAAGGATC
      GACCCTGTGA ACGAGGTTGT GTCGTACCGG GACGAGTCTC GGTCAGACCT CGACCAGGAG ACCCTGGACG GGACCGTCGA CGTCACGGGT CTGTTCCTAG
503   L  G  H    L  L  Q  H    S  M  A    L  R  G  A    L  Q  S    Q  S  G    L  L  S  L    L  L  L    G  L  G    D  K  D  P

3901  CTGTTGTGCG GTGCAGTGCC AGCTTTGCTG TGGGCAATGC ACCCGTTACG AGCCTACCAG TCGGATGGTC GCAGTGCCCA CGTCACGGGT CATACTGGGT
      GACAACACGC CACGTCACGG TCGAAACGAC ACCCGTTACG TGGGCAATTG TCGGATGCTC AGCCTACCAG TCGGATGGTC GCAGTGCCCA CGTCACGGGT CATACTGGGT
537   V  V  R    C  S  A    S  F  A  V    G  N  A    A  Y  Q    A  G  P  L    G  P  A    L  A  A    A  V  P  S    M  T  Q

4001  GCTGCTTGGA GATCCTCAGG GCGCAATGTT TGGGCAACTT CCAAACCCTC GGGACCTGAA GGTTTGGGAG AGGAGCTGTT ACAGTGCGAA
      CGACGAACCT CTAGGAGTCC CGCGTTACAA ACCCGTTGAA CGTAGTGGAG CCCTGGACTT CCAAACCCTC TCCTCGACAA TGTCACGCTT
570   L  L  G    D  P  Q  A    G  I  R    R  N  V    A  S  A  L    G  N  L    G  P  E    G  L  G  E    L  L  Q  E

4101  GTACCCCAGC GGCTCCTAGA AATGGCATGT GGAGACCCCC AGCCAAATGT GAAGGAGGCT CCCTCCGGAG GCCCTCATTG CCTGCAACAG CCTGCAGCA GAGCCTGGCA
      CATGGGGTCG CCGAGGATCT TTACCGTACA CCTCTGGGGG TCGGTTTACA CTTCCTCCGA GGGAGGCCTC CGGGAGTAAC GGACGTTGTC CTCGGACCCT
603   V  P  Q  R    L  L  E    M  A  C    G  D  P  Q    P  N  V    K  E  A    A  L  I  A    L  R  S    L  Q  Q    E  P  G  I
```

*FIG. 4E*

```
4201  TCCATCAGGT ACTGGTGTCC CTGGGTGCCA GTGAGAAACT ATCCTTGCTC TCTCTGGGGA ATCAGTCACT GCCACACAGC AGTCCTAGGC CTGCCTCTGC
      AGGTAGTCCA TGACCACAGG GACCCACGGT CACTCTTTGA TAGGAACGAG AGAGACCCCT TAGTCAGTGA CGGTGTGTCG TCAGGATCCG GACGAGACG
 637       H  Q  V  L  V  S     L  G  A  S        E  K  L     S  L  L        S  L  G  N     Q  S  L     P  H  S     S  P  R  P     A  S  A

4301  CAAACACTGC AGGAAACTCA TTCACCTCCT GAGGCCAGCC CATAGCATGT GATTCCAGAT TCCTGCGGTC CAGCCTCCAA CTTTGGTTGC CAGCTCTTTC
      GTTTGTGACG TCCTTTGAGT AAGTGGAGGA CTCCGGTCGG GTATCGTACA CTAAGGTCTA AGGACGCCAG GTCGGAGGTT GAAACCAACG GTCGAGAAAG
 670       K  H  C     R  K  L  I     H  L  L     R  P  A     H  S  M  O

4401  TTATTCTACT ACACAAGCCG CCAACTCAAC TGAGAGCTAA AGAGACTAGA AAAGAGATAA AGCTGCCAACT CAACTGAGAA CAAGAAACTA GAAGAGATTT
      AATAAGATGA TGTGTTCGGC GGTTGAGTTG ACTCTGATT TCTCTGATCT TTTCTCTATT CGACGGTTGA GTTGACTCTT GTTCTTTGAT CTTCTCTAAA

4501  ATATATAAAG CTTCTTCCTT CTCCCAATAAT GTGCCTTTAA CTCTAGGGAC CTGCCTCACG GACCTTAGGG AAAAACCTCA ACCTGAAAGA TCTCTTCCTT TCTGAGCTC
      TATATATTTC GAAGAAGGAA GAGGGTTATTA CACGGAAATT GAGATCCCTG GACGGAGTGC CTGGAATCCC TTTTTGGAGT TGGACTTTCT AGAGAAGAA AGACCTCGAG

4601  GGGGCCTTTT CTCCAATAAT GTGCCTTTAA CTCTAGGGAC CTGCCTCACG GACCTTAGGG AAAAACCTCA ACCTGAAAGA TCTCTTCCTT TCTGAGCTC
      CCCCGGAAAA GAGGTTATTA CACGGAAATT GAGATCCCTG GACGGAGTGC CTGGAATCCC TTTTTGGAGT TGGACTTTCT AGAGAAGAA AGACCTCGAG

4701  CTTTAATCTT CCCAGCAGGT TTTTGCCTTA GACGTGCTGG CCCCAGGACA GTGATGAAGA CAGAGCCTGT CTCAGCTCTA GGCTGTGGGG ATCAATGCCA
      GAAATTAGAA GGGTCGTCCA AAAACGGAAT CTGCACGACC GGGGTCCTGT CACTACTTCT GTCTCGGACA GAGTCGAGAT CCGACACCCC TAGTTACGGT

4801  TCAGTCCCTG TTATTGAGGG ATTATCCCTT AGCCAACATT CCTATCTGTG GGTGGGCGTG GAGAGTGTAT CTTTTTTTGG GGTGTGTGTG TATATGTGTG
      AGTCAGGGAC AATAACTCCC TAATAGGGAA TCGGTTGTAA GGATAGACAC CCACCCGCAC CTCTCACATA GAAAAAACC CCACACACAC ATATACACAC

4901  TGTGTATGTG TGTGTGTGTT GTTTGTAAAC TCTTTTAATA AAGTTGTGC CTCACCATAC TTGAAGCTCC CAGGACAAGG GTTGAGAGGC
      ACACACATAC ACACACACAA CAAACATTTG AGAAAATTAT TTTCAACACG GAGTGGTATG AACTTCGAGG GTCCTGTTCC CAACTCTCCG

5001  TCAACCCCTC TTTCAGCTTC TATGTGGTGT TGGAGGTGCT TCACACACAAA AAAAAAAAAAA AAAAAAAAAA
      AGTTGGGGAG AAAGTCGAAG ATACACCACA ACCTCCACGA AGTGTGTTTT TTTTTTTTTT TTTTTTTTTT

5101  AAAAAAAAAA AAAAAAAAAA AAAAA
      TTTTTTTTTT TTTTTTTTTT TTTTT
```

```
701  GCACCCCTCC CTTCTATGCT ACAAGCATCT TTCAGCTGGT CAGCCTCATT ACAAGCATCT GCCCTCAACC ATCAGTCCCT GCTTTAAGAA
     CGTGGGGAGG GAAGATACGA TGTTCGTAGA AAGTCGACCA GTCGGAGTAA GAGTTCCTGG CGGGAGTTGG TAGTCAGGGA CGAAATTCTT
197   T  P  P   F  Y  A   T  S  I  F   Q  L  V   S  L  I  I   L  K  D  P   V  R  W   P  S  T   I  S  P  C   F  K  N

801  CTTCCTGCAG GGACTGCTCA CCAAAGACCC ACGGCAGCGA CAGACCTCTT ATATCACCCC TTTATTGCTG GTCATGTCAC CATAATAACT
     GAAGGACGTC CCTGACGAGT GGTTTCTGGG TGCCGTCGCT GTCTGGAGAA TATAGTGGGG AAATAACGAC CAGTACAGTG GTATTATTGA
230   F  L  Q   G  L  L  T   K  D  P   R  Q  R   L  S  W  P   D  L  L   Y  H  P   F  I  A  G   H  V  T   I  I  T

901  GAGCCAGCAG GCCCAGATTT GGGGACCCCA GCCTACCCCC AGAACTTCAG GTCCTAAAGG ACGAACAGGC CCATGGTTG GCCCCCAAGG
     CTCGGTCGTC CGGGTCTAAA CCCCTGGGGT CGGATGGGGG TCTTGAAGTC CAGGATTTCC TGCTTGTCCG GGTAGCCAAC CGGGGGTTCC
263   E  P  A  G   P  D  L   G  T  P   A  Y  P   Q  N  F  R   S  K  R   L  L  S   L  V  K  D   E  Q  A   H  R  L   A  P  K  G

1001 GTAATCAGTC TCGCATCTTG ACTCAGGCCT ATAAACGCAT GGCTGAGGAG GCCATGCAGA AGAAACATCA CCTGCCCTTG AGCAAGAGGA
     CATTAGTCAG AGCGTAGAAC TGAGTCCGGA TATTTGCGTA CCGACTCCTC CGGTACGTCT TCTTTGTAGT GGACGGGAAC TCGTTCTCCT
297   N  Q  S   R  I  L   T  Q  A  Y   K  R  M   A  E  E   A  M  Q  K   K  H  Q   N  T  G   P  A  L  E   Q  E  D

1101 CAAGACCAGC AAGGTGGCTC CTGGCACAGC CCCTCTGCCC AGACTCGGGG CCACTCCTCA GGAATCAAGC CTCCTGGCCG GGATCTTAGC CTCAGAATTG
     GTTCTGGTCG TTCCACCGAG GACCGTGTCG GGGAGACGGG TCTGAGCCCC GGTGAGGAGT CCTTAGTTCG GAGGACCGGC CCTAGAATCG GAGTCTTAAC
330   K  T  S   K  V  A  P   G  T  A   P  L  P   R  L  G  A   T  P  Q   E  S  S   L  L  A  G   I  L  A   S  E  L

1201 AAGAGCAGCT GGCTAAAATC AGGGACTGGA GAGGTGCCCT CTGCACCTCG GAAAACCGG ATTGTGAACG AGCATTCCCA GAGGAGAGGC
     TTCTCGTCGA CCCGATTTAG TCCCTGACCT CTCCACGGGA GACGTGGAGC CCTTTTGGCC TAACACTTGC TCGTAAGGGT CTCCTCTCCG
363   K  S  S  W   A  K  S   G  T  G   E  V  P  S   A  P  R   E  N  R   T  T  P  D   C  E  R   A  F  P   E  E  R  P

1301 CAGAGGTGCT GGGCCAGCGG AGCACTGATG TAGTGGACCT GGAAAATGAG GAGCCAGACA GTGGCAGCAC CTGCTAGAGA CCACTGAGCC
     GTCTCCACGA CCCGGTCGCC TCGTGACTAC ATCACCTGGA CCTTTTACTC CTCGGTCTGT CACCGTCGTG GACGATCTCT GGTGACTCGG
397   E  V  L   G  Q  R   S  T  D  V   V  D  L   E  N  E   E  P  D  S   D  N  E   W  Q  H   L  L  E  T   T  E  P

1401 TGTGCCTATT CAACTGAAGG CTTGCTGTGT AATCCTGACT TTAGGACTGA GAACGACACA TCTGCCAGCG CATCCAGAGT CAGCTGCATG AAGCTGGAGG GCAGATCCTG
     ACACGGATAA GTTGACTTCC GAACGACACA TTAGGACTGA ATCCTGACT AATCCTGACT GTAGGTCTCA AGACGCTCGC GTACGGTAC TTCGACCTCC CGTCTAGGAC
430   V  P  I   Q  L  K  A   P  L  T   L  L  C   N  P  D  F   C  Q  R   I  Q  S   Q  L  H  E   A  G  G   Q  I  L

1501 AAAGGCATCT TGGAGGGTGC TTCCACACATC CTGCCTGCAT TCCGGGTCCT GCAGTGATTC CTCTCCAGCT GCAGTCCCT GCAGTGATTC TATTCCTTCT
     TTTCCGTAGA ACCTCCCACG AAGGTGTAG GACGGACGTA AGGCCCAGGA CGTCACTAAG GAGAGGTCGA CGTCACTAAG ACAACGGAAC ATAAGGAAGA
463   K  G  I  L   E  G  A   S  H  I   L  P  A  F   R  V  L   S  S  L   L  S  S  C   S  D  S   V  A  L   Y  S  F  C
```

FIG._5B

```
1601 GCGGGAGGC AGGGCTTCCT GGGCTGCTGC TGAGTCTACT CAGGCACAGT GCAGCAATCT TGGTATGGA CCTTCTTACA
     CGGCCCTCCG TCCCGAAGGA CCCGACGACG ACTCAGATGA GTCCGTGTCA CGTCGTTAGA ACCATACCCT GGAAGAATGT
497    R   E   A   G   L   P   G   L   L   L   S   L   L   R   H   S   Q   E   S   N   S   L   Q   Q   Q   S   W   Y   G   T   F   L   Q

1701 GGACCTGATG GCTGTGATTC AGGCCTACTT TGCCTGTACC TTCAATCTGG AGAGGAGCCA GACAAGTGAC AGCCTGCAGG TGTTTCAGGA GGCTGCCAAC
     CCTGGACTAC CGACACTAAG TCCGGATGAA ACGGACATGG AAGTTAGACC TCTCCTCGGT CTGTTCACTG TCGGACGTCC ACAAAGTCCT CCGACGGTTG
530    D   L   M   A   V   I   Q   A   Y   F   A   C   T   F   N   L   E   R   S   Q   T   S   D   S   L   Q   V   F   Q   E   A   A   N

1801 CTTTTTCTGG ACCTGTTGGG GAAACTGCTG GCCCAACCAG ATGACTCTGA GCAGACTCTG CGGAGGACA GCCTTATGTG CTTTACTGTC CTGTGCGAAG
     GAAAAAGACC TGGACAACCC CTTTGACGAC CGGGTTGGTC TACTGAGACT CGTCTGAGAC GCCTCCTGT CGGAATACAC GAAATGACAG GACACGTTC
563    L   F   L   D   L   L   G   K   L   L   A   Q   P   D   D   S   E   Q   T   L   R   R   D   S   L   M   C   F   T   V   L   C   E   A

1901 CCATGGATGG GAACAGCCGG CCCATCTCCA AAGCCTTTTA CTGACGACAC CTGGTTGT CTTGGATGGG CTCCTTCATG GCTTGACAGT
     GGTACCTACC CTTGTCGGCC GGGTAGAGGT TTCGGAAAAT GACTGCTGTG GAGGTCGAAC TCGTCCAACA GAACCTACCC CGAGAAGTAC CGAACTGTCA
597    M   D   G   N   S   R   A   I   S   K   A   F   Y   S   S   L   L   T   T   Q   Q   V   V   L   D   G   L   L   H   G   L   T   V

2001 TCCACAGCTC CCTGTCCACA CTCCCCAAGG TTCCCTACTC CTGCTGCCAT GTCGGTGAGT ACTGGTGCTA TTGTCTAGGG CAAGAGCCTC AGGCCTTTGG
     AGGTGTCGAG GGACAGGTGT GAGGGGTTCC AAGGGATGAG GACGACGGTA CAGCGCACTA TGACCACGAT AACAGATCCC GTTCTCGGAG TCCGAAACC
630    P   Q   L   P   V   H   T   P   Q   G   S   L   L   L   L   P   C   R   D

2101 AGTTACTCTT TGCTTTTCTC CACAGGAGCC CCGCAAGTGA GCCAGCCACT GCGAGAGCAG AGTGAGGATA TACCTGAGC CATTTCCTCT GCCCTGGCAG
     TCAATGAGAA ACGAAAAGAG GTGTCCTCGG GGCGTTCACT CGGTCGGTGA CGCTCTCGTC TCACTCCTAT ATGGACCTCG GTAAAGAGA CGGGACCGTC
1      S   Y   S   L   F   S   T   G   A   P   Q   V   S   Q   P   L   R   E   Q   S   E   D   I   P   G   A   I   S   S   A   L   A   A
       ^2nd ORF starts from here 2201 CCATATGCAC TGCTCCTGTG GGACTGCCCG CCTGACGGGC TGACGACCCT ACGGTTCCTC ACGGTCTGTT TGCCAAGGAG CAGGTCTGTT AAATCAGCTA AATGAAGACA GCAGCCAGCT
     GGTATACGTG ACGAGGACAC CCTGACGGGC GGACTGCCCG ACTGCTGGGA TGCCAAGGAG TGCCAGACAA ACGGTTCCTC GTCCAGACAT TTTAGTGAT TGACTTCTGT CGTCGGTCGA
35     I   C   T   A   P   V   G   L   P   D   C   W   D   A   K   E   Q   V   C   W   H   L   A   N   Q   L   T   E   D   S   S   Q   L 2301 CAGGCCATCC CTCATCTCTG GCCTGCAGCA TCCCATCCTG TGCCTGCACC TTCTCAAGGT TCTATACTCC TGCTGCCTTG TCAGTGAGGG CCTGTGCCGT
     GTCCGGTAGG GAGTAGAGAC CGGACGTCGT AGGGTAGGAC ACGGACGTGG AAGAGTTCCA AGATATGAGG ACGACGGAAC AGTCACTCCC GGACACGGCA
68     R   P   S   L   I   S   G   L   Q   H   P   I   L   C   L   H   L   L   K   V   L   Y   S   C   C   L   V   S   E   G   L   C   R 2401 CTTCTGGGGC AGGAGCCCCT GGCCCTTGAA TGTTGATTCA TGTTGATTCA AAAGTAGTAG GGGCAAGGTA ATTGGGAAGA GTCTACTGAA GTGACACTCT
     GAAGACCCCG TCCTCGGGA CCGGGAACTT ACAACTAAGT ACAACTAAGT TTTCATCATC CCCGTTCCAT TAACCCTTCT CAGATGACTT CACTGTGAGA
101    L   L   G   Q   E   P   L   A   L   E   S   L   F   M   L   I   Q   G   K   V   K   V   V   D   W   E   E   S   T   E   V   T   L   Y
```

FIG._5C

```
2501 ACTTCCTCTC CCTTCTTGTC TTTCGGCTCC AAAACCTGCC TTGTGGAATG GAGAAGCTAG GCAGTGACGT TGCTACTCTC TTTACCCATT CGCATGTCGT
     TGAAGGAGAG GGAAGAACAG AAAGCCGAGG TTTTGGACGG AACACCTTAC CTCTTCGATC CGTCACTGCA ACGATGAGAG AAATGGGTAA GCGTACAGCA
 135  F   L   S   L   L   V   F   R   L   Q   N   L   P   C   G   M   E   K   L   G   S   D   V   A   T   L   F   T   H   S   H   V   V

2601 CTCTCTTGTG AGTGCAGCAG CCTGTCTATT GGGACAGCTT GGTCAGCAAG GGGTGACCTT TGACCTCCAG CCCATGGAAT GGATGGCTGC AGCCACACAT
     GAGAGAACAC TCACGTCGTC GGACAGATAA CCCTGTCGAA CCAGTCGTTC CCCACTGGAA ACTGGAGGTC GGGTACCTTA CCTACCGACG TCGGTGTGTA
 168  S   L   V   S   A   A   A   C   L   L   G   Q   L   G   Q   Q   G   V   T   F   D   L   Q   P   M   E   W   M   A   A   A   T   H

2701 GCCTGTCTG CCCCTGCAGA GCTCCTCACT GAGGTACAGA TGGATCTTGG GATGGATGGG AAGTAAAGAG AGAGGAACTG GGCATTTGG GGAGCCTCTG
     CGGAACAGAC GGGGACGTCT CGAGGAGTGA CTCCATGTCT ACCTAGAACC CTACCTACCC TTCATTCTC TCTCCTTGAC CCGTAAAACC CCTCGGAGAC
 201  A   L   S   A   P   A   E   L   L   T   E   V   Q   M   D   L   G   M   D   G   K   Q

2801 GACCAGAGA ATGAAGAAGC CTTCCCTCTC AAGCTACTGT GCCTGTGATA TTTCCCGCCT TTTCCCGCCT GCCCCTCAGTA CTGACCCTTT
     CTGGTCTCCT TACTTCTTCG TTGGGTGTCG GAAGGGAGAG TTCGATGACA CGGAACCTTG AAGGGGCGA CGGGAGTCAT GACTGGGAAA

2901 GAAGGAAACC ATTCGCTGCG TCCCCTGGGA GATAAAATGA ATTCCCTGGG CATACACATG AGTTGTGAGG TCAGAGGGTT
     CTTCCTTTGG TAAGCGACGC AGGGGACCCT CTATTTTACT TAAGGGACCC GTATGTGTAC TCAACACTCC AGTCTCCCAA

3001 AAGGTTTGAT AAGAAAATGA ATAAGACGA CAGGGAATA CTAGGTGGGA AAGCGGAAGG AATTATTTCT GGGACTTCCT TTACTTGTAA GTCAGGGACA
     TTCCAAACTA TTCTTTTACT TTATTCTGCT GTCCCTTAT GATCCACCCT TTCGCCTTCC CTTAATAAAGA CCCTGAAGGA AATGAACATT CAGTCCCTGT

3101 GGAATGAATA AAAGCATTTG GATTCCTGAC TTCTGTCTTT CCCCCCGCCC TCTTTCACTT CAGGGGAAGG CTAGCCTAAT CAGGGATATG
     CCTTACTTAT TTTCGTAAAC CTAAGGACTG AAGACAGAAA GGGGGGCGGG AGAAAGTGAA GTCCCCTTCC GATCGGATTA GTCCCTATAC

3201 TCCAGTTCAG AAATGTGGAC CGTTTTGTGG CACCGCTTCT CCATGGTCCT GAGGCTCCCC GAGGAGGCAT CTGCACAGA AGGGGAGCTT TCGCTATCCA
     AGTCAAGTC TTTACACCTG GCAAAACACC GTGGCGAAGA GGTACCAGGA CTCCGAGGGG CTCCTCCGTA GACGTGTCCT TCCCCTCGAA AGCGATAGGT

3301 GTCCACCAAG CCCTGAGCCA GACTGGACAC TGATTTCTCC CCAGGGCATG GCAGCCCTGC TGAGCCTGGC CATGGCCATG TTTACCAGG AGCCCCAGTT
     CAGGTGGTTC GGGACTCGGT CTGACCGTGT ACTAAAGAGG GGTCCCGTAC CGTCGGGACG ACTCGGACCG GTACCGGTAC AAATGGGTCC TCGGGGTCAA

3401 ATGCCTGAGC TGCCTGTCCC AGCATGGAAG TATCCTCATG AGCATCTGCT TTGCCCCAGC TTCCTGAATC AACTGCGCCA GGCGCCTCAT
     TACGGACTCG ACGGACAGGG TCGTACCTTC ATAGGAGTAC TCGTAGACGA AGGTAGACT AAGGACTTAG TTGACGCGGT CCGCGGAGTA

3501 GGGTCTGAGT TTCTCCCTGT CGTGGTGCTC CTTCCCCTTT AGCTCCTTTG GGCTGGACA TGGATGCTGA CCTCCTTATA GGTGTCTTGG
     CCCAGACTCA AAGAGGGACA GCACCACGAG AGACAGCGAG TCGAGACAAC CGCGACCTGT ACCTACGACT GGAGAATAT CCACAGAACC
```

FIG._5D

```
3601 CCGACCTCAG GGACTCAGAA GTTGCAGCCC ATCTGCTGCA GGTCTGCTGC TACCATCTTC CGTTGATGCA AGTGGAGCTG CCCATCAGCC TTCTCACACG
     GGCTGGAGTC CCTGAGTCTT CAACGTCGGG TAGACGACGT CCAGACGACG ATGGTAGAAG GCAACTACGT TCACCTCGAC GGGTAGTCGG AAGAGTGTGC

3701 CCTGGCCCTC ATGGATCCCA CCTCTCTCAA CCAGTTGTGT CTGCCTCCCC TAGAACCATC GTCTCGTTTC CTCTCAGTTGC CCTCCTGAGT
     GGACCGGGAG TACCTAGGGT GGAGAGAGTT GGTCAACACA GACGGAGGGG ATCTTGGTAG CAGAGCAAAG AGAGTCAACG GGAGGACTCA

3801 GACCAGCCAC TGTTGACCTC TCTCTGCTCTC CGACCTTCTC CAGGGTCCTG TCTCCCAGCC ACTTGTCCTT TATCCAAGAG CTTCTGGCTG
     CTGGTCGGTG ACAACTGGAG GCTGGAAGAG GCTGGAAGAG GTCCCAGGAC AGAGGGTCGG TGAACAGGAA ATAGGTTCTC GAAGACCGAC

3901 GCTCTGATGA ATCCTATCGG CCCCTGCCCA GCCTCCTGGG AATTCTGTGC GGGCACACAC TTATAGGCTC CTGGGACACT TGCTCCAACA
     CGAGACTACT TAGGATAGCC GGGGACGCGT CGGAGGACCC TTAAGACACG CCCGTGTGTG AATATCCGAG GACCCTGTGA ACGAGGTTGT

4001 CAGCATGGCC CTGCGTGGGG CACTGCAGAG CCAGTCTGGA CTGCTCAGCC TTCTGCTGCT TGGGCTTGGA GACAAGGATC CTGTTGTGCG GTGCAGTGCC
     GTCGTACCGG GACGCACCCC GTGACGTCTC GGTCAGACCT GACGAGTCGG AAGACGACGA ACCCGAACCT CTGTTCCTAG CACGTCACGG

4101 AGCTTTGCTG TGGGCAATGC AGCCTACCAG GCTGGTCCTC TGGGACCTGC CCTGGCAGCT GTATGACCCA GCTGCTTGGA GATCCTCAGG
     TCGAAACGAC ACCCGTTACG TCGGATGGTC CGACCAGGAG ACCCTGGACG GGACCGTCGA CGTACGGGT CATACTGGGT CGACGAACCT CTAGAGTCC

4201 CTGGTATCCG GCGCAATGTT GCATCAGCTC TGGGCAACTT GGGACCAGAAG CCCACACAGC AGGAGCTGTT ACAGTGCGAA GGCTCCTAGA
     GACCATAGGC CGCGTTACAA CGTAGTCGAG ACCCGTTGAA CCCTTGACTT CCAAACCCTC TCCTCGACAA TGTCACGCTT CCGAGGATCT

4301 AATGGCATGT GGAGACCCCC AGCCAAATGT GAAGGAGGCT CCCTCCATTG CCCTCCGGAG CCTGCAACAG GAGCCTGGCA TCCATCAGGT ACTGGTGTCC
     TTACCGTACA CCTCTGGGGG TCGGTTTACA CTTCCTCCGA GGGAGTAAC GGGAGCCCTC GGACGTTGTC CTCGGACCGT AGGTAGTCCA TGACCACAGG

4401 CTGGGTGCCA GTGAGAAACT ATCCTTGCTC TCTCTGGGGA ATCAGTCACT GCCACACAGC CTGCCTCTGC CAAACACTGC AGGAAAACTCA
     GACCCACGGT CACTCTTTGA TAGGAACGAG AGAGACCCCT TAGTCAGTGA CGGTGTGTCG GACGGAGACG GTTTGTGACG TCCTTTGAGT

4501 TTCACCTCCT GAGGCCAGCC CATAGCATGT GATTCCAGAT CTAAGGTCTA TCCTGCGGTC CAGCCTTCCA CAGCTCTTTC TTATTCTACT ACACAAGCCG
     AAGTGGAGGA CTCCGGTCGG GTATCGTACA CTAAGGTCTA AGGACGCCAG GTCGAGAAAG GTCGAGAATGA AATAAGATGA TGTGTTCGGC

4601 CCAACTCAAC TGAGAGCTAA AAAGAGATAA GCTGCCAACT CAAGAAACTA CAAGAAACTA GAAGAGATTT ATATATAAAG CTTCTCTCTT
     GGTTGAGTTG ACTCTCGATT TTTCTCTATT CGACGGTTGA GTTGACTCTT CTTCTCTAAA TATATATTTC GAAGAAGGAA
```

FIG._5E

```
4701  CTCCCAGATG CAGGATGTTT TCAACCAGTA AATTTTATTG CTGTTGGTGC CAGAGAAGAG TCCTTTCTTC TCTACATCCA GGGGCCTTTT CTCCAATAAT
      GAGGGTCTAC GTCCTACAAA AGTTGGTCAT TTAAAATAAC GACAACCACG GTCTCTTCTC AGGAAAGAAG AGATGTAGGT CCCCGGAAAA GAGGTTATTA

4801  GTGCCTTTAA CTCTAGGGAC CTGCCCTCAC GGACCTTAGGG AAAAACCTCA ACCTGAAAGA TCTCTTCCTT TCTGGAGCTC CTTTAATCTT CCCAGCAGGT
      CACGGAAATT GAGATCCCTG GACGGAGTGC CTGGAATCCC TTTTTGGAGT TGGACTTTCT AGAGAAGGAA AGACCTCGAG GAAATTAGAA GGGTCGTCCA

4901  TTTTGCCTTA GACGTGCTGG CCCCAGGACA GTGATGAAGA CAGAGCCTGT CTCAGCTCTA GGCTGTGGGG ATCAATGCCA TCAGTCCCTG TTATTGAGGG
      AAAACGGAAT CTGCACGACC GGGGTCCTGT CACTACTTCT GTCTCGGACA GAGTCGAGAT CCGACACCCC TAGTTACGGT AGTCAGGGAC AATAACTCCC

5001  ATTATCCCTT AGCCAACATT CCTATCTGTG GGTGGGCGTG GAGAGTGTAT CTTTTTTTGG GGTGTGTGTG TGTGTATGTG TGTGTGTGTT TGTGTGTGTT
      TAATAGGGAA TCGGTTGTAA GGATAGACAC CCACCCGCAC CTCTCACATA GAAAAAAACC ACACACACAC ACACATACAC ACACACACAA ACACACACAA

5101  TAATAGTTCT GTTTGTAAAC TCTTTTAATA AAAGTTGTGC CTCACCATAC TTGAAGCTCC CAGGACAAGG GTTGAGAGGC TCAACCCCTC TTTCAGCTTC
      ATTATCAAGA CAAACATTTG AGAAAATTAT TTTCAACACG GAGTGGTATG AACTTCGAGG GTCCTGTTCC CAACTCTCCG AGTTGGGGAG AAAGTCGAAG

5201  TATGTGGTGT TGGAGGTGCT GGTATCGTGT TCACACAAAA AAAAAAAAAA AA
      ATACACCACA ACCTCCACGA CCATAGCACA AGTGTGTTTT TTTTTTTTTT TT
```

FIG._5F

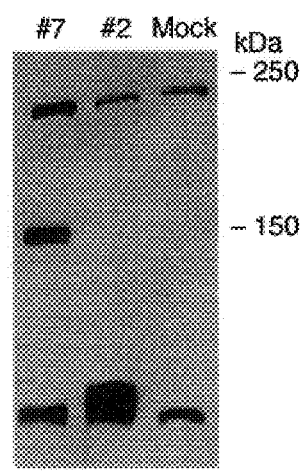
FIG._6
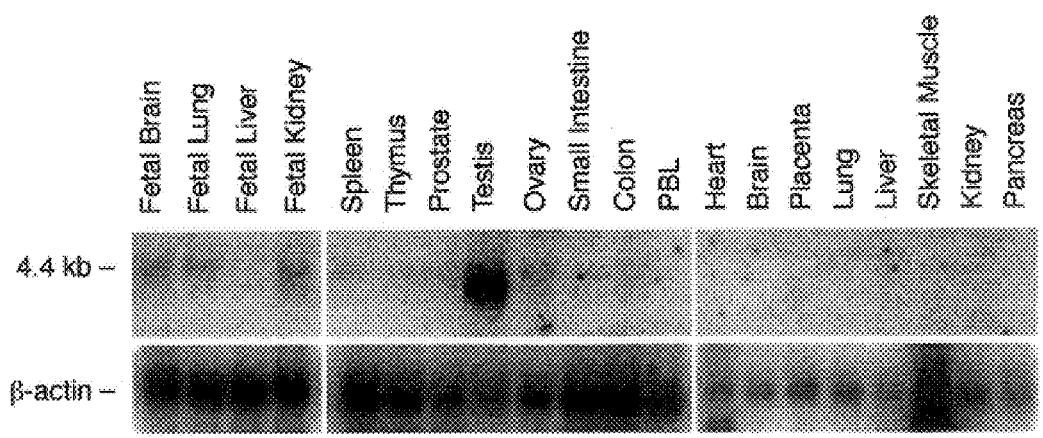
FIG._7

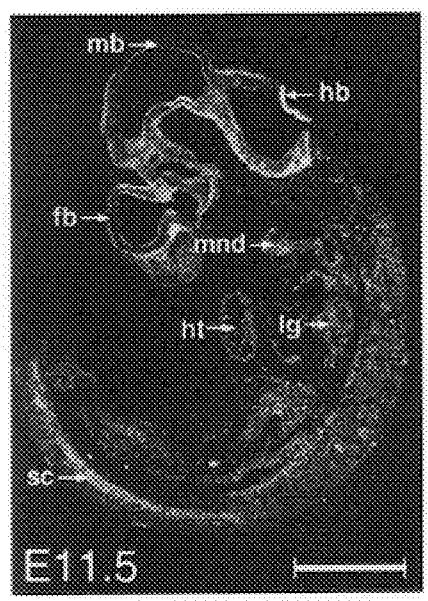
FIG._8A
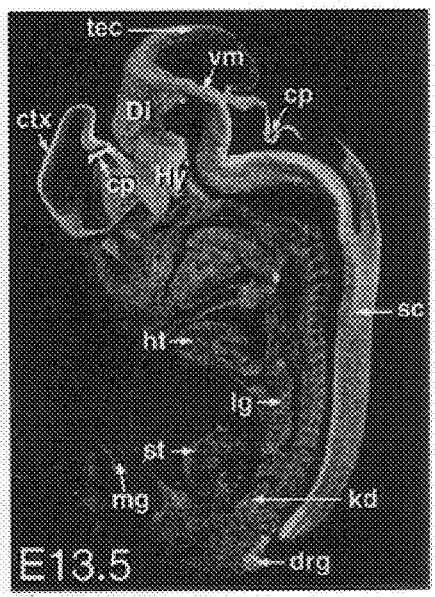
FIG._8B
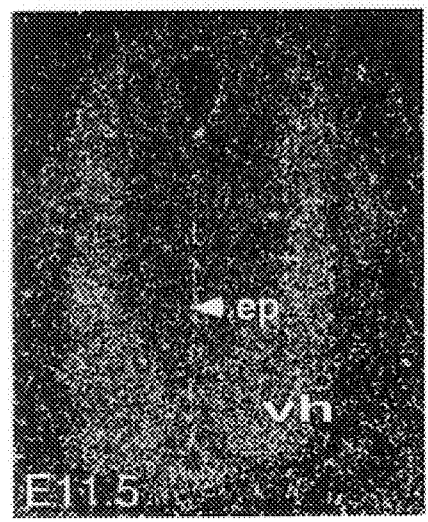
FIG._8C
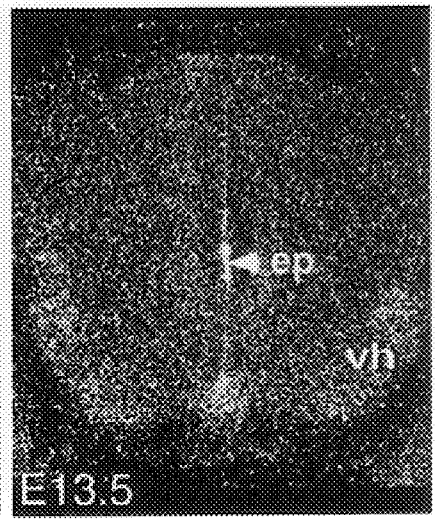
FIG._8D
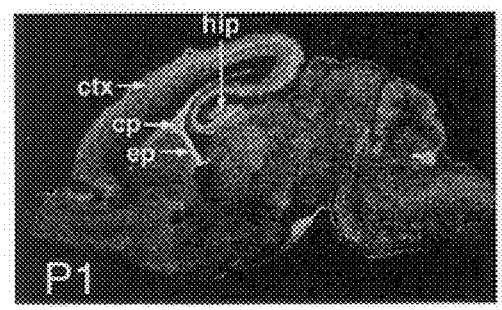
FIG._8E
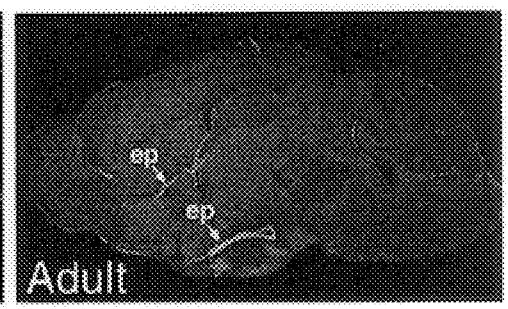
FIG._8F

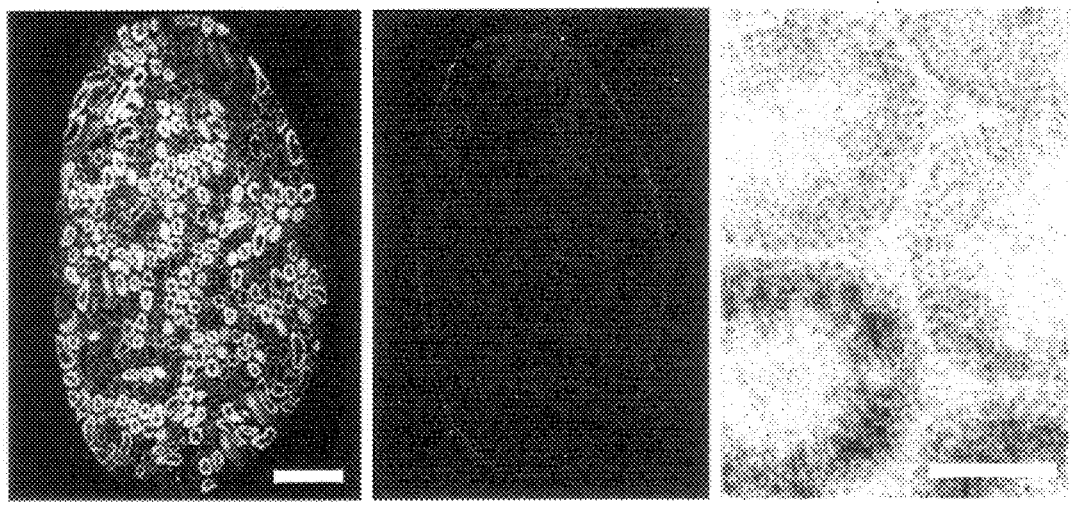
FIG._9A  FIG._9B  FIG._9C

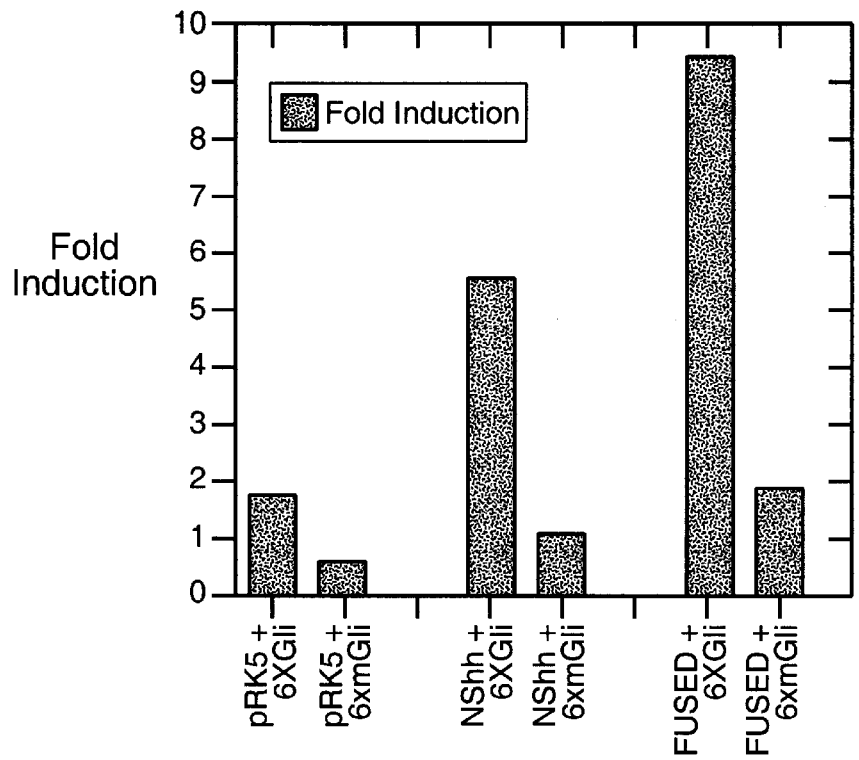
FIG._10A
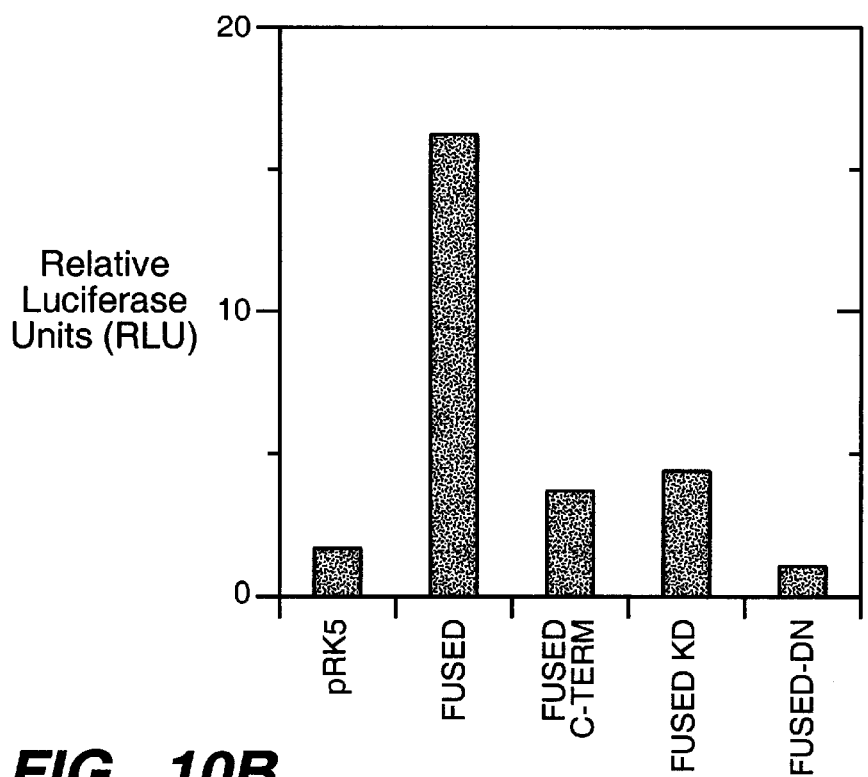
FIG._10B

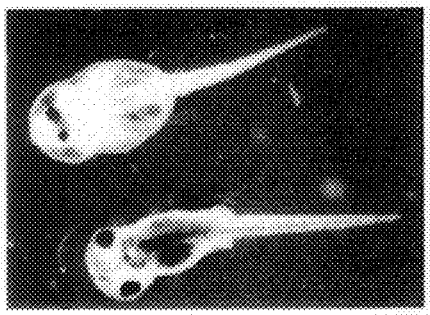
*FIG._11A*
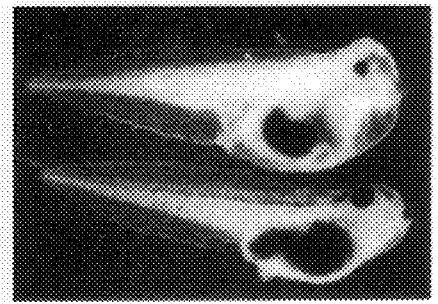
*FIG._11B*
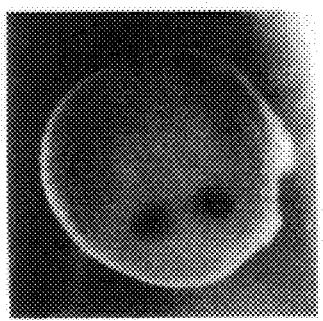
*FIG._11C*
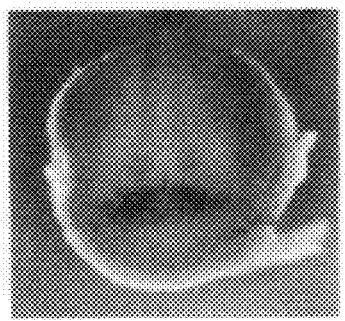
*FIG._11D*
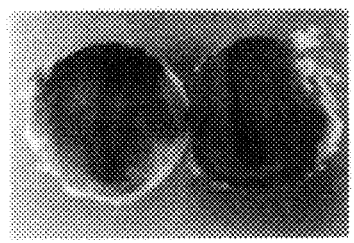
*FIG._11E*
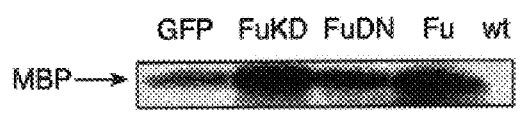
*FIG._12*

SEQUENCE LISTING

<160> NUMBER OF SEQ ID NOS: 27

<210> SEQ ID NO 1
<211> LENGTH: 4880
<212> TYPE: DNA
<213> ORGANISM: Homo sapiens
<220> FEATURE:
<221> NAME/KEY: unknown N
<222> LOCATION: 4160
<223> OTHER INFORMATION: unknown
<220> FEATURE:
<221> NAME/KEY: unknown N
<222> LOCATION: 4243
<223> OTHER INFORMATION: unknown
<220> FEATURE:
<221> NAME/KEY: unknown N
<222> LOCATION: 4361
<223> OTHER INFORMATION: unknown

<400> SEQUENCE: 1

| | | |
|---|---|---|
| cccggggatc tctagagat ccctcgacct cgacccacgc gtccgcccac | | 50 |
| gcgtccgccc acgcgtccgg ggcgtcccag atgttgtgga actgtccctg | | 100 |
| gatctatagc tcttcaccgt ctctactttc ttccttctaa gagatcctga | | 150 |
| aacctctgtc atg gaa aag tac cac gtg ttg gag atg att | | 190 |
| Met Glu Lys Tyr His Val Leu Glu Met Ile | | |
| 1 5 10 | | |
| gga gaa ggc tct ttt ggg agg gtg tac aag ggt cga aga | | 229 |
| Gly Glu Gly Ser Phe Gly Arg Val Tyr Lys Gly Arg Arg | | |
| 15 20 | | |
| aaa tac agt gct cag gtc gtg gcc ctg aag ttc atc cca | | 268 |
| Lys Tyr Ser Ala Gln Val Val Ala Leu Lys Phe Ile Pro | | |
| 25 30 35 | | |
| aaa ttg ggg cgc tca gag aag gag ctg agg aat ttg caa | | 307 |
| Lys Leu Gly Arg Ser Glu Lys Glu Leu Arg Asn Leu Gln | | |
| 40 45 | | |
| cga gag att gaa ata atg cgg ggt ctg cgg cat ccc aac | | 346 |
| Arg Glu Ile Glu Ile Met Arg Gly Leu Arg His Pro Asn | | |
| 50 55 60 | | |
| att gtg cat atg ctt gac agc ttt gaa act gat aaa gag | | 385 |
| Ile Val His Met Leu Asp Ser Phe Glu Thr Asp Lys Glu | | |
| 65 70 75 | | |
| gtg gtg gtg gtg aca gac tat gct gag gga gag ctc ttt | | 424 |
| Val Val Val Val Thr Asp Tyr Ala Glu Gly Glu Leu Phe | | |
| 80 85 | | |
| cag atc cta gaa gat gac gga aaa ctt cct gaa gac cag | | 463 |
| Gln Ile Leu Glu Asp Asp Gly Lys Leu Pro Glu Asp Gln | | |
| 90 95 100 | | |
| gtt cag gcc att gct gcc cag ttg gtg tca gcc ctg tac | | 502 |
| Val Gln Ala Ile Ala Ala Gln Leu Val Ser Ala Leu Tyr | | |
| 105 110 | | |
| tat ctg cat tcc cac cgc atc cta cac cga gat atg aag | | 541 |
| Tyr Leu His Ser His Arg Ile Leu His Arg Asp Met Lys | | |
| 115 120 125 | | |
| cct cag aac atc ctc ctc gcc aag ggt ggt ggc atc aag | | 580 |
| Pro Gln Asn Ile Leu Leu Ala Lys Gly Gly Gly Ile Lys | | |
| 130 135 140 | | |
| ctc tgt gac ttt gga ttt gcc cgg gct atg agc acc aat | | 619 |
| Leu Cys Asp Phe Gly Phe Ala Arg Ala Met Ser Thr Asn | | |
| 145 150 | | |
| aca atg gtg ctg aca tcc atc aaa ggc aca cca ctc tat | | 658 |

```
Thr Met Val Leu Thr Ser Ile Lys Gly Thr Pro Leu Tyr
    155                 160                 165 atg tct cca gag ctg gtg gag gag cga cca tac gac cac            697
Met Ser Pro Glu Leu Val Glu Glu Arg Pro Tyr Asp His
        170                 175 aca gcg gac ctc tgg tct gtt ggc tgc ata cta tat gaa            736
Thr Ala Asp Leu Trp Ser Val Gly Cys Ile Leu Tyr Glu
180                 185                 190 ctg gca gta ggc acc cct ccc ttc tat gct aca agc atc            775
Leu Ala Val Gly Thr Pro Pro Phe Tyr Ala Thr Ser Ile
            195                 200                 205 ttt cag ctg gtc agc ctc att ctc aag gac cct gtg cgc            814
Phe Gln Leu Val Ser Leu Ile Leu Lys Asp Pro Val Arg
                210                 215 tgg ccc tca acc atc agt ccc tgc ttt aag aac ttc ctg            853
Trp Pro Ser Thr Ile Ser Pro Cys Phe Lys Asn Phe Leu
    220                 225                 230 cag gga ctg ctc acc aaa gac cca cgg cag cga ctg tcc            892
Gln Gly Leu Leu Thr Lys Asp Pro Arg Gln Arg Leu Ser
        235                 240 tgg cca gac ctc tta tat cac ccc ttt att gct ggt cat            931
Trp Pro Asp Leu Leu Tyr His Pro Phe Ile Ala Gly His
245                 250                 255 gtc acc ata ata act gag cca gca ggc cca gat ttg ggg            970
Val Thr Ile Ile Thr Glu Pro Ala Gly Pro Asp Leu Gly
            260                 265                 270 acc cca ttc acc agc cgc cta ccc cca gaa ctt cag gtc           1009
Thr Pro Phe Thr Ser Arg Leu Pro Pro Glu Leu Gln Val
                275                 280 cta aag gac gaa cag gcc cat cgg ttg gcc ccc aag ggt           1048
Leu Lys Asp Glu Gln Ala His Arg Leu Ala Pro Lys Gly
    285                 290                 295 aat cag tct cgc atc ttg act cag gcc tat aaa cgc atg           1087
Asn Gln Ser Arg Ile Leu Thr Gln Ala Tyr Lys Arg Met
        300                 305 gct gag gag gcc atg cag aag aaa cat cag aac aca gga           1126
Ala Glu Glu Ala Met Gln Lys Lys His Gln Asn Thr Gly
310                 315                 320 cct gcc ctt gag caa gag gac aag acc agc aag gtg gct           1165
Pro Ala Leu Glu Gln Glu Asp Lys Thr Ser Lys Val Ala
            325                 330                 335 cct ggc aca gcc cct ctg ccc aga ctc ggg gcc act cct           1204
Pro Gly Thr Ala Pro Leu Pro Arg Leu Gly Ala Thr Pro
                340                 345 cag gaa tca agc ctc ctg gcc ggg atc tta gcc tca gaa           1243
Gln Glu Ser Ser Leu Leu Ala Gly Ile Leu Ala Ser Glu
    350                 355                 360 ttg aag agc agc tgg gct aaa tca ggg act gga gag gtg           1282
Leu Lys Ser Ser Trp Ala Lys Ser Gly Thr Gly Glu Val
        365                 370 ccc tct gca cct cgg gaa aac cgg acc acc cca gat tgt           1321
Pro Ser Ala Pro Arg Glu Asn Arg Thr Thr Pro Asp Cys
375                 380                 385 gaa cga gca ttc cca gag gag agg cca gag gtg ctg ggc           1360
Glu Arg Ala Phe Pro Glu Glu Arg Pro Glu Val Leu Gly
            390                 395                 400 cag cgg agc act gat gta gtg gac ctg gaa aat gag gag           1399
Gln Arg Ser Thr Asp Val Val Asp Leu Glu Asn Glu Glu
                405                 410
```

-continued

| | |
|---|---|
| cca gac agt gac aat gag tgg cag cac ctg cta gag acc<br>Pro Asp Ser Asp Asn Glu Trp Gln His Leu Leu Glu Thr<br>415                  420                 425 | 1438 |
| act gag cct gtg cct att caa ctg aag gct cct ctc acc<br>Thr Glu Pro Val Pro Ile Gln Leu Lys Ala Pro Leu Thr<br>             430                     435 | 1477 |
| ttg ctg tgt aat cct gac ttc tgc cag cgc atc cag agt<br>Leu Leu Cys Asn Pro Asp Phe Cys Gln Arg Ile Gln Ser<br>440                  445               450 | 1516 |
| cag ctg cat gaa gct gga ggg cag atc ctg aaa ggc atc<br>Gln Leu His Glu Ala Gly Gly Gln Ile Leu Lys Gly Ile<br>             455                  460            465 | 1555 |
| ttg gag ggt gct tcc cac atc ctg cct gca ttc cgg gtc<br>Leu Glu Gly Ala Ser His Ile Leu Pro Ala Phe Arg Val<br>                   470                   475 | 1594 |
| ctg agc agt ctt ctc tcc agc tgc agt gat tct gtt gcc<br>Leu Ser Ser Leu Leu Ser Ser Cys Ser Asp Ser Val Ala<br>480                  485               490 | 1633 |
| ttg tat tcc ttc tgc cgg gag gca ggg ctt cct ggg ctg<br>Leu Tyr Ser Phe Cys Arg Glu Ala Gly Leu Pro Gly Leu<br>             495                  500 | 1672 |
| ctg ctg agt cta ctc agg cac agt cag gag agc aac agc<br>Leu Leu Ser Leu Leu Arg His Ser Gln Glu Ser Asn Ser<br>505                  510               515 | 1711 |
| ctc cag cag caa tct tgg tat ggg acc ttc tta cag gac<br>Leu Gln Gln Gln Ser Trp Tyr Gly Thr Phe Leu Gln Asp<br>             520                  525            530 | 1750 |
| ctg atg gct gtg att cag gcc tac ttt gcc tgt acc ttc<br>Leu Met Ala Val Ile Gln Ala Tyr Phe Ala Cys Thr Phe<br>                   535                   540 | 1789 |
| aat ctg gag agg agc cag aca agt gac agc ctg cag gtg<br>Asn Leu Glu Arg Ser Gln Thr Ser Asp Ser Leu Gln Val<br>545                  550               555 | 1828 |
| ttt cag gag gct gcc aac ctt ttt ctg gac ctg ttg ggg<br>Phe Gln Glu Ala Ala Asn Leu Phe Leu Asp Leu Leu Gly<br>             560                  565 | 1867 |
| aaa ctg ctg gcc caa cca gat gac tct gag cag act ttg<br>Lys Leu Leu Ala Gln Pro Asp Asp Ser Glu Gln Thr Leu<br>570                  575               580 | 1906 |
| cgg agg gac agc ctt atg tgc ttt act gtc ctg tgc gaa<br>Arg Arg Asp Ser Leu Met Cys Phe Thr Val Leu Cys Glu<br>             585                  590            595 | 1945 |
| gcc atg gat ggg aac agc cgg gcc atc tcc aaa gcc ttt<br>Ala Met Asp Gly Asn Ser Arg Ala Ile Ser Lys Ala Phe<br>                   600                  605 | 1984 |
| tac tcc agc ttg ctg acg aca cag cag gtt gtc ttg gat<br>Tyr Ser Ser Leu Leu Thr Thr Gln Gln Val Val Leu Asp<br>610                  615               620 | 2023 |
| ggg ctc ctt cat ggc ttg aca gtt cca cag ctc cct gtc<br>Gly Leu Leu His Gly Leu Thr Val Pro Gln Leu Pro Val<br>             625                  630 | 2062 |
| cac act ccc caa gga gcc ccg caa gtg agc cag cca ctg<br>His Thr Pro Gln Gly Ala Pro Gln Val Ser Gln Pro Leu<br>635                  640               645 | 2101 |
| cga gag cag agt gag gat ata cct gga gcc att tcc tct<br>Arg Glu Gln Ser Glu Asp Ile Pro Gly Ala Ile Ser Ser<br>             650                  655            660 | 2140 |
| gcc ctg gca gcc ata tgc act gct cct gtg gga ctg ccc<br>Ala Leu Ala Ala Ile Cys Thr Ala Pro Val Gly Leu Pro<br>                   665                  670 | 2179 |

```
gac tgc tgg gat gcc aag gag cag gtc tgt tgg cat ttg                    2218
Asp Cys Trp Asp Ala Lys Glu Gln Val Cys Trp His Leu
        675                 680                 685 gca aat cag cta act gaa gac agc agc cag ctc agg cca                    2257
Ala Asn Gln Leu Thr Glu Asp Ser Ser Gln Leu Arg Pro
                690                 695 tcc ctc atc tct ggc ctg cag cat ccc atc ctg tgc ctg                    2296
Ser Leu Ile Ser Gly Leu Gln His Pro Ile Leu Cys Leu
700                 705                 710 cac ctt ctc aag gtt cta tac tcc tgc tgc ctt gtc agt                    2335
His Leu Leu Lys Val Leu Tyr Ser Cys Cys Leu Val Ser
            715                 720                 725 gag ggc ctg tgc cgt ctt ctg ggg cag gag ccc ctg gcc                    2374
Glu Gly Leu Cys Arg Leu Leu Gly Gln Glu Pro Leu Ala
                730                 735 ttg gaa tcc ctg ttt atg ttg att cag ggc aag gta aaa                    2413
Leu Glu Ser Leu Phe Met Leu Ile Gln Gly Lys Val Lys
        740                 745                 750 gta gta gat tgg gaa gag tct act gaa gtg aca ctc tac                    2452
Val Val Asp Trp Glu Glu Ser Thr Glu Val Thr Leu Tyr
                755                 760 ttc ctc tcc ctt ctt gtc ttt cgg ctc caa aac ctg cct                    2491
Phe Leu Ser Leu Leu Val Phe Arg Leu Gln Asn Leu Pro
765                 770                 775 tgt gga atg gag aag cta ggc agt gac gtt gct act ctc                    2530
Cys Gly Met Glu Lys Leu Gly Ser Asp Val Ala Thr Leu
            780                 785                 790 ttt acc cat tcg cat gtc gtc tct ctt gtg agt gca gca                    2569
Phe Thr His Ser His Val Val Ser Leu Val Ser Ala Ala
                795                 800 gcc tgt cta ttg gga cag ctt ggt cag caa ggg gtg acc                    2608
Ala Cys Leu Leu Gly Gln Leu Gly Gln Gln Gly Val Thr
        805                 810                 815 ttt gac ctc cag ccc atg gaa tgg atg gct gca gcc aca                    2647
Phe Asp Leu Gln Pro Met Glu Trp Met Ala Ala Ala Thr
                820                 825 cat gcc ttg tct gcc cct gca gag gtt cgg ttg act cca                    2686
His Ala Leu Ser Ala Pro Ala Glu Val Arg Leu Thr Pro
830                 835                 840 cca ggt agt tgt gga ttc tat gat ggc ctc ctt atc ctt                    2725
Pro Gly Ser Cys Gly Phe Tyr Asp Gly Leu Leu Ile Leu
            845                 850                 855 ctg ttg cag ctc ctc act gag cag ggg aag gct agc cta                    2764
Leu Leu Gln Leu Leu Thr Glu Gln Gly Lys Ala Ser Leu
                860                 865 atc agg gat atg tcc agt tca gaa atg tgg acc gtt ttg                    2803
Ile Arg Asp Met Ser Ser Ser Glu Met Trp Thr Val Leu
870                 875                 880 tgg cac cgc ttc tcc atg gtc ctg agg ctc ccc gag gag                    2842
Trp His Arg Phe Ser Met Val Leu Arg Leu Pro Glu Glu
            885                 890 gca tct gca cag gaa ggg gag ctt tcg cta tcc agt cca                    2881
Ala Ser Ala Gln Glu Gly Glu Leu Ser Leu Ser Ser Pro
895                 900                 905 cca agc cct gag cca gac tgg aca ctg att tct ccc cag                    2920
Pro Ser Pro Glu Pro Asp Trp Thr Leu Ile Ser Pro Gln
                910                 915                 920 ggc atg gca gcc ctg ctg agc ctg gcc atg gcc acc ttt                    2959
Gly Met Ala Ala Leu Leu Ser Leu Ala Met Ala Thr Phe
```

-continued

|  |  |
|---|---|
| acc cag gag ccc cag tta tgc ctg agc tgc ctg tcc cag<br>Thr Gln Glu Pro Gln Leu Cys Leu Ser Cys Leu Ser Gln<br>  935                          940                        945 | 2998 |
| cat gga agt atc ctc atg tcc atc ctg aag cat ctg ctt<br>His Gly Ser Ile Leu Met Ser Ile Leu Lys His Leu Leu<br>                  950                        955 | 3037 |
| tgc ccc agc ttc ctg aat caa ctg cgc cag gcg cct cat<br>Cys Pro Ser Phe Leu Asn Gln Leu Arg Gln Ala Pro His<br>960                        965                        970 | 3076 |
| ggg tct gag ttt ctc cct gtc gtg gtg ctc tct gtc tgc<br>Gly Ser Glu Phe Leu Pro Val Val Val Leu Ser Val Cys<br>                  975                        980                        985 | 3115 |
| cag ctc ctt tgc ttc ccc ttt gcg ctg gac atg gat gct<br>Gln Leu Leu Cys Phe Pro Phe Ala Leu Asp Met Asp Ala<br>                        990                        995 | 3154 |
| gac ctc ctt ata gtt gtc ttg gcc gac ctc agg gac tca<br>Asp Leu Leu Ile Val Val Leu Ala Asp Leu Arg Asp Ser<br>1000                       1005                      1010 | 3193 |
| gaa gtt gca gcc cat ctg ctg cag gtc tgc tgc tac cat<br>Glu Val Ala Ala His Leu Leu Gln Val Cys Cys Tyr His<br>                1015                      1020 | 3232 |
| ctt ccg ttg atg caa gtg gag ctg ccc atc agc ctt ctc<br>Leu Pro Leu Met Gln Val Glu Leu Pro Ile Ser Leu Leu<br>1025                       1030                      1035 | 3271 |
| aca cgc ctg gcc ctc atg gat ccc acc tct ctc aac cag<br>Thr Arg Leu Ala Leu Met Asp Pro Thr Ser Leu Asn Gln<br>                1040                      1045                      1050 | 3310 |
| ttt gtg aac aca gtg tct gcc tcc cct aga acc atc gtc<br>Phe Val Asn Thr Val Ser Ala Ser Pro Arg Thr Ile Val<br>                        1055                      1060 | 3349 |
| tcg ttt ctc tca gtt gcc ctc ctg agt gac cag cca ctg<br>Ser Phe Leu Ser Val Ala Leu Leu Ser Asp Gln Pro Leu<br>                1065                      1070                      1075 | 3388 |
| ttg acc tcc gac ctt ctc tct ctg gcc cat act gcc<br>Leu Thr Ser Asp Leu Leu Ser Leu Leu Ala His Thr Ala<br>                        1080                      1085 | 3427 |
| agg gtc ctg tct ccc agc cac ttg tcc ttt atc caa gag<br>Arg Val Leu Ser Pro Ser His Leu Ser Phe Ile Gln Glu<br>1090                       1095                      1100 | 3466 |
| ctt ctg gct ggc tct gat gaa tcc tat cgg ccc ctg cgc<br>Leu Leu Ala Gly Ser Asp Glu Ser Tyr Arg Pro Leu Arg<br>                1105                      1110                      1115 | 3505 |
| agc ctc ctg ggc cac cca gag aat tct gtg cgg gca cac<br>Ser Leu Leu Gly His Pro Glu Asn Ser Val Arg Ala His<br>                        1120                      1125 | 3544 |
| act tat agg ctc ctg gga cac ttg ctc caa cac agc atg<br>Thr Tyr Arg Leu Leu Gly His Leu Leu Gln His Ser Met<br>1130                       1135                      1140 | 3583 |
| gcc ctg cgt ggg gca ctg cag agc cag tct gga ctg ctc<br>Ala Leu Arg Gly Ala Leu Gln Ser Gln Ser Gly Leu Leu<br>                1145                      1150 | 3622 |
| agc ctt ctg ctg ctt ggg ctt gga gac aag gat cct gtt<br>Ser Leu Leu Leu Leu Gly Leu Gly Asp Lys Asp Pro Val<br>1155                       1160                      1165 | 3661 |
| gtg cgg tgc agt gcc agc ttt gct gtg ggc aat gca gcc<br>Val Arg Cys Ser Ala Ser Phe Ala Val Gly Asn Ala Ala<br>                1170                      1175                      1180 | 3700 |
| tac cag gct ggt cct ctg gga cct gcc ctg gca gct gca | 3739 |

```
                                                                 -continued

Tyr Gln Ala Gly Pro Leu Gly Pro Ala Leu Ala Ala Ala
            1185                1190 gtg ccc agt atg acc cag ctg ctt gga gat cct cag gct              3778
Val Pro Ser Met Thr Gln Leu Leu Gly Asp Pro Gln Ala
 1195            1200                1205 ggt atc cgg cgc aat gtt gca tca gct ctg ggc aac ttg              3817
Gly Ile Arg Arg Asn Val Ala Ser Ala Leu Gly Asn Leu
        1210                1215 gga cct gaa ggt ttg gga gag gag ctg tta cag tgc gaa              3856
Gly Pro Glu Gly Leu Gly Glu Glu Leu Leu Gln Cys Glu
1220            1225                1230 gta ccc cag cgg ctc cta gaa atg gca tgt gga gac ccc              3895
Val Pro Gln Arg Leu Leu Glu Met Ala Cys Gly Asp Pro
    1235                1240                1245 cag cca aat gtg aag gag gct gcc ctc att gcc ctc cgg              3934
Gln Pro Asn Val Lys Glu Ala Ala Leu Ile Ala Leu Arg
            1250                1255 agc ctg caa cag gag cct ggc atc cat cag gta ctg gtg              3973
Ser Leu Gln Gln Glu Pro Gly Ile His Gln Val Leu Val
 1260            1265                1270 tcc ctg ggt gcc agt gag aaa cta tcc ttg ctc tct ctg              4012
Ser Leu Gly Ala Ser Glu Lys Leu Ser Leu Leu Ser Leu
        1275                1280 ggg aat cag tca ctg cca cac agc agt cct agg cct gcc              4051
Gly Asn Gln Ser Leu Pro His Ser Ser Pro Arg Pro Ala
1285            1290                1295 tct gcc aaa cac tgc agg aaa ctc att cac ctc ctg agg              4090
Ser Ala Lys His Cys Arg Lys Leu Ile His Leu Leu Arg
    1300                1305                1310 cca gcc cat agc atg tgatt ccagattcct gcggtccagc                  4130
Pro Ala His Ser Met
             1315 ctccaactttt ggtgccagct ctttcttatn taatacacaa gcgccaaytc          4180
aactgagagc taaagagact agaaaagaga taagctgcca actcaactga           4230
gaacaggaaa ctngaagaga tttatatata aagcttcttc cttctcccag           4280
atgcaggatg ttttcaacca gtaaattta ttgctgttgg tgccagagaa            4330
gagtcccttt cttctctaca tccagggcc nttttctcca ataatgtgcc            4380
tttaactcta gggacctgcc tcacggacct tagggaaaaa cctcaacctg           4430
aaagatctct tcctttctgg agctccttta atcttcccag caggttttg            4480 ccttagacgt gctggcccca ggacagtgat gaagacagag cctgtctcag           4530
ctctaggctg tggggatcaa tgccatcagt ccctgttatt gagggattat           4580
cccttagcca acattccat ctgtgggtgg gcgtggagag tgtatctttt            4630 tttgggggtgt gtgtgtatat gtgtgtgtgt atgtgtgtgt gtgtttaata          4680
gttctgtttg taaactcttt taataaaagt tgtgcctcac catacttgaa           4730
gctcccagga caagggttga gaggctcaac ccctctttca gcttctatgt           4780
ggtgttggag gtgctggtat cgtgttcaca caaaaaaaaa aaaaaaaaa            4830 aaaaaaaaaa aaaaaaaaa aaaaaaaaa aaaaaaaaa aaaaaaaaaa              4880

<210> SEQ ID NO 2
<211> LENGTH: 1315
<212> TYPE: PRT
<213> ORGANISM: Homo sapiens
```

-continued

```
<400> SEQUENCE: 2

Met Glu Lys Tyr His Val Leu Glu Met Ile Gly Gly Ser Phe
 1               5                  10                  15

Gly Arg Val Tyr Lys Gly Arg Lys Tyr Ser Ala Gln Val Val
                20                  25                  30

Ala Leu Lys Phe Ile Pro Lys Leu Gly Arg Ser Glu Lys Glu Leu
                35                  40                  45

Arg Asn Leu Gln Arg Glu Ile Glu Ile Met Arg Gly Leu Arg His
                50                  55                  60

Pro Asn Ile Val His Met Leu Asp Ser Phe Glu Thr Asp Lys Glu
                65                  70                  75

Val Val Val Val Thr Asp Tyr Ala Glu Gly Glu Leu Phe Gln Ile
                80                  85                  90

Leu Glu Asp Asp Gly Lys Leu Pro Glu Asp Gln Val Gln Ala Ile
                95                  100                 105

Ala Ala Gln Leu Val Ser Ala Leu Tyr Tyr Leu His Ser His Arg
                110                 115                 120

Ile Leu His Arg Asp Met Lys Pro Gln Asn Ile Leu Leu Ala Lys
                125                 130                 135

Gly Gly Gly Ile Lys Leu Cys Asp Phe Gly Phe Ala Arg Ala Met
                140                 145                 150

Ser Thr Asn Thr Met Val Leu Thr Ser Ile Lys Gly Thr Pro Leu
                155                 160                 165

Tyr Met Ser Pro Glu Leu Val Glu Glu Arg Pro Tyr Asp His Thr
                170                 175                 180

Ala Asp Leu Trp Ser Val Gly Cys Ile Leu Tyr Glu Leu Ala Val
                185                 190                 195

Gly Thr Pro Pro Phe Tyr Ala Thr Ser Ile Phe Gln Leu Val Ser
                200                 205                 210

Leu Ile Leu Lys Asp Pro Val Arg Trp Pro Ser Thr Ile Ser Pro
                215                 220                 225

Cys Phe Lys Asn Phe Leu Gln Gly Leu Leu Thr Lys Asp Pro Arg
                230                 235                 240

Gln Arg Leu Ser Trp Pro Asp Leu Leu Tyr His Pro Phe Ile Ala
                245                 250                 255

Gly His Val Thr Ile Ile Thr Glu Pro Ala Gly Pro Asp Leu Gly
                260                 265                 270

Thr Pro Phe Thr Ser Arg Leu Pro Pro Glu Leu Gln Val Leu Lys
                275                 280                 285

Asp Glu Gln Ala His Arg Leu Ala Pro Lys Gly Asn Gln Ser Arg
                290                 295                 300

Ile Leu Thr Gln Ala Tyr Lys Arg Met Ala Glu Glu Ala Met Gln
                305                 310                 315

Lys Lys His Gln Asn Thr Gly Pro Ala Leu Glu Gln Glu Asp Lys
                320                 325                 330

Thr Ser Lys Val Ala Pro Gly Thr Ala Pro Leu Pro Arg Leu Gly
                335                 340                 345

Ala Thr Pro Gln Glu Ser Ser Leu Leu Ala Gly Ile Leu Ala Ser
                350                 355                 360

Glu Leu Lys Ser Ser Trp Ala Lys Ser Gly Thr Gly Glu Val Pro
                365                 370                 375

Ser Ala Pro Arg Glu Asn Arg Thr Thr Pro Asp Cys Glu Arg Ala
                380                 385                 390
```

-continued

```
Phe Pro Glu Glu Arg Pro Glu Val Leu Gly Gln Arg Ser Thr Asp
            395                 400                 405
Val Val Asp Leu Glu Asn Glu Pro Asp Ser Asp Asn Glu Trp
        410                 415                 420
Gln His Leu Leu Glu Thr Thr Glu Pro Val Pro Ile Gln Leu Lys
            425                 430                 435
Ala Pro Leu Thr Leu Leu Cys Asn Pro Asp Phe Cys Gln Arg Ile
            440                 445                 450
Gln Ser Gln Leu His Glu Ala Gly Gly Gln Ile Leu Lys Gly Ile
            455                 460                 465
Leu Glu Gly Ala Ser His Ile Leu Pro Ala Phe Arg Val Leu Ser
            470                 475                 480
Ser Leu Leu Ser Ser Cys Ser Asp Ser Val Ala Leu Tyr Ser Phe
            485                 490                 495
Cys Arg Glu Ala Gly Leu Pro Gly Leu Leu Leu Ser Leu Leu Arg
            500                 505                 510
His Ser Gln Glu Ser Asn Ser Leu Gln Gln Gln Ser Trp Tyr Gly
            515                 520                 525
Thr Phe Leu Gln Asp Leu Met Ala Val Ile Gln Ala Tyr Phe Ala
            530                 535                 540
Cys Thr Phe Asn Leu Glu Arg Ser Gln Thr Ser Asp Ser Leu Gln
            545                 550                 555
Val Phe Gln Glu Ala Ala Asn Leu Phe Leu Asp Leu Leu Gly Lys
            560                 565                 570
Leu Leu Ala Gln Pro Asp Asp Ser Glu Gln Thr Leu Arg Arg Asp
            575                 580                 585
Ser Leu Met Cys Phe Thr Val Leu Cys Glu Ala Met Asp Gly Asn
            590                 595                 600
Ser Arg Ala Ile Ser Lys Ala Phe Tyr Ser Ser Leu Leu Thr Thr
            605                 610                 615
Gln Gln Val Val Leu Asp Gly Leu Leu His Gly Leu Thr Val Pro
            620                 625                 630
Gln Leu Pro Val His Thr Pro Gln Gly Ala Pro Gln Val Ser Gln
            635                 640                 645
Pro Leu Arg Glu Gln Ser Glu Asp Ile Pro Gly Ala Ile Ser Ser
            650                 655                 660
Ala Leu Ala Ala Ile Cys Thr Ala Pro Val Gly Leu Pro Asp Cys
            665                 670                 675
Trp Asp Ala Lys Glu Gln Val Cys Trp His Leu Ala Asn Gln Leu
            680                 685                 690
Thr Glu Asp Ser Ser Gln Leu Arg Pro Ser Leu Ile Ser Gly Leu
            695                 700                 705
Gln His Pro Ile Leu Cys Leu His Leu Leu Lys Val Leu Tyr Ser
            710                 715                 720
Cys Cys Leu Val Ser Glu Gly Leu Cys Arg Leu Leu Gly Gln Glu
            725                 730                 735
Pro Leu Ala Leu Glu Ser Leu Phe Met Leu Ile Gln Gly Lys Val
            740                 745                 750
Lys Val Val Asp Trp Glu Glu Ser Thr Glu Val Thr Leu Tyr Phe
            755                 760                 765
Leu Ser Leu Leu Val Phe Arg Leu Gln Asn Leu Pro Cys Gly Met
            770                 775                 780
```

-continued

```
Glu Lys Leu Gly Ser Asp Val Ala Thr Leu Phe Thr His Ser His
            785                 790                 795
Val Val Ser Leu Val Ser Ala Ala Cys Leu Leu Gly Gln Leu
        800                 805                 810
Gly Gln Gln Gly Val Thr Phe Asp Leu Gln Pro Met Glu Trp Met
            815                 820                 825
Ala Ala Ala Thr His Ala Leu Ser Ala Pro Ala Glu Val Arg Leu
            830                 835                 840
Thr Pro Pro Gly Ser Cys Gly Phe Tyr Asp Gly Leu Leu Ile Leu
            845                 850                 855
Leu Leu Gln Leu Leu Thr Glu Gln Gly Lys Ala Ser Leu Ile Arg
            860                 865                 870
Asp Met Ser Ser Glu Met Trp Thr Val Leu Trp His Arg Phe
        875                 880                 885
Ser Met Val Leu Arg Leu Pro Glu Glu Ala Ser Ala Gln Glu Gly
            890                 895                 900
Glu Leu Ser Leu Ser Ser Pro Ser Pro Glu Pro Asp Trp Thr
        905                 910                 915
Leu Ile Ser Pro Gln Gly Met Ala Ala Leu Leu Ser Leu Ala Met
            920                 925                 930
Ala Thr Phe Thr Gln Glu Pro Gln Leu Cys Leu Ser Cys Leu Ser
            935                 940                 945
Gln His Gly Ser Ile Leu Met Ser Ile Leu Lys His Leu Leu Cys
            950                 955                 960
Pro Ser Phe Leu Asn Gln Leu Arg Gln Ala Pro His Gly Ser Glu
            965                 970                 975
Phe Leu Pro Val Val Leu Ser Val Cys Gln Leu Leu Cys Phe
        980                 985                 990
Pro Phe Ala Leu Asp Met Asp Ala Asp Leu Leu Ile Val Val Leu
            995                 1000                1005
Ala Asp Leu Arg Asp Ser Glu Val Ala Ala His Leu Leu Gln Val
            1010                1015                1020
Cys Cys Tyr His Leu Pro Leu Met Gln Val Glu Leu Pro Ile Ser
            1025                1030                1035
Leu Leu Thr Arg Leu Ala Leu Met Asp Pro Thr Ser Leu Asn Gln
            1040                1045                1050
Phe Val Asn Thr Val Ser Ala Ser Pro Arg Thr Ile Val Ser Phe
            1055                1060                1065
Leu Ser Val Ala Leu Leu Ser Asp Gln Pro Leu Leu Thr Ser Asp
            1070                1075                1080
Leu Leu Ser Leu Leu Ala His Thr Ala Arg Val Leu Ser Pro Ser
            1085                1090                1095
His Leu Ser Phe Ile Gln Glu Leu Leu Ala Gly Ser Asp Glu Ser
            1100                1105                1110
Tyr Arg Pro Leu Arg Ser Leu Leu Gly His Pro Glu Asn Ser Val
            1115                1120                1125
Arg Ala His Thr Tyr Arg Leu Leu Gly His Leu Leu Gln His Ser
            1130                1135                1140
Met Ala Leu Arg Gly Ala Leu Gln Ser Gln Ser Gly Leu Leu Ser
            1145                1150                1155
Leu Leu Leu Leu Gly Leu Gly Asp Lys Asp Pro Val Val Arg Cys
            1160                1165                1170
Ser Ala Ser Phe Ala Val Gly Asn Ala Ala Tyr Gln Ala Gly Pro
```

```
                1175                1180                1185
Leu Gly Pro Ala Leu Ala Ala Val Pro Ser Met Thr Gln Leu
            1190                1195                1200

Leu Gly Asp Pro Gln Ala Gly Ile Arg Arg Asn Val Ala Ser Ala
            1205                1210                1215

Leu Gly Asn Leu Gly Pro Glu Gly Leu Gly Glu Glu Leu Leu Gln
            1220                1225                1230

Cys Glu Val Pro Gln Arg Leu Leu Glu Met Ala Cys Gly Asp Pro
            1235                1240                1245

Gln Pro Asn Val Lys Glu Ala Ala Leu Ile Ala Leu Arg Ser Leu
            1250                1255                1260

Gln Gln Glu Pro Gly Ile His Gln Val Leu Val Ser Leu Gly Ala
            1265                1270                1275

Ser Glu Lys Leu Ser Leu Leu Ser Leu Gly Asn Gln Ser Leu Pro
            1280                1285                1290

His Ser Ser Pro Arg Pro Ala Ser Ala Lys His Cys Arg Lys Leu
            1295                1300                1305

Ile His Leu Leu Arg Pro Ala His Ser Met
            1310                1315

<210> SEQ ID NO 3
<211> LENGTH: 193
<212> TYPE: DNA
<213> ORGANISM: Homo sapiens

<400> SEQUENCE: 3
cccgggctat gagcaccaat acaatggtgc tgacatccat caaaggcaca          50
ccactctata tgtctccaga gctggtggag gagcgaccat acgaccacac         100
agcggacctc tggtctgttg gctgcatact atatgaactg gcagtaggca         150
cccctccctt ctaatgctac aagcatcttt cagctggtca gcc                193

<210> SEQ ID NO 4
<211> LENGTH: 5125
<212> TYPE: DNA
<213> ORGANISM: Homo sapiens

<400> SEQUENCE: 4
cccacgcgtc cgcccacgcg tccggggcgt cccagatgtt gtggaactgt          50
ccctggatct atagctcttc accgtctcta ctttcttcct tctaagagat         100
cctgaaacct ctgtc   atg gaa aag tac cac gtg ttg gag           139
                Met Glu Lys Tyr His Val Leu Glu
                 1               5 atg att gga gaa ggc tct ttt ggg agg gtg tac aag ggt           178
Met Ile Gly Glu Gly Ser Phe Gly Arg Val Tyr Lys Gly
    10              15                  20 cga aga aaa tac agt gct cag gtc gtg gcc ctg aag ttc           217
Arg Arg Lys Tyr Ser Ala Gln Val Val Ala Leu Lys Phe
        25                  30 atc cca aaa ttg ggg cgc tca gag aag gag ctg agg aat           256
Ile Pro Lys Leu Gly Arg Ser Glu Lys Glu Leu Arg Asn
 35              40                  45 ttg caa cga gag att gaa ata atg cgg ggt ctg cgg cat           295
Leu Gln Arg Glu Ile Glu Ile Met Arg Gly Leu Arg His
        50                  55                  60 ccc aac att gtg cat atg ctt gac agc ttt gaa act gat           334
Pro Asn Ile Val His Met Leu Asp Ser Phe Glu Thr Asp
```

```
                  65                      70
aaa gag gtg gtg gtg gtg aca gac tat gct gag gga gag                    373
Lys Glu Val Val Val Val Thr Asp Tyr Ala Glu Gly Glu
         75                      80                  85 ctc ttt cag atc cta gaa gat gac gga aaa ctt cct gaa                    412
Leu Phe Gln Ile Leu Glu Asp Asp Gly Lys Leu Pro Glu
                 90                      95 gac cag gtt cag gcc att gct gcc cag ttg gtg tca gcc                    451
Asp Gln Val Gln Ala Ile Ala Ala Gln Leu Val Ser Ala
100                     105                     110 ctg tac tat ctg cat tcc cac cgc atc cta cac cga gat                    490
Leu Tyr Tyr Leu His Ser His Arg Ile Leu His Arg Asp
            115                     120                     125 atg aag cct cag aac atc ctc ctc gcc aag ggt ggt ggc                    529
Met Lys Pro Gln Asn Ile Leu Leu Ala Lys Gly Gly Gly
                    130                     135 atc aag ctc tgt gac ttt gga ttt gcc cgg gct atg agc                    568
Ile Lys Leu Cys Asp Phe Gly Phe Ala Arg Ala Met Ser
        140                     145                     150 acc aat aca atg gtg ctg aca tcc atc aaa ggc aca cca                    607
Thr Asn Thr Met Val Leu Thr Ser Ile Lys Gly Thr Pro
                155                     160 ctc tat atg tct cca gag ctg gtg gag gag cga cca tac                    646
Leu Tyr Met Ser Pro Glu Leu Val Glu Glu Arg Pro Tyr
165                     170                     175 gac cac aca gcg gac ctc tgg tct gtt ggc tgc ata cta                    685
Asp His Thr Ala Asp Leu Trp Ser Val Gly Cys Ile Leu
            180                     185                     190 tat gaa ctg gca gta ggc acc cct ccc ttc tat gct aca                    724
Tyr Glu Leu Ala Val Gly Thr Pro Pro Phe Tyr Ala Thr
                    195                     200 agc atc ttt cag ctg gtc agc ctc att ctc aag gac cct                    763
Ser Ile Phe Gln Leu Val Ser Leu Ile Leu Lys Asp Pro
        205                     210                     215 gtg cgc tgg ccc tca acc atc agt ccc tgc ttt aag aac                    802
Val Arg Trp Pro Ser Thr Ile Ser Pro Cys Phe Lys Asn
                220                     225 ttc ctg cag gga ctg ctc acc aaa gac cca cgg cag cga                    841
Phe Leu Gln Gly Leu Leu Thr Lys Asp Pro Arg Gln Arg
230                     235                     240 ctg tcc tgg cca gac ctc tta tat cac ccc ttt att gct                    880
Leu Ser Trp Pro Asp Leu Leu Tyr His Pro Phe Ile Ala
            245                     250                     255 ggt cat gtc acc ata ata act gag cca gca ggc cca gat                    919
Gly His Val Thr Ile Ile Thr Glu Pro Ala Gly Pro Asp
                    260                     265 ttg ggg acc cca ttc acc agc cgc cta ccc cca gaa ctt                    958
Leu Gly Thr Pro Phe Thr Ser Arg Leu Pro Pro Glu Leu
        270                     275                     280 cag gtc cta aag gac gaa cag gcc cat cgg ttg gcc ccc                    997
Gln Val Leu Lys Asp Glu Gln Ala His Arg Leu Ala Pro
                285                     290 aag ggt aat cag tct cgc atc ttg act cag gcc tat aaa                    1036
Lys Gly Asn Gln Ser Arg Ile Leu Thr Gln Ala Tyr Lys
295                     300                     305 cgc atg gct gag gag gcc atg cag aag aaa cat cag aac                    1075
Arg Met Ala Glu Glu Ala Met Gln Lys Lys His Gln Asn
            310                     315                     320 aca gga cct gcc ctt gag caa gag gac aag acc agc aag                    1114
```

```
Thr Gly Pro Ala Leu Glu Gln Glu Asp Lys Thr Ser Lys
            325                 330 gtg gct cct ggc aca gcc cct ctg ccc aga ctc ggg gcc        1153
Val Ala Pro Gly Thr Ala Pro Leu Pro Arg Leu Gly Ala
335             340                 345 act cct cag gaa tca agc ctc ctg gcc ggg atc tta gcc        1192
Thr Pro Gln Glu Ser Ser Leu Leu Ala Gly Ile Leu Ala
        350                 355 tca gaa ttg aag agc agc tgg gct aaa tca ggg act gga        1231
Ser Glu Leu Lys Ser Ser Trp Ala Lys Ser Gly Thr Gly
360             365                 370 gag gtg ccc tct gca cct cgg gaa aac cgg acc acc cca        1270
Glu Val Pro Ser Ala Pro Arg Glu Asn Arg Thr Thr Pro
        375                 380                 385 gat tgt gaa cga gca ttc cca gag gag agg cca gag gtg        1309
Asp Cys Glu Arg Ala Phe Pro Glu Glu Arg Pro Glu Val
                390                 395 ctg ggc cag cgg agc act gat gta gtg gac ctg gaa aat        1348
Leu Gly Gln Arg Ser Thr Asp Val Val Asp Leu Glu Asn
        400                 405                 410 gag gag cca gac agt gac aat gag tgg cag cac ctg cta        1387
Glu Glu Pro Asp Ser Asp Asn Glu Trp Gln His Leu Leu
                415                 420 gag acc act gag cct gtg cct att caa ctg aag gct cct        1426
Glu Thr Thr Glu Pro Val Pro Ile Gln Leu Lys Ala Pro
425                 430                 435 ctc acc ttg ctg tgt aat cct gac ttc tgc cag cgc atc        1465
Leu Thr Leu Leu Cys Asn Pro Asp Phe Cys Gln Arg Ile
        440                 445                 450 cag agt cag ctg cat gaa gct gga ggg cag atc ctg aaa        1504
Gln Ser Gln Leu His Glu Ala Gly Gly Gln Ile Leu Lys
                455                 460 ggc atc ttg gag ggt gct tcc cac atc ctg cct gca ttc        1543
Gly Ile Leu Glu Gly Ala Ser His Ile Leu Pro Ala Phe
465                 470                 475 cgg gtc ctg agc agt ctt ctc tcc agc tgc agt gat tct        1582
Arg Val Leu Ser Ser Leu Leu Ser Ser Cys Ser Asp Ser
        480                 485 gtt gcc ttg tat tcc ttc tgc cgg gag gca ggg ctt cct        1621
Val Ala Leu Tyr Ser Phe Cys Arg Glu Ala Gly Leu Pro
490                 495                 500 ggg ctg ctg ctg agt cta ctc agg cac agt cag gag agc        1660
Gly Leu Leu Leu Ser Leu Leu Arg His Ser Gln Glu Ser
        505                 510                 515 aac agc ctc cag cag caa tct tgg tat ggg acc ttc tta        1699
Asn Ser Leu Gln Gln Gln Ser Trp Tyr Gly Thr Phe Leu
                520                 525 cag gac ctg atg gct gtg att cag gcc tac ttt gcc tgt        1738
Gln Asp Leu Met Ala Val Ile Gln Ala Tyr Phe Ala Cys
        530                 535                 540 acc ttc aat ctg gag agg agc cag aca agt gac agc ctg        1777
Thr Phe Asn Leu Glu Arg Ser Gln Thr Ser Asp Ser Leu
                545                 550 cag gtg ttt cag gag gct gcc aac ctt ttt ctg gac ctg        1816
Gln Val Phe Gln Glu Ala Ala Asn Leu Phe Leu Asp Leu
555                 560                 565 ttg ggg aaa ctg ctg gcc caa cca gat gac tct gag cag        1855
Leu Gly Lys Leu Leu Ala Gln Pro Asp Asp Ser Glu Gln
        570                 575                 580
```

-continued

| | |
|---|---|
| act ttg cag agg gac agc ctt atg tgc ttt act gtc ctg<br>Thr Leu Gln Arg Asp Ser Leu Met Cys Phe Thr Val Leu<br>              585              590 | 1894 |
| tgc gaa gcc atg gat ggg aac agc cgg gcc atc tcc aaa<br>Cys Glu Ala Met Asp Gly Asn Ser Arg Ala Ile Ser Lys<br>595              600              605 | 1933 |
| gcc ttt tac tcc agc ttg ctg acg aca cag cag gtt gtc<br>Ala Phe Tyr Ser Ser Leu Leu Thr Thr Gln Gln Val Val<br>              610              615 | 1972 |
| ttg gat ggg ctc ctt cat ggc ttg aca gtt cca cag ctc<br>Leu Asp Gly Leu Leu His Gly Leu Thr Val Pro Gln Leu<br>620              625              630 | 2011 |
| cct gtc cac act ccc caa ggt aac cag agt gga gaa ggg<br>Pro Val His Thr Pro Gln Gly Asn Gln Ser Gly Glu Gly<br>              635              640              645 | 2050 |
| agg ttc tct t gacttacttg ttgcataggt caggctccgc<br>Arg Phe Ser<br>648 | 2090 |
| tctttctatt gccatcacct agatcgcacc tggcatttag taggtgctca | 2140 |
| ataaataact gtgaactgag agaatgaatg gggatctgag ggaaacaaac | 2190 |
| agacctcatc ctgcattctt cccactccct taggttccct actcctgctg | 2240 |
| ccatgtcggt gagtactggt gctattgtct agggcaagag cctcaggcct | 2290 |
| ttgg      agt tac tct ttg ctt ttc tcc aca gga gcc ccg<br>             Ser Tyr Ser Leu Leu Phe Ser Thr Gly Ala Pro<br>              1              5                      10 | 2327 |
| caa gtg agc cag cca ctg cga gag cag agt gag gat ata<br>Gln Val Ser Gln Pro Leu Arg Glu Gln Ser Glu Asp Ile<br>              15                    20 | 2366 |
| cct gga gcc att tcc tct gcc ctg gca gcc ata tgc act<br>Pro Gly Ala Ile Ser Ser Ala Leu Ala Ala Ile Cys Thr<br>25              30                    35 | 2405 |
| gct cct gtg gga ctg ccc gac tgc tgg gat gcc aag gag<br>Ala Pro Val Gly Leu Pro Asp Cys Trp Asp Ala Lys Glu<br>            40                  45              50 | 2444 |
| cag gtc tgt tgg cat ttg gca aat cag cta act gaa gac<br>Gln Val Cys Trp His Leu Ala Asn Gln Leu Thr Glu Asp<br>              55                    60 | 2483 |
| agc agc cag ctc agg cca tcc ctc atc tct ggc ctg cag<br>Ser Ser Gln Leu Arg Pro Ser Leu Ile Ser Gly Leu Gln<br>65              70                    75 | 2522 |
| cat ccc atc ctg tgc ctg cac ctt ctc aag gtt cta tac<br>His Pro Ile Leu Cys Leu His Leu Leu Lys Val Leu Tyr<br>            80                    85 | 2561 |
| tcc tgc tgc ctt gtc agt gag ggc ctg tgc cgt ctt ctg<br>Ser Cys Cys Leu Val Ser Glu Gly Leu Cys Arg Leu Leu<br>90              95                    100 | 2600 |
| ggg cag gag ccc ctg gcc ttg gaa tcc ctg ttt atg ttg<br>Gly Gln Glu Pro Leu Ala Leu Glu Ser Leu Phe Met Leu<br>              105              110              115 | 2639 |
| att cag ggc aag gta aaa gta gta gat tgg gaa gag tct<br>Ile Gln Gly Lys Val Lys Val Val Asp Trp Glu Glu Ser<br>                    120              125 | 2678 |
| act gaa gtg aca ctc tac ttc ctc tcc ctt ctt gtc ttt<br>Thr Glu Val Thr Leu Tyr Phe Leu Ser Leu Leu Val Phe<br>130              135              140 | 2717 |
| cgg ctc caa aac ctg cct tgt gga atg gag aag cta ggc<br>Arg Leu Gln Asn Leu Pro Cys Gly Met Glu Lys Leu Gly<br>              145              150 | 2756 |

```
agt gac gtt gct act ctc ttt acc cat tcg cat gtc gtc                    2795
Ser Asp Val Ala Thr Leu Phe Thr His Ser His Val Val
155                 160                 165 tct ctt gtg agt gca gca gcc tgt cta ttg gga cag ctt                    2834
Ser Leu Val Ser Ala Ala Ala Cys Leu Leu Gly Gln Leu
        170                 175                 180 ggt cag caa ggg gtg acc ttt gac ctc cag ccc atg gaa                    2873
Gly Gln Gln Gly Val Thr Phe Asp Leu Gln Pro Met Glu
                185                 190 tgg atg gct gca gcc aca cat gcc ttg tct gcc cct gca                    2912
Trp Met Ala Ala Ala Thr His Ala Leu Ser Ala Pro Ala
195                 200                 205 gag gtt cgg ttg act cca cca ggt agt tgt gga ttc tat                    2951
Glu Val Arg Leu Thr Pro Pro Gly Ser Cys Gly Phe Tyr
        210                 215 gat ggc ctc ctt atc ctt ctg ttg cag ctc ctc act gag                    2990
Asp Gly Leu Leu Ile Leu Leu Leu Gln Leu Leu Thr Glu
220                 225                 230 cag ggg aag gct agc cta atc agg gat atg tcc agt tca                    3029
Gln Gly Lys Ala Ser Leu Ile Arg Asp Met Ser Ser Ser
        235                 240                 245 gaa atg tgg acc gtt ttg tgg cac cgc ttc tcc atg gtc                    3068
Glu Met Trp Thr Val Leu Trp His Arg Phe Ser Met Val
                250                 255 ctg agg ctc ccc gag gag gca tct gca cag gaa ggg gag                    3107
Leu Arg Leu Pro Glu Glu Ala Ser Ala Gln Glu Gly Glu
260                 265                 270 ctt tcg cta tcc agt cca cca agc cct gag cca gac tgg                    3146
Leu Ser Leu Ser Ser Pro Pro Ser Pro Glu Pro Asp Trp
        275                 280 aca ctg att tct ccc cag ggc atg gca gcc ctg ctg agc                    3185
Thr Leu Ile Ser Pro Gln Gly Met Ala Ala Leu Leu Ser
285                 290                 295 ctg gcc atg gcc acc ttt acc cag gag ccc cag tta tgc                    3224
Leu Ala Met Ala Thr Phe Thr Gln Glu Pro Gln Leu Cys
        300                 305                 310 ctg agc tgc ctg tcc cag cat gga agt atc ctc atg tcc                    3263
Leu Ser Cys Leu Ser Gln His Gly Ser Ile Leu Met Ser
                315                 320 atc ctg aag cat ctg ctt tgc ccc agc ttc ctg aat caa                    3302
Ile Leu Lys His Leu Leu Cys Pro Ser Phe Leu Asn Gln
325                 330                 335 ctg cgc cag gcg cct cat ggg tct gag ttt ctc cct gtc                    3341
Leu Arg Gln Ala Pro His Gly Ser Glu Phe Leu Pro Val
        340                 345 gtg gtg ctc tct gtc tgc cag ctc ctt tgc ttc ccc ttt                    3380
Val Val Leu Ser Val Cys Gln Leu Leu Cys Phe Pro Phe
350                 355                 360 gcg ctg gac atg gat gct gac ctc ctt ata gtt gtc ttg                    3419
Ala Leu Asp Met Asp Ala Asp Leu Leu Ile Val Val Leu
        365                 370                 375 gcc gac ctc agg gac tca gaa gtt gca gcc cat ctg ctg                    3458
Ala Asp Leu Arg Asp Ser Glu Val Ala Ala His Leu Leu
                380                 385 cag gtc tgc tgc tac cat ctt ccg ttg atg caa gtg gag                    3497
Gln Val Cys Cys Tyr His Leu Pro Leu Met Gln Val Glu
390                 395                 400 ctg ccc atc agc ctt ctc aca cgc ctg gcc ctc atg gat                    3536
Leu Pro Ile Ser Leu Leu Thr Arg Leu Ala Leu Met Asp
```

```
                    405                     410
ccc acc tct ctc aac cag ttt gtg aac aca gtg tct gcc           3575
Pro Thr Ser Leu Asn Gln Phe Val Asn Thr Val Ser Ala
415                     420                 425 tcc cct aga acc atc gtc tcg ttt ctc tca gtt gcc ctc           3614
Ser Pro Arg Thr Ile Val Ser Phe Leu Ser Val Ala Leu
        430                 435                 440 ctg agt gac cag cca ctg ttg acc tcc gac ctt ctc tct           3653
Leu Ser Asp Gln Pro Leu Leu Thr Ser Asp Leu Leu Ser
                445                 450 ctg ctg gcc cat act gcc agg gtc ctg tct ccc agc cac           3692
Leu Leu Ala His Thr Ala Arg Val Leu Ser Pro Ser His
455                 460                 465 ttg tcc ttt atc caa gag ctt ctg gct ggc tct gat gaa           3731
Leu Ser Phe Ile Gln Glu Leu Leu Ala Gly Ser Asp Glu
            470                 475 tcc tat cgg ccc ctg cgc agc ctc ctg ggc cac cca gag           3770
Ser Tyr Arg Pro Leu Arg Ser Leu Leu Gly His Pro Glu
480                 485                 490 aat tct gtg cgg gca cac act tat agg ctc ctg gga cac           3809
Asn Ser Val Arg Ala His Thr Tyr Arg Leu Leu Gly His
        495                 500                 505 ttg ctc caa cac agc atg gcc ctg cgt ggg gca ctg cag           3848
Leu Leu Gln His Ser Met Ala Leu Arg Gly Ala Leu Gln
                510                 515 agc cag tct gga ctg ctc agc ctt ctg ctt ctt ggg ctt           3887
Ser Gln Ser Gly Leu Leu Ser Leu Leu Leu Leu Gly Leu
520                 525                 530 gga gac aag gat cct gtt gtg cgg tgc agt gcc agc ttt           3926
Gly Asp Lys Asp Pro Val Val Arg Cys Ser Ala Ser Phe
            535                 540 gct gtg ggc aat gca gcc tac cag gct ggt cct ctg gga           3965
Ala Val Gly Asn Ala Ala Tyr Gln Ala Gly Pro Leu Gly
545                 550                 555 cct gcc ctg gca gct gca gtg ccc agt atg acc cag ctg           4004
Pro Ala Leu Ala Ala Ala Val Pro Ser Met Thr Gln Leu
                560                 565                 570 ctt gga gat cct cag gct ggt atc cgg cgc aat gtt gca           4043
Leu Gly Asp Pro Gln Ala Gly Ile Arg Arg Asn Val Ala
                575                 580 tca gct ctg ggc aac ttg gga cct gaa ggt ttg gga gag           4082
Ser Ala Leu Gly Asn Leu Gly Pro Glu Gly Leu Gly Glu
585                 590                 595 gag ctg tta cag tgc gaa gta ccc cag cgg ctc cta gaa           4121
Glu Leu Leu Gln Cys Glu Val Pro Gln Arg Leu Leu Glu
            600                 605 atg gca tgt gga gac ccc cag cca aat gtg aag gag gct           4160
Met Ala Cys Gly Asp Pro Gln Pro Asn Val Lys Glu Ala
610                 615                 620 gcc ctc att gcc ctc cgg agc ctg caa cag gag cct ggc           4199
Ala Leu Ile Ala Leu Arg Ser Leu Gln Gln Glu Pro Gly
                625                 630                 635 atc cat cag gta ctg gtg tcc ctg ggt gcc agt gag aaa           4238
Ile His Gln Val Leu Val Ser Leu Gly Ala Ser Glu Lys
                    640                 645 cta tcc ttg ctc tct ctg ggg aat cag tca ctg cca cac           4277
Leu Ser Leu Leu Ser Leu Gly Asn Gln Ser Leu Pro His
650                 655                 660 agc agt cct agg cct gcc tct gcc aaa cac tgc agg aaa           4316
```

-continued

```
Ser Ser Pro Arg Pro Ala Ser Ala Lys His Cys Arg Lys
            665                 670 ctc att cac ctc ctg agg cca gcc cat agc atg t              4350
Leu Ile His Leu Leu Arg Pro Ala His Ser Met
675                 680                 685 gattccagat tcctgcggtc cagcctccaa ctttggttgc cagctctttc      4400
ttattctact acacaagccg ccaactcaac tgagagctaa agagactaga      4450
aaagagataa gctgccaact caactgagaa caagaaacta gaagagattt      4500
atatataaag cttcttcctt ctcccagatg caggatgttt tcaaccagta      4550
aattttattg ctgttggtgc cagagaagag tcctttcttc tctacatcca      4600
ggggcctttt ctccaataat gtgcctttaa ctctagggac ctgcctcacg      4650
gaccttaggg aaaaacctca acctgaaaga tctcttcctt tctggagctc      4700
ctttaatctt cccagcaggt ttttgcctta gacgtgctgg ccccaggaca      4750
gtgatgaaga cagagcctgt ctcagctcta ggctgtgggg atcaatgcca      4800
tcagtccctg ttattgaggg attatccctt agccaacatt cctatctgtg      4850
ggtgggcgtg gagagtgtat cttttttttgg ggtgtgtgtg tatatgtgtg     4900
tgtgtatgtg tgtgtgtgtt taatagttct gtttgtaaac tcttttaata      4950
aaagttgtgc ctcaccatac ttgaagctcc caggacaagg gttgagaggc      5000
tcaacccctc tttcagcttc tatgtggtgt tggaggtgct ggtatcgtgt      5050
tcacacaaaa aaaaaaaaaa aaaaaaaaaa aaaaaaaaaa aaaaaaaaaa      5100
aaaaaaaaaa aaaaaaaaaa aaaaa                                5125

<210> SEQ ID NO 5
<211> LENGTH: 648
<212> TYPE: PRT
<213> ORGANISM: Homo sapiens

<400> SEQUENCE: 5

Met Glu Lys Tyr His Val Leu Glu Met Ile Gly Glu Gly Ser Phe
1               5                   10                  15

Gly Arg Val Tyr Lys Gly Arg Arg Lys Tyr Ser Ala Gln Val Val
                20                  25                  30

Ala Leu Lys Phe Ile Pro Lys Leu Gly Arg Ser Glu Lys Glu Leu
                35                  40                  45

Arg Asn Leu Gln Arg Glu Ile Glu Ile Met Arg Gly Leu Arg His
                50                  55                  60

Pro Asn Ile Val His Met Leu Asp Ser Phe Glu Thr Asp Lys Glu
                65                  70                  75

Val Val Val Val Thr Asp Tyr Ala Glu Gly Glu Leu Phe Gln Ile
                80                  85                  90

Leu Glu Asp Asp Gly Lys Leu Pro Glu Asp Gln Val Gln Ala Ile
                95                  100                 105

Ala Ala Gln Leu Val Ser Ala Leu Tyr Tyr Leu His Ser His Arg
                110                 115                 120

Ile Leu His Arg Asp Met Lys Pro Gln Asn Ile Leu Leu Ala Lys
                125                 130                 135

Gly Gly Gly Ile Lys Leu Cys Asp Phe Gly Phe Ala Arg Ala Met
                140                 145                 150

Ser Thr Asn Thr Met Val Leu Thr Ser Ile Lys Gly Thr Pro Leu
                155                 160                 165
```

-continued

```
Tyr Met Ser Pro Glu Leu Val Glu Arg Pro Tyr Asp His Thr
            170                 175                 180

Ala Asp Leu Trp Ser Val Gly Cys Ile Leu Tyr Glu Leu Ala Val
                185                 190                 195

Gly Thr Pro Pro Phe Tyr Ala Thr Ser Ile Phe Gln Leu Val Ser
                200                 205                 210

Leu Ile Leu Lys Asp Pro Val Arg Trp Pro Ser Thr Ile Ser Pro
                215                 220                 225

Cys Phe Lys Asn Phe Leu Gln Gly Leu Leu Thr Lys Asp Pro Arg
                230                 235                 240

Gln Arg Leu Ser Trp Pro Asp Leu Leu Tyr His Pro Phe Ile Ala
                245                 250                 255

Gly His Val Thr Ile Ile Thr Glu Pro Ala Gly Pro Asp Leu Gly
                260                 265                 270

Thr Pro Phe Thr Ser Arg Leu Pro Pro Glu Leu Gln Val Leu Lys
                275                 280                 285

Asp Glu Gln Ala His Arg Leu Ala Pro Lys Gly Asn Gln Ser Arg
                290                 295                 300

Ile Leu Thr Gln Ala Tyr Lys Arg Met Ala Glu Glu Ala Met Gln
                305                 310                 315

Lys Lys His Gln Asn Thr Gly Pro Ala Leu Glu Gln Glu Asp Lys
                320                 325                 330

Thr Ser Lys Val Ala Pro Gly Thr Ala Pro Leu Pro Arg Leu Gly
                335                 340                 345

Ala Thr Pro Gln Glu Ser Ser Leu Leu Ala Gly Ile Leu Ala Ser
                350                 355                 360

Glu Leu Lys Ser Ser Trp Ala Lys Ser Gly Thr Gly Glu Val Pro
                365                 370                 375

Ser Ala Pro Arg Glu Asn Arg Thr Thr Pro Asp Cys Glu Arg Ala
                380                 385                 390

Phe Pro Glu Glu Arg Pro Glu Val Leu Gly Gln Arg Ser Thr Asp
                395                 400                 405

Val Val Asp Leu Glu Asn Glu Glu Pro Asp Ser Asp Asn Glu Trp
                410                 415                 420

Gln His Leu Leu Glu Thr Thr Glu Pro Val Pro Ile Gln Leu Lys
                425                 430                 435

Ala Pro Leu Thr Leu Leu Cys Asn Pro Asp Phe Cys Gln Arg Ile
                440                 445                 450

Gln Ser Gln Leu His Glu Ala Gly Gly Gln Ile Leu Lys Gly Ile
                455                 460                 465

Leu Glu Gly Ala Ser His Ile Leu Pro Ala Phe Arg Val Leu Ser
                470                 475                 480

Ser Leu Leu Ser Ser Cys Ser Asp Ser Val Ala Leu Tyr Ser Phe
                485                 490                 495

Cys Arg Glu Ala Gly Leu Pro Gly Leu Leu Leu Ser Leu Leu Arg
                500                 505                 510

His Ser Gln Glu Ser Asn Ser Leu Gln Gln Ser Trp Tyr Gly
                515                 520                 525

Thr Phe Leu Gln Asp Leu Met Ala Val Ile Gln Ala Tyr Phe Ala
                530                 535                 540

Cys Thr Phe Asn Leu Glu Arg Ser Gln Thr Ser Asp Ser Leu Gln
                545                 550                 555
```

-continued

| | | | | | | | | | | |
|---|---|---|---|---|---|---|---|---|---|---|
|Val|Phe|Gln|Glu|Ala|Ala|Asn|Leu|Phe|Leu|Asp Leu Leu Gly Lys|
| | | |560| | | |565| | |570|

| | | | | | | | | | | |
|---|---|---|---|---|---|---|---|---|---|---|
|Leu|Leu|Ala|Gln|Pro|Asp|Asp|Ser|Glu|Gln|Thr Leu Gln Arg Asp|
| | | |575| | | |580| | |585|

| | | | | | | | | | | |
|---|---|---|---|---|---|---|---|---|---|---|
|Ser|Leu|Met|Cys|Phe|Thr|Val|Leu|Cys|Glu|Ala Met Asp Gly Asn|
| | | |590| | | |595| | |600|

| | | | | | | | | | | |
|---|---|---|---|---|---|---|---|---|---|---|
|Ser|Arg|Ala|Ile|Ser|Lys|Ala|Phe|Tyr|Ser|Ser Leu Leu Thr Thr|
| | | |605| | | |610| | |615|

| | | | | | | | | | | |
|---|---|---|---|---|---|---|---|---|---|---|
|Gln|Gln|Val|Val|Leu|Asp|Gly|Leu|Leu|His|Gly Leu Thr Val Pro|
| | | |620| | | |625| | |630|

| | | | | | | | | | | |
|---|---|---|---|---|---|---|---|---|---|---|
|Gln|Leu|Pro|Val|His|Thr|Pro|Gln|Gly|Asn|Gln Ser Gly Glu Gly|
| | | |635| | | |640| | |645|

Arg Phe Ser
648

<210> SEQ ID NO 6
<211> LENGTH: 5252
<212> TYPE: DNA
<213> ORGANISM: Homo sapiens

<400> SEQUENCE: 6

```
ggagcttgga gctcctaggc tgggggcgtc ccagatgttg tggaactgtc            50
cctggatcta tagctcttca ccgtctctac tttcttcctt ctaagagatc           100
ctgaaacctc tgtc atg gaa aag tac cac gtg ttg gag atg              141
              Met Glu Lys Tyr His Val Leu Glu Met
                1               5 att gga gaa ggc tct ttt ggg agg gtg tac aag ggt cga              180
Ile Gly Glu Gly Ser Phe Gly Arg Val Tyr Lys Gly Arg
 10              15                  20 aga aaa tac agt gct cag gtc gtg gcc ctg aag ttc atc              219
Arg Lys Tyr Ser Ala Gln Val Val Ala Leu Lys Phe Ile
         25                  30              35 cca aaa ttg ggg cgc tca gag aag gag ctg agg aat ttg              258
Pro Lys Leu Gly Arg Ser Glu Lys Glu Leu Arg Asn Leu
             40                  45 caa cga gag att gaa ata atg cgg ggt ctg cgg cat ccc              297
Gln Arg Glu Ile Glu Ile Met Arg Gly Leu Arg His Pro
 50                  55                  60 aac att gtg cat atg ctt gac agc ttt gaa act gat aaa              336
Asn Ile Val His Met Leu Asp Ser Phe Glu Thr Asp Lys
             65                  70 gag gtg gtg gtg gtg aca gac tat gct gag gga gag ctc              375
Glu Val Val Val Val Thr Asp Tyr Ala Glu Gly Glu Leu
 75                  80                  85 ttt cag atc cta gaa gat gac gga aaa ctt cct gaa gac              414
Phe Gln Ile Leu Glu Asp Asp Gly Lys Leu Pro Glu Asp
             90                  95                 100 cag gtt cag gcc att gct gcc cag ttg gtg tca gcc ctg              453
Gln Val Gln Ala Ile Ala Ala Gln Leu Val Ser Ala Leu
                 105                 110 tac tat ctg cat tcc cac cgc atc cta cac cga gat atg              492
Tyr Tyr Leu His Ser His Arg Ile Leu His Arg Asp Met
 115                 120                 125 aag cct cag aac atc ctc ctc gcc aag ggt ggt ggc atc              531
Lys Pro Gln Asn Ile Leu Leu Ala Lys Gly Gly Gly Ile
             130                 135 aag ctc tgt gac ttt gga ttt gcc cgg gct atg agc acc              570
Lys Leu Cys Asp Phe Gly Phe Ala Arg Ala Met Ser Thr
```

-continued

| | | |
|---|---|---|
| 140 | 145 | 150 | aat aca atg gtg ctg aca tcc atc aaa ggc aca cca ctc        609
Asn Thr Met Val Leu Thr Ser Ile Lys Gly Thr Pro Leu
        155                 160                 165 tat atg tct cca gag ctg gtg gag gag cga cca tac gac        648
Tyr Met Ser Pro Glu Leu Val Glu Glu Arg Pro Tyr Asp
                170                 175 cac aca gcg gac ctc tgg tct gtt ggc tgc ata cta tat        687
His Thr Ala Asp Leu Trp Ser Val Gly Cys Ile Leu Tyr
    180                 185                 190 gaa ctg gca gta ggc acc cct ccc ttc tat gct aca agc        726
Glu Leu Ala Val Gly Thr Pro Pro Phe Tyr Ala Thr Ser
                195                 200 atc ttt cag ctg gtc agc ctc att ctc aag gac cct gtg        765
Ile Phe Gln Leu Val Ser Leu Ile Leu Lys Asp Pro Val
205                 210                 215 cgc tgg ccc tca acc atc agt ccc tgc ttt aag aac ttc        804
Arg Trp Pro Ser Thr Ile Ser Pro Cys Phe Lys Asn Phe
        220                 225                 230 ctg cag gga ctg ctc acc aaa gac cca cgg cag cga ctg        843
Leu Gln Gly Leu Leu Thr Lys Asp Pro Arg Gln Arg Leu
                235                 240 tcc tgg cca gac ctc tta tat cac ccc ttt att gct ggt        882
Ser Trp Pro Asp Leu Leu Tyr His Pro Phe Ile Ala Gly
    245                 250                 255 cat gtc acc ata ata act gag cca gca ggc cca gat ttg        921
His Val Thr Ile Ile Thr Glu Pro Ala Gly Pro Asp Leu
                260                 265 ggg acc cca ttc acc agc cgc cta ccc cca gaa ctt cag        960
Gly Thr Pro Phe Thr Ser Arg Leu Pro Pro Glu Leu Gln
270                 275                 280 gtc cta aag gac gaa cag gcc cat cgg ttg gcc ccc aag        999
Val Leu Lys Asp Glu Gln Ala His Arg Leu Ala Pro Lys
        285                 290                 295 ggt aat cag tct cgc atc ttg act cag gcc tat aaa cgc        1038
Gly Asn Gln Ser Arg Ile Leu Thr Gln Ala Tyr Lys Arg
                300                 305 atg gct gag gag gcc atg cag aag aaa cat cag aac aca        1077
Met Ala Glu Glu Ala Met Gln Lys Lys His Gln Asn Thr
    310                 315                 320 gga cct gcc ctt gag caa gag gac aag acc agc aag gtg        1116
Gly Pro Ala Leu Glu Gln Glu Asp Lys Thr Ser Lys Val
                325                 330 gct cct ggc aca gcc cct ctg ccc aga ctc ggg gcc act        1155
Ala Pro Gly Thr Ala Pro Leu Pro Arg Leu Gly Ala Thr
335                 340                 345 cct cag gaa tca agc ctc ctg gcc ggg atc tta gcc tca        1194
Pro Gln Glu Ser Ser Leu Leu Ala Gly Ile Leu Ala Ser
        350                 355                 360 gaa ttg aag agc agc tgg gct aaa tca ggg act gga gag        1233
Glu Leu Lys Ser Ser Trp Ala Lys Ser Gly Thr Gly Glu
                365                 370 gtg ccc tct gca cct cgg gaa aac cgg acc acc cca gat        1272
Val Pro Ser Ala Pro Arg Glu Asn Arg Thr Thr Pro Asp
    375                 380                 385 tgt gaa cga gca ttc cca gag gag agg cca gag gtg ctg        1311
Cys Glu Arg Ala Phe Pro Glu Glu Arg Pro Glu Val Leu
                390                 395 ggc cag cgg agc act gat gta gtg gac ctg gaa aat gag        1350

```
Gly Gln Arg Ser Thr Asp Val Val Asp Leu Glu Asn Glu
400                 405                 410 gag cca gac agt gac aat gag tgg cag cac ctg cta gag       1389
Glu Pro Asp Ser Asp Asn Glu Trp Gln His Leu Leu Glu
        415                 420                 425 acc act gag cct gtg cct att caa ctg aag gct cct ctc       1428
Thr Thr Glu Pro Val Pro Ile Gln Leu Lys Ala Pro Leu
                430                 435 acc ttg ctg tgt aat cct gac ttc tgc cag cgc atc cag       1467
Thr Leu Leu Cys Asn Pro Asp Phe Cys Gln Arg Ile Gln
440                 445                 450 agt cag ctg cat gaa gct gga ggg cag atc ctg aaa ggc       1506
Ser Gln Leu His Glu Ala Gly Gly Gln Ile Leu Lys Gly
        455                 460 atc ttg gag ggt gct tcc cac atc ctg cct gca ttc cgg       1545
Ile Leu Glu Gly Ala Ser His Ile Leu Pro Ala Phe Arg
465                 470                 475 gtc ctg agc agt ctt ctc tcc agc tgc agt gat tct gtt       1584
Val Leu Ser Ser Leu Leu Ser Ser Cys Ser Asp Ser Val
        480                 485                 490 gcc ttg tat tcc ttc tgc cgg gag gca ggg ctt cct ggg       1623
Ala Leu Tyr Ser Phe Cys Arg Glu Ala Gly Leu Pro Gly
                495                 500 ctg ctg ctg agt cta ctc agg cac agt cag gag agc aac       1662
Leu Leu Leu Ser Leu Leu Arg His Ser Gln Glu Ser Asn
505                 510                 515 agc ctc cag cag caa tct tgg tat ggg acc ttc tta cag       1701
Ser Leu Gln Gln Gln Ser Trp Tyr Gly Thr Phe Leu Gln
        520                 525 gac ctg atg gct gtg att cag gcc tac ttt gcc tgt acc       1740
Asp Leu Met Ala Val Ile Gln Ala Tyr Phe Ala Cys Thr
530                 535                 540 ttc aat ctg gag agg agc cag aca agt gac agc ctg cag       1779
Phe Asn Leu Glu Arg Ser Gln Thr Ser Asp Ser Leu Gln
        545                 550                 555 gtg ttt cag gag gct gcc aac ctt ttt ctg gac ctg ttg       1818
Val Phe Gln Glu Ala Ala Asn Leu Phe Leu Asp Leu Leu
                560                 565 ggg aaa ctg ctg gcc caa cca gat gac tct gag cag act       1857
Gly Lys Leu Leu Ala Gln Pro Asp Asp Ser Glu Gln Thr
570                 575                 580 ttg cgg agg gac agc ctt atg tgc ttt act gtc ctg tgc       1896
Leu Arg Arg Asp Ser Leu Met Cys Phe Thr Val Leu Cys
        585                 590 gaa gcc atg gat ggg aac agc cgg gcc atc tcc aaa gcc       1935
Glu Ala Met Asp Gly Asn Ser Arg Ala Ile Ser Lys Ala
595                 600                 605 ttt tac tcc agc ttg ctg acg aca cag cag gtt gtc ttg       1974
Phe Tyr Ser Ser Leu Leu Thr Thr Gln Gln Val Val Leu
        610                 615                 620 gat ggg ctc ctt cat ggc ttg aca gtt cca cag ctc cct       2013
Asp Gly Leu Leu His Gly Leu Thr Val Pro Gln Leu Pro
                625                 630 gtc cac act ccc caa ggt tcc cta ctc ctg ctg cca tgt       2052
Val His Thr Pro Gln Gly Ser Leu Leu Leu Leu Pro Cys
635                 640                 645 cgg tga g t   actggtgcta ttgtctaggg caagagcctc            2090
Arg Xaa
648
```

-continued

| | |
|---|---|
| aggcctttgg agt tac tct ttg ctt ttc tcc aca gga gcc<br>             Ser Tyr Ser Leu Leu Phe Ser Thr Gly Ala<br>              1               5                 10 | 2130 |
| ccg caa gtg agc cag cca ctg cga gag cag agt gag gat<br>Pro Gln Val Ser Gln Pro Leu Arg Glu Gln Ser Glu Asp<br>               15                      20 | 2169 |
| ata cct gga gcc att tcc tct gcc ctg gca gcc ata tgc<br>Ile Pro Gly Ala Ile Ser Ser Ala Leu Ala Ala Ile Cys<br>    25                    30                   35 | 2208 |
| act gct cct gtg gga ctg ccc gac tgc tgg gat gcc aag<br>Thr Ala Pro Val Gly Leu Pro Asp Cys Trp Asp Ala Lys<br>           40                    45 | 2247 |
| gag cag gtc tgt tgg cat ttg gca aat cag cta act gaa<br>Glu Gln Val Cys Trp His Leu Ala Asn Gln Leu Thr Glu<br>50                   55                   60 | 2286 |
| gac agc agc cag ctc agg cca tcc ctc atc tct ggc ctg<br>Asp Ser Ser Gln Leu Arg Pro Ser Leu Ile Ser Gly Leu<br>        65                    70                  75 | 2325 |
| cag cat ccc atc ctg tgc ctg cac ctt ctc aag gtt cta<br>Gln His Pro Ile Leu Cys Leu His Leu Leu Lys Val Leu<br>                80                    85 | 2364 |
| tac tcc tgc tgc ctt gtc agt gag ggc ctg tgc cgt ctt<br>Tyr Ser Cys Cys Leu Val Ser Glu Gly Leu Cys Arg Leu<br>    90                    95                 100 | 2403 |
| ctg ggg cag gag ccc ctg gcc ttg gaa tcc ctg ttt atg<br>Leu Gly Gln Glu Pro Leu Ala Leu Glu Ser Leu Phe Met<br>               105                 110 | 2442 |
| ttg att cag ggc aag gta aaa gta gta gat tgg gaa gag<br>Leu Ile Gln Gly Lys Val Lys Val Val Asp Trp Glu Glu<br>115                 120                 125 | 2481 |
| tct act gaa gtg aca ctc tac ttc ctc tcc ctt ctt gtc<br>Ser Thr Glu Val Thr Leu Tyr Phe Leu Ser Leu Leu Val<br>         130                 135               140 | 2520 |
| ttt cgg ctc caa aac ctg cct tgt gga atg gag aag cta<br>Phe Arg Leu Gln Asn Leu Pro Cys Gly Met Glu Lys Leu<br>               145                 150 | 2559 |
| ggc agt gac gtt gct act ctc ttt acc cat tcg cat gtc<br>Gly Ser Asp Val Ala Thr Leu Phe Thr His Ser His Val<br>     155                  160               165 | 2598 |
| gtc tct ctt gtg agt gca gca gcc tgt cta ttg gga cag<br>Val Ser Leu Val Ser Ala Ala Ala Cys Leu Leu Gly Gln<br>               170                 175 | 2637 |
| ctt ggt cag caa ggg gtg acc ttt gac ctc cag ccc atg<br>Leu Gly Gln Gln Gly Val Thr Phe Asp Leu Gln Pro Met<br>180                 185                 190 | 2676 |
| gaa tgg atg gct gca gcc aca cat gcc ttg tct gcc cct<br>Glu Trp Met Ala Ala Ala Thr His Ala Leu Ser Ala Pro<br>         195                 200               205 | 2715 |
| gca gag ctc ctc act gag gta cag atg gat ctt ggg atg<br>Ala Glu Leu Leu Thr Glu Val Gln Met Asp Leu Gly Met<br>               210                 215 | 2754 |
| gat ggg aag taaagag agaggaactg ggcattttgg ggagcctctg<br>Asp Gly Lys<br>220 221 | 2800 |
| gaccagagga atgaagaagc aacccacagc cttccctctc aagctactgt | 2850 |
| gcctgtgata gccttggaac ttccccgcct gccctcagta ctgacccttt | 2900 |
| gaaggaaacc attcgctgcg tcccctggga tccagtggga gataaaatga | 2950 |
| attccctggg tttcagcaga catacacatg agttgtgagg tcagagggtt | 3000 |

-continued

```
aaggtttgat aagaaaatga aataagacga cagggaaata ctaggtggga       3050
aagcggaagg aattatttct gggacttcct ttacttgtaa gtcagggaca       3100
ggaatgaata aaagcatttg gattcctgac ttctgtcttt cccccgccc        3150 tctttcactt ttatctctag caggggaagg ctagcctaat cagggatatg       3200
tccagttcag aaatgtggac cgttttgtgg caccgcttct ccatggtcct       3250
gaggctcccc gaggaggcat ctgcacagga aggggagctt tcgctatcca       3300
gtccaccaag ccctgagcca gactggacac tgatttctcc ccagggcatg       3350
gcagccctgc tgagcctggc catggccacc tttacccagg agccccagtt       3400
atgcctgagc tgcctgtccc agcatggaag tatcctcatg tccatcctga       3450
agcatctgct ttgccccagc ttcctgaatc aactgcgcca ggcgcctcat       3500
gggtctgagt ttctccctgt cgtggtgctc tctgtctgcc agctcctttg       3550
cttccccttt gcgctggaca tggatgctga cctccttata ggtgtcttgg       3600
ccgacctcag ggactcagaa gttgcagccc atctgctgca ggtctgctgc       3650
taccatcttc cgttgatgca agtggagctg cccatcagcc ttctcacacg       3700
cctggccctc atggatccca cctctctcaa ccagtttgtg aacacagtgt       3750
ctgcctcccc tagaaccatc gtctcgtttc tctcagttgc cctcctgagt       3800
gaccagccac tgttgacctc cgaccttctc tctctgctgg cccatactgc       3850
cagggtcctg tctcccagcc acttgtcctt tatccaagag cttctggctg       3900
gctctgatga atcctatcgg cccctgcgca gcctcctggg ccacccagag       3950
aattctgtgc gggcacacac ttataggctc ctgggacact tgctccaaca       4000
cagcatggcc ctgcgtgggg cactgcagag ccagtctgga ctgctcagcc       4050
ttctgctgct tgggcttgga gacaaggatc ctgttgtgcg gtgcagtgcc       4100
agctttgctg tgggcaatgc agcctaccag gctggtcctc tgggacctgc       4150
cctggcagct gcagtgccca gtatgaccca gctgcttgga gatcctcagg       4200
ctggtatccg gcgcaatgtt gcatcagctc tgggcaactt gggacctgaa       4250
ggtttgggag aggagctgtt acagtgcgaa gtaccccagc ggctcctaga       4300
aatggcatgt ggagaccccc agccaaatgt gaaggaggct gccctcattg       4350
ccctccggag cctgcaacag gagcctggca tccatcaggt actggtgtcc       4400
ctgggtgcca gtgagaaact atccttgctc tctctgggga atcagtcact       4450
gccacacagc agtcctaggc ctgcctctgc caaacactgc aggaaactca       4500
ttcacctcct gaggccagcc catagcatgt gattccagat tcctgcggtc       4550
cagcctccaa ctttggttgc cagctctttc ttattctact acacaagccg       4600
ccaactcaac tgagagctaa agagactaga aaagagataa gctgccaact       4650
caactgagaa caagaaacta gaagagattt atatataaag cttcttcctt       4700
ctcccagatg caggatgttt tcaaccagta aattttattg ctgttggtgc       4750
cagagaagag tcctttcttc tctacatcca ggggccttt ctccaataat         4800 gtgcctttaa ctctagggac ctgcctcacg gaccttaggg aaaaacctca       4850
acctgaaaga tctcttcctt tctggagctc ctttaatctt cccagcaggt       4900
ttttgcctta gacgtgctgg ccccaggaca gtgatgaaga cagagcctgt       4950
```

-continued

| | |
|---|---|
| ctcagctcta ggctgtgggg atcaatgcca tcagtccctg ttattgaggg | 5000 |
| attatcccctt agccaacatt cctatctgtg ggtgggcgtg gagagtgtat | 5050 |
| cttttttttgg ggtgtgtgtg tatatgtgtg tgtgtatgtg tgtgtgtgtt | 5100 |
| taatagttct gtttgtaaac tcttttaata aaagttgtgc ctcaccatac | 5150 |
| ttgaagctcc caggacaagg gttgagaggc tcaaccccctc tttcagcttc | 5200 |
| tatgtggtgt tggaggtgct ggtatcgtgt tcacacaaaa aaaaaaaaaa | 5250 |
| aa | 5252 |

<210> SEQ ID NO 7
<211> LENGTH: 647
<212> TYPE: PRT
<213> ORGANISM: Homo sapiens

<400> SEQUENCE: 7

```
Met Glu Lys Tyr His Val Leu Glu Met Ile Gly Glu Gly Ser Phe
  1               5                  10                  15

Gly Arg Val Tyr Lys Gly Arg Arg Lys Tyr Ser Ala Gln Val Val
                 20                  25                  30

Ala Leu Lys Phe Ile Pro Lys Leu Gly Arg Ser Glu Lys Glu Leu
                 35                  40                  45

Arg Asn Leu Gln Arg Glu Ile Glu Ile Met Arg Gly Leu Arg His
                 50                  55                  60

Pro Asn Ile Val His Met Leu Asp Ser Phe Glu Thr Asp Lys Glu
                 65                  70                  75

Val Val Val Val Thr Asp Tyr Ala Glu Gly Glu Leu Phe Gln Ile
                 80                  85                  90

Leu Glu Asp Asp Gly Lys Leu Pro Glu Asp Gln Val Gln Ala Ile
                 95                 100                 105

Ala Ala Gln Leu Val Ser Ala Leu Tyr Tyr Leu His Ser His Arg
                110                 115                 120

Ile Leu His Arg Asp Met Lys Pro Gln Asn Ile Leu Leu Ala Lys
                125                 130                 135

Gly Gly Gly Ile Lys Leu Cys Asp Phe Gly Phe Ala Arg Ala Met
                140                 145                 150

Ser Thr Asn Thr Met Val Leu Thr Ser Ile Lys Gly Thr Pro Leu
                155                 160                 165

Tyr Met Ser Pro Glu Leu Val Glu Glu Arg Pro Tyr Asp His Thr
                170                 175                 180

Ala Asp Leu Trp Ser Val Gly Cys Ile Leu Tyr Glu Leu Ala Val
                185                 190                 195

Gly Thr Pro Pro Phe Tyr Ala Thr Ser Ile Phe Gln Leu Val Ser
                200                 205                 210

Leu Ile Leu Lys Asp Pro Val Arg Trp Pro Ser Thr Ile Ser Pro
                215                 220                 225

Cys Phe Lys Asn Phe Leu Gln Gly Leu Leu Thr Lys Asp Pro Arg
                230                 235                 240

Gln Arg Leu Ser Trp Pro Asp Leu Leu Tyr His Pro Phe Ile Ala
                245                 250                 255

Gly His Val Thr Ile Ile Thr Glu Pro Ala Gly Pro Asp Leu Gly
                260                 265                 270

Thr Pro Phe Thr Ser Arg Leu Pro Pro Glu Leu Gln Val Leu Lys
                275                 280                 285
```

```
Asp Glu Gln Ala His Arg Leu Ala Pro Lys Gly Asn Gln Ser Arg
                290                 295                 300

Ile Leu Thr Gln Ala Tyr Lys Arg Met Ala Glu Glu Ala Met Gln
                305                 310                 315

Lys Lys His Gln Asn Thr Gly Pro Ala Leu Glu Gln Glu Asp Lys
                320                 325                 330

Thr Ser Lys Val Ala Pro Gly Thr Ala Pro Leu Pro Arg Leu Gly
                335                 340                 345

Ala Thr Pro Gln Glu Ser Ser Leu Leu Ala Gly Ile Leu Ala Ser
                350                 355                 360

Glu Leu Lys Ser Ser Trp Ala Lys Ser Gly Thr Gly Glu Val Pro
                365                 370                 375

Ser Ala Pro Arg Glu Asn Arg Thr Thr Pro Asp Cys Glu Arg Ala
                380                 385                 390

Phe Pro Glu Glu Arg Pro Glu Val Leu Gly Gln Arg Ser Thr Asp
                395                 400                 405

Val Val Asp Leu Glu Asn Glu Glu Pro Asp Ser Asp Asn Glu Trp
                410                 415                 420

Gln His Leu Leu Glu Thr Thr Glu Pro Val Pro Ile Gln Leu Lys
                425                 430                 435

Ala Pro Leu Thr Leu Leu Cys Asn Pro Asp Phe Cys Gln Arg Ile
                440                 445                 450

Gln Ser Gln Leu His Glu Ala Gly Gly Gln Ile Leu Lys Gly Ile
                455                 460                 465

Leu Glu Gly Ala Ser His Ile Leu Pro Ala Phe Arg Val Leu Ser
                470                 475                 480

Ser Leu Leu Ser Ser Cys Ser Asp Ser Val Ala Leu Tyr Ser Phe
                485                 490                 495

Cys Arg Glu Ala Gly Leu Pro Gly Leu Leu Ser Leu Leu Arg
                500                 505                 510

His Ser Gln Glu Ser Asn Ser Leu Gln Gln Gln Ser Trp Tyr Gly
                515                 520                 525

Thr Phe Leu Gln Asp Leu Met Ala Val Ile Gln Ala Tyr Phe Ala
                530                 535                 540

Cys Thr Phe Asn Leu Glu Arg Ser Gln Thr Ser Asp Ser Leu Gln
                545                 550                 555

Val Phe Gln Glu Ala Ala Asn Leu Phe Leu Asp Leu Leu Gly Lys
                560                 565                 570

Leu Leu Ala Gln Pro Asp Asp Ser Glu Gln Thr Leu Arg Arg Asp
                575                 580                 585

Ser Leu Met Cys Phe Thr Val Leu Cys Glu Ala Met Asp Gly Asn
                590                 595                 600

Ser Arg Ala Ile Ser Lys Ala Phe Tyr Ser Ser Leu Leu Thr Thr
                605                 610                 615

Gln Gln Val Val Leu Asp Gly Leu Leu His Gly Leu Thr Val Pro
                620                 625                 630

Gln Leu Pro Val His Thr Pro Gln Gly Ser Leu Leu Leu Leu Pro
                635                 640                 645

Cys Arg
    647

<210> SEQ ID NO 8
<211> LENGTH: 32
<212> TYPE: DNA
```

<210> SEQ ID NO 9
<211> LENGTH: 23
<212> TYPE: DNA
<213> ORGANISM: artificial sequence
<220> FEATURE:
<223> OTHER INFORMATION: artificial sequence

<400> SEQUENCE: 8
caatacaatg gtgctgacat ccatcaaagg ca                                    32

<210> SEQ ID NO 9
<211> LENGTH: 23
<212> TYPE: DNA
<213> ORGANISM: artificial sequence
<220> FEATURE:
<223> OTHER INFORMATION: artificial sequence

<400> SEQUENCE: 9
gaagggaggg gtgcctactg cca                                              23

<210> SEQ ID NO 10
<211> LENGTH: 38
<212> TYPE: DNA
<213> ORGANISM: artificial sequence
<220> FEATURE:
<223> OTHER INFORMATION: artificial sequence

<400> SEQUENCE: 10
ctccagctct ggagacatat agagtggtgt gcctttga                              38

<210> SEQ ID NO 11
<211> LENGTH: 60
<212> TYPE: DNA
<213> ORGANISM: artificial sequence
<220> FEATURE:
<223> OTHER INFORMATION: artificial sequence

<400> SEQUENCE: 11
ccatcgatgt acccatacga cgtcccagac tacgctgaaa agtaccacgt                 50
gttggagatg                                                             60

<210> SEQ ID NO 12
<211> LENGTH: 32
<212> TYPE: DNA
<213> ORGANISM: artificial sequence
<220> FEATURE:
<223> OTHER INFORMATION: artificial sequence

<400> SEQUENCE: 12
gctctagact aagggcagg tcctgtgttc tg                                     32

<210> SEQ ID NO 13
<211> LENGTH: 21
<212> TYPE: DNA
<213> ORGANISM: artificial sequence
<220> FEATURE:
<223> OTHER INFORMATION: artificial sequence

<400> SEQUENCE: 13
ctgacgacac agcaggttgt c                                                21

<210> SEQ ID NO 14
<211> LENGTH: 21
<212> TYPE: DNA
<213> ORGANISM: artificial sequence
<220> FEATURE:
<223> OTHER INFORMATION: artificial sequence

<400> SEQUENCE: 14

```
cagatgcttc aggatggaca t                                                   21

<210> SEQ ID NO 15
<211> LENGTH: 19
<212> TYPE: DNA
<213> ORGANISM: artificial sequence
<220> FEATURE:
<223> OTHER INFORMATION: artificial sequence

<400> SEQUENCE: 15
agagtagcaa cgtcactgc                                                      19

<210> SEQ ID NO 16
<211> LENGTH: 21
<212> TYPE: DNA
<213> ORGANISM: artificial sequence
<220> FEATURE:
<223> OTHER INFORMATION: artificial sequence

<400> SEQUENCE: 16
cctcactgac aaggcagcag g                                                   21

<210> SEQ ID NO 17
<211> LENGTH: 21
<212> TYPE: DNA
<213> ORGANISM: artificial sequence
<220> FEATURE:
<223> OTHER INFORMATION: artificial sequence

<400> SEQUENCE: 17
cccgaggagg catctgcaca g                                                   21

<210> SEQ ID NO 18
<211> LENGTH: 21
<212> TYPE: DNA
<213> ORGANISM: artificial sequence
<220> FEATURE:
<223> OTHER INFORMATION: artificial sequence

<400> SEQUENCE: 18
cagaacttca ggtcctaaag g                                                   21

<210> SEQ ID NO 19
<211> LENGTH: 32
<212> TYPE: DNA
<213> ORGANISM: artificial sequence
<220> FEATURE:
<223> OTHER INFORMATION: artificial sequence

<400> SEQUENCE: 19
tcgacaagca gggaacaccc aagtagaagc tc                                       32

<210> SEQ ID NO 20
<211> LENGTH: 32
<212> TYPE: DNA
<213> ORGANISM: artificial sequence
<220> FEATURE:
<223> OTHER INFORMATION: artificial sequence

<400> SEQUENCE: 20
tcgacaagca gggaagtggg aagtagaagc tc                                       32

<210> SEQ ID NO 21
<211> LENGTH: 685
<212> TYPE: PRT
```

<213> ORGANISM: Homo sapiens

<400> SEQUENCE: 21

```
Ser Tyr Ser Leu Leu Phe Ser Thr Gly Ala Pro Gln Val Ser Gln
 1               5                  10                  15

Pro Leu Arg Glu Gln Ser Glu Asp Ile Pro Gly Ala Ile Ser Ser
                20                  25                  30

Ala Leu Ala Ala Ile Cys Thr Ala Pro Val Gly Leu Pro Asp Cys
                35                  40                  45

Trp Asp Ala Lys Glu Gln Val Cys Trp His Leu Ala Asn Gln Leu
                50                  55                  60

Thr Glu Asp Ser Ser Gln Leu Arg Pro Ser Leu Ile Ser Gly Leu
                65                  70                  75

Gln His Pro Ile Leu Cys Leu His Leu Leu Lys Val Leu Tyr Ser
                80                  85                  90

Cys Cys Leu Val Ser Glu Gly Leu Cys Arg Leu Leu Gly Gln Glu
                95                 100                 105

Pro Leu Ala Leu Glu Ser Leu Phe Met Leu Ile Gln Gly Lys Val
               110                 115                 120

Lys Val Val Asp Trp Glu Glu Ser Thr Glu Val Thr Leu Tyr Phe
               125                 130                 135

Leu Ser Leu Leu Val Phe Arg Leu Gln Asn Leu Pro Cys Gly Met
               140                 145                 150

Glu Lys Leu Gly Ser Asp Val Ala Thr Leu Phe Thr His Ser His
               155                 160                 165

Val Val Ser Leu Val Ser Ala Ala Cys Leu Leu Gly Gln Leu
               170                 175                 180

Gly Gln Gln Gly Val Thr Phe Asp Leu Gln Pro Met Glu Trp Met
               185                 190                 195

Ala Ala Ala Thr His Ala Leu Ser Ala Pro Ala Glu Val Arg Leu
               200                 205                 210

Thr Pro Pro Gly Ser Cys Gly Phe Tyr Asp Gly Leu Leu Ile Leu
               215                 220                 225

Leu Leu Gln Leu Leu Thr Glu Gln Gly Lys Ala Ser Leu Ile Arg
               230                 235                 240

Asp Met Ser Ser Glu Met Trp Thr Val Leu Trp His Arg Phe
               245                 250                 255

Ser Met Val Leu Arg Leu Pro Glu Glu Ala Ser Ala Gln Glu Gly
               260                 265                 270

Glu Leu Ser Leu Ser Ser Pro Ser Glu Pro Asp Trp Thr
               275                 280                 285

Leu Ile Ser Pro Gln Gly Met Ala Ala Leu Leu Ser Leu Ala Met
               290                 295                 300

Ala Thr Phe Thr Gln Glu Pro Gln Leu Cys Leu Ser Cys Leu Ser
               305                 310                 315

Gln His Gly Ser Ile Leu Met Ser Ile Leu Lys His Leu Leu Cys
               320                 325                 330

Pro Ser Phe Leu Asn Gln Leu Arg Gln Ala Pro His Gly Ser Glu
               335                 340                 345

Phe Leu Pro Val Val Val Leu Ser Val Cys Gln Leu Leu Cys Phe
               350                 355                 360

Pro Phe Ala Leu Asp Met Asp Ala Asp Leu Leu Ile Val Val Leu
               365                 370                 375
```

```
Ala Asp Leu Arg Asp Ser Glu Val Ala Ala His Leu Leu Gln Val
            380                 385                 390

Cys Cys Tyr His Leu Pro Leu Met Gln Val Glu Leu Pro Ile Ser
            395                 400                 405

Leu Leu Thr Arg Leu Ala Leu Met Asp Pro Thr Ser Leu Asn Gln
            410                 415                 420

Phe Val Asn Thr Val Ser Ala Ser Pro Arg Thr Ile Val Ser Phe
            425                 430                 435

Leu Ser Val Ala Leu Leu Ser Asp Gln Pro Leu Leu Thr Ser Asp
            440                 445                 450

Leu Leu Ser Leu Leu Ala His Thr Ala Arg Val Leu Ser Pro Ser
            455                 460                 465

His Leu Ser Phe Ile Gln Glu Leu Leu Ala Gly Ser Asp Glu Ser
            470                 475                 480

Tyr Arg Pro Leu Arg Ser Leu Leu Gly His Pro Glu Asn Ser Val
            485                 490                 495

Arg Ala His Thr Tyr Arg Leu Leu Gly His Leu Leu Gln His Ser
            500                 505                 510

Met Ala Leu Arg Gly Ala Leu Gln Ser Gln Ser Gly Leu Leu Ser
            515                 520                 525

Leu Leu Leu Leu Gly Leu Gly Asp Lys Asp Pro Val Val Arg Cys
            530                 535                 540

Ser Ala Ser Phe Ala Val Gly Asn Ala Ala Tyr Gln Ala Gly Pro
            545                 550                 555

Leu Gly Pro Ala Leu Ala Ala Val Pro Ser Met Thr Gln Leu
            560                 565                 570

Leu Gly Asp Pro Gln Ala Gly Ile Arg Arg Asn Val Ala Ser Ala
            575                 580                 585

Leu Gly Asn Leu Gly Pro Glu Gly Leu Gly Glu Glu Leu Leu Gln
            590                 595                 600

Cys Glu Val Pro Gln Arg Leu Leu Glu Met Ala Cys Gly Asp Pro
            605                 610                 615

Gln Pro Asn Val Lys Glu Ala Ala Leu Ile Ala Leu Arg Ser Leu
            620                 625                 630

Gln Gln Glu Pro Gly Ile His Gln Val Leu Val Ser Leu Gly Ala
            635                 640                 645

Ser Glu Lys Leu Ser Leu Leu Ser Leu Gly Asn Gln Ser Leu Pro
            650                 655                 660

His Ser Ser Pro Arg Pro Ala Ser Ala Lys His Cys Arg Lys Leu
            665                 670                 675

Ile His Leu Leu Arg Pro Ala His Ser Met
            680                 685

<210> SEQ ID NO 22
<211> LENGTH: 221
<212> TYPE: PRT
<213> ORGANISM: Homo sapiens

<400> SEQUENCE: 22

Ser Tyr Ser Leu Leu Phe Ser Thr Gly Ala Pro Gln Val Ser Gln
  1               5                  10                  15

Pro Leu Arg Glu Gln Ser Glu Asp Ile Pro Gly Ala Ile Ser Ser
             20                  25                  30

Ala Leu Ala Ala Ile Cys Thr Ala Pro Val Gly Leu Pro Asp Cys
             35                  40                  45
```

Trp Asp Ala Lys Glu Gln Val Cys Trp His Leu Ala Asn Gln Leu
                50                      55                      60

Thr Glu Asp Ser Ser Gln Leu Arg Pro Ser Leu Ile Ser Gly Leu
                65                      70                      75

Gln His Pro Ile Leu Cys Leu His Leu Leu Lys Val Leu Tyr Ser
                80                      85                      90

Cys Cys Leu Val Ser Glu Gly Leu Cys Arg Leu Leu Gly Gln Glu
                95                     100                     105

Pro Leu Ala Leu Glu Ser Leu Phe Met Leu Ile Gln Gly Lys Val
               110                     115                     120

Lys Val Val Asp Trp Glu Glu Ser Thr Glu Val Thr Leu Tyr Phe
               125                     130                     135

Leu Ser Leu Leu Val Phe Arg Leu Gln Asn Leu Pro Cys Gly Met
               140                     145                     150

Glu Lys Leu Gly Ser Asp Val Ala Thr Leu Phe Thr His Ser His
               155                     160                     165

Val Val Ser Leu Val Ser Ala Ala Cys Leu Leu Gly Gln Leu
               170                     175                     180

Gly Gln Gln Gly Val Thr Phe Asp Leu Gln Pro Met Glu Trp Met
               185                     190                     195

Ala Ala Ala Thr His Ala Leu Ser Ala Pro Ala Glu Leu Leu Thr
               200                     205                     210

Glu Val Gln Met Asp Leu Gly Met Asp Gly Lys
               215                     220 221

<210> SEQ ID NO 23
<211> LENGTH: 795
<212> TYPE: PRT
<213> ORGANISM: Drosophila virilis

<400> SEQUENCE: 23

Met Asp Arg Tyr Ala Val Ser Ser Leu Val Gly Gln Gly Ser Phe
  1               5                      10                      15

Gly Cys Val Tyr Lys Ala Gln Arg Arg Asp Asp Lys Val Val
                20                      25                      30

Ala Ile Lys Val Ile Ser Lys Arg Gly Arg Ser Asn Arg Glu Leu
                35                      40                      45

Lys Asn Leu Arg Arg Glu Cys Asp Ile Gln Ala Arg Leu Lys His
                50                      55                      60

Pro His Val Ile Glu Met Val Glu Ser Phe Glu Ser Lys Phe Asp
                65                      70                      75

Leu Phe Val Val Thr Glu Phe Ala Leu Met Asp Leu His Arg Tyr
                80                      85                      90

Leu Ser Phe Asn Gly Ala Met Pro Glu Glu His Ala Gln Arg Val
                95                     100                     105

Val Cys His Leu Val Ser Ala Leu Tyr Tyr Leu His Ser Asn Arg
               110                     115                     120

Ile Leu His Arg Asp Leu Lys Pro Gln Asn Val Leu Leu Asp Lys
               125                     130                     135

Asn Met His Ala Lys Leu Cys Asp Phe Gly Leu Ala Arg Asn Met
               140                     145                     150

Thr Met Gly Thr His Val Leu Thr Ser Ile Lys Gly Thr Pro Leu
               155                     160                     165

Tyr Met Ala Pro Glu Leu Leu Ala Glu Gln Pro Tyr Asp His Gln

```
                        170                 175                 180
Ala Asp Met Trp Ser Leu Gly Cys Ile Ala Tyr Glu Ser Met Ala
                185                 190                 195
Gly Gln Pro Pro Phe Cys Ala Thr Ser Ile Leu His Leu Val Lys
                200                 205                 210
Leu Ile Lys His Glu Asp Val Lys Trp Pro Ser Thr Leu Ser Ser
                215                 220                 225
Glu Cys Arg Ser Phe Leu Gln Gly Leu Leu Glu Lys Asp Pro Ser
                230                 235                 240
Met Arg Ile Ser Trp Thr Gln Leu Leu Cys His Pro Phe Val Glu
                245                 250                 255
Gly Lys Leu Tyr Ile Ala Glu Val Gln Ala Ala Gln Thr Ser Pro
                260                 265                 270
Phe Ile Asn Pro Gln Leu Ala Lys Asp Thr Lys Lys Ser Gln Gln
                275                 280                 285
Leu Arg His Val Gly Ala Asp Leu Gly Asp Val Leu Ala Ala Leu
                290                 295                 300
Lys Leu Ser Asp Val Ala Asn Glu Asn Leu Ser Thr Ser Arg Asp
                305                 310                 315
Ser Ile Asn Ala Ile Ala Pro Ser Asp Ile Glu Gln Leu Glu Thr
                320                 325                 330
Asp Val Glu Asp Asn Val His Arg Leu Ile Val Pro Phe Ala Asp
                335                 340                 345
Ile Ser Tyr Arg Glu Leu Pro Cys Gly Thr Ala Ala Ala Ala Arg
                350                 355                 360
Arg Ala Gly Ala Met Pro Leu Ile Asn Ser Gln Thr Cys Phe Val
                365                 370                 375
Ser Gly Asn Ser Asn Met Ile Leu Asn His Leu Asn Asp Asn Phe
                380                 385                 390
Ala Ile Glu Ala Pro Ala Ser Ser Ala Thr Lys Ser Met Lys Ser
                395                 400                 405
Lys Leu Lys Leu Ala Leu Asn Ile Lys Gln Ser Arg Ser Lys Asp
                410                 415                 420
Leu Glu Lys Arg Lys Leu Ser Gln Asn Leu Asp Asn Phe Ser Leu
                425                 430                 435
Arg Leu Gly Gln Ser Ile Asp Ile Glu Val Gln Arg Lys Thr Thr
                440                 445                 450
Glu Met Leu Thr Gln Gln Ser Gln Ala Gln Gln Leu Gln Asp Arg
                455                 460                 465
Lys Thr Gln Gln Leu Lys Gln Ser Met His Ser Thr Asn Asp Glu
                470                 475                 480
Lys Leu Ser Ser Asp Asn Ser Pro Pro Cys Leu Leu Pro Gly Trp
                485                 490                 495
Asp Ser Cys Asp Glu Ser Gln Ser Pro Ile Glu Asn Asp Glu
                500                 505                 510
Trp Leu Ala Phe Leu His Arg Ser Ile Gln Glu Leu Leu Asp Gly
                515                 520                 525
Glu Phe Asp Ser Leu Lys Gln His Asn Leu Val Ser Ile Ile Val
                530                 535                 540
Ala Pro Leu Arg Asn Ser Lys Ala Ile Pro Lys Val Leu Gln Ser
                545                 550                 555
Val Ala Gln Leu Leu Ser Leu Pro Phe Val Leu Ala Glu Gln His
                560                 565                 570
```

```
Leu Val Ala Glu Ala Ile Lys Gly Val Tyr Ile Asp Val Lys Leu
            575                 580                 585

Val Pro Asn Leu Met Tyr Ala Cys Lys Leu Leu Leu Ser Gln Arg
            590                 595                 600

His Leu Thr Asp Ser Ala Ala Ser Leu Pro Ala Gly Thr Gly Val
            605                 610                 615

Ser Leu Ser Arg Thr Val Arg Ser Cys Ser Asp Leu Ser Ala Glu
            620                 625                 630

Glu Met Ser Thr Ala Cys Ser Leu Tyr Glu Leu Val Cys His Leu
            635                 640                 645

Val His Gln Gln Gln Gln Phe Leu Thr Gln Phe Cys Asp Ala Val
            650                 655                 660

Ala Ile Leu Ala Val Asn Asp Met Phe Ile Asn Phe Leu Thr His
            665                 670                 675

Asp Phe Lys Asp Ser Arg Pro Val Arg Leu Ala Ser Cys Met Leu
            680                 685                 690

Ala Leu Phe Cys Cys Val Leu Arg Glu Leu Pro Glu Asn Ala Glu
            695                 700                 705

Leu Val Glu Lys Ile Val Phe Asp Ser Arg Leu Gln Leu Ala Val
            710                 715                 720

Leu Leu Gln Ser Arg His His Leu Leu Arg Gln Arg Ala Cys Gln
            725                 730                 735

Met Leu Leu Leu Leu Ala Arg Phe Ser Leu Arg Gly Val Gln Cys
            740                 745                 750

Ile Trp Ser Gly Glu Leu Lys Ser Ala Leu Gln Ala Trp Pro Met
            755                 760                 765

Gln Gln Thr Cys Gln Ser Leu Arg Leu Glu Ala Ala Gln Thr Leu
            770                 775                 780

Asp Glu Leu Ser Gln Phe Ser Phe Phe Val Ala Gln Ala Thr Ala
            785                 790                 795

<210> SEQ ID NO 24
<211> LENGTH: 260
<212> TYPE: PRT
<213> ORGANISM: Homo sapiens

<400> SEQUENCE: 24

Met Glu Lys Tyr His Val Leu Glu Met Ile Gly Glu Gly Ser Phe
  1               5                  10                  15

Gly Arg Val Tyr Lys Gly Arg Arg Lys Tyr Ser Ala Gln Val Val
                 20                  25                  30

Ala Leu Lys Phe Ile Pro Lys Leu Gly Arg Ser Glu Lys Glu Leu
                 35                  40                  45

Arg Asn Leu Gln Arg Glu Ile Glu Ile Met Arg Gly Leu Arg His
                 50                  55                  60

Pro Asn Ile Val His Met Leu Asp Ser Phe Glu Thr Asp Lys Glu
                 65                  70                  75

Val Val Val Val Thr Asp Tyr Ala Glu Gly Glu Leu Phe Gln Ile
                 80                  85                  90

Leu Glu Asp Asp Gly Lys Leu Pro Glu Asp Gln Val Gln Ala Ile
                 95                 100                 105

Ala Ala Gln Leu Val Ser Ala Leu Tyr Tyr Leu His Ser His Arg
                110                 115                 120

Ile Leu His Arg Asp Met Lys Pro Gln Asn Ile Leu Leu Ala Lys
```

```
                        125                 130                 135

Gly Gly Gly Ile Lys Leu Cys Asp Phe Gly Phe Ala Arg Ala Met
                140                 145                 150

Ser Thr Asn Thr Met Val Leu Thr Ser Ile Lys Gly Thr Pro Leu
                155                 160                 165

Tyr Met Ser Pro Glu Leu Val Glu Glu Arg Pro Tyr Asp His Thr
                170                 175                 180

Ala Asp Leu Trp Ser Val Gly Cys Ile Leu Tyr Glu Leu Ala Val
                185                 190                 195

Gly Thr Pro Pro Phe Tyr Ala Thr Ser Ile Phe Gln Leu Val Ser
                200                 205                 210

Leu Ile Leu Lys Asp Pro Val Arg Trp Pro Ser Thr Ile Ser Pro
                215                 220                 225

Cys Phe Lys Asn Phe Leu Gln Gly Leu Leu Thr Lys Asp Pro Arg
                230                 235                 240

Gln Arg Leu Ser Trp Pro Asp Leu Leu Tyr His Pro Phe Ile Ala
                245                 250                 255

Gly His Val Thr Ile
                260

<210> SEQ ID NO 25
<211> LENGTH: 1315
<212> TYPE: PRT
<213> ORGANISM: artificial sequence
<220> FEATURE:
<223> OTHER INFORMATION: artificial sequence

<400> SEQUENCE: 25

Met Glu Lys Tyr His Val Leu Glu Met Ile Gly Glu Gly Ser Phe
  1               5                  10                  15

Gly Arg Val Tyr Lys Gly Arg Arg Lys Tyr Ser Ala Gln Val Val
                 20                  25                  30

Ala Leu Arg Phe Ile Pro Lys Leu Gly Arg Ser Glu Lys Glu Leu
                 35                  40                  45

Arg Asn Leu Gln Arg Glu Ile Glu Ile Met Arg Gly Leu Arg His
                 50                  55                  60

Pro Asn Ile Val His Met Leu Asp Ser Phe Glu Thr Asp Lys Glu
                 65                  70                  75

Val Val Val Val Thr Asp Tyr Ala Glu Gly Glu Leu Phe Gln Ile
                 80                  85                  90

Leu Glu Asp Asp Gly Lys Leu Pro Glu Asp Gln Val Gln Ala Ile
                 95                 100                 105

Ala Ala Gln Leu Val Ser Ala Leu Tyr Tyr Leu His Ser His Arg
                110                 115                 120

Ile Leu His Arg Asp Met Lys Pro Gln Asn Ile Leu Leu Ala Lys
                125                 130                 135

Gly Gly Gly Ile Lys Leu Cys Asp Phe Gly Phe Ala Arg Ala Met
                140                 145                 150

Ser Thr Asn Thr Met Val Leu Thr Ser Ile Lys Gly Thr Pro Leu
                155                 160                 165

Tyr Met Ser Pro Glu Leu Val Glu Glu Arg Pro Tyr Asp His Thr
                170                 175                 180

Ala Asp Leu Trp Ser Val Gly Cys Ile Leu Tyr Glu Leu Ala Val
                185                 190                 195

Gly Thr Pro Pro Phe Tyr Ala Thr Ser Ile Phe Gln Leu Val Ser
```

-continued

```
                    200                 205                 210
Leu Ile Leu Lys Asp Pro Val Arg Trp Pro Ser Thr Ile Ser Pro
                215                 220                 225
Cys Phe Lys Asn Phe Leu Gln Gly Leu Leu Thr Lys Asp Pro Arg
                230                 235                 240
Gln Arg Leu Ser Trp Pro Asp Leu Leu Tyr His Pro Phe Ile Ala
                245                 250                 255
Gly His Val Thr Ile Ile Thr Glu Pro Ala Gly Pro Asp Leu Gly
                260                 265                 270
Thr Pro Phe Thr Ser Arg Leu Pro Pro Glu Leu Gln Val Leu Lys
                275                 280                 285
Asp Glu Gln Ala His Arg Leu Ala Pro Lys Gly Asn Gln Ser Arg
                290                 295                 300
Ile Leu Thr Gln Ala Tyr Lys Arg Met Ala Glu Glu Ala Met Gln
                305                 310                 315
Lys Lys His Gln Asn Thr Gly Pro Ala Leu Glu Gln Glu Asp Lys
                320                 325                 330
Thr Ser Lys Val Ala Pro Gly Thr Ala Pro Leu Pro Arg Leu Gly
                335                 340                 345
Ala Thr Pro Gln Glu Ser Ser Leu Leu Ala Gly Ile Leu Ala Ser
                350                 355                 360
Glu Leu Lys Ser Ser Trp Ala Lys Ser Gly Thr Gly Glu Val Pro
                365                 370                 375
Ser Ala Pro Arg Glu Asn Arg Thr Thr Pro Asp Cys Glu Arg Ala
                380                 385                 390
Phe Pro Glu Glu Arg Pro Glu Val Leu Gly Gln Arg Ser Thr Asp
                395                 400                 405
Val Val Asp Leu Glu Asn Glu Glu Pro Asp Ser Asp Asn Glu Trp
                410                 415                 420
Gln His Leu Leu Glu Thr Thr Glu Pro Val Pro Ile Gln Leu Lys
                425                 430                 435
Ala Pro Leu Thr Leu Leu Cys Asn Pro Asp Phe Cys Gln Arg Ile
                440                 445                 450
Gln Ser Gln Leu His Glu Ala Gly Gly Gln Ile Leu Lys Gly Ile
                455                 460                 465
Leu Glu Gly Ala Ser His Ile Leu Pro Ala Phe Arg Val Leu Ser
                470                 475                 480
Ser Leu Leu Ser Ser Cys Ser Asp Ser Val Ala Leu Tyr Ser Phe
                485                 490                 495
Cys Arg Glu Ala Gly Leu Pro Gly Leu Leu Ser Leu Leu Arg
                500                 505                 510
His Ser Gln Glu Ser Asn Ser Leu Gln Gln Ser Trp Tyr Gly
                515                 520                 525
Thr Phe Leu Gln Asp Leu Met Ala Val Ile Gln Ala Tyr Phe Ala
                530                 535                 540
Cys Thr Phe Asn Leu Glu Arg Ser Gln Thr Ser Asp Ser Leu Gln
                545                 550                 555
Val Phe Gln Glu Ala Ala Asn Leu Phe Leu Asp Leu Gly Lys
                560                 565                 570
Leu Leu Ala Gln Pro Asp Asp Ser Glu Gln Thr Leu Arg Arg Asp
                575                 580                 585
Ser Leu Met Cys Phe Thr Val Leu Cys Glu Ala Met Asp Gly Asn
                590                 595                 600
```

-continued

```
Ser Arg Ala Ile Ser Lys Ala Phe Tyr Ser Ser Leu Leu Thr Thr
            605                 610                 615
Gln Gln Val Val Leu Asp Gly Leu Leu His Gly Leu Thr Val Pro
            620                 625                 630
Gln Leu Pro Val His Thr Pro Gln Gly Ala Pro Gln Val Ser Gln
            635                 640                 645
Pro Leu Arg Glu Gln Ser Glu Asp Ile Pro Gly Ala Ile Ser Ser
            650                 655                 660
Ala Leu Ala Ala Ile Cys Thr Ala Pro Val Gly Leu Pro Asp Cys
            665                 670                 675
Trp Asp Ala Lys Glu Gln Val Cys Trp His Leu Ala Asn Gln Leu
            680                 685                 690
Thr Glu Asp Ser Ser Gln Leu Arg Pro Ser Leu Ile Ser Gly Leu
            695                 700                 705
Gln His Pro Ile Leu Cys Leu His Leu Leu Lys Val Leu Tyr Ser
            710                 715                 720
Cys Cys Leu Val Ser Glu Gly Leu Cys Arg Leu Leu Gly Gln Glu
            725                 730                 735
Pro Leu Ala Leu Glu Ser Leu Phe Met Leu Ile Gln Gly Lys Val
            740                 745                 750
Lys Val Val Asp Trp Glu Glu Ser Thr Glu Val Thr Leu Tyr Phe
            755                 760                 765
Leu Ser Leu Leu Val Phe Arg Leu Gln Asn Leu Pro Cys Gly Met
            770                 775                 780
Glu Lys Leu Gly Ser Asp Val Ala Thr Leu Phe Thr His Ser His
            785                 790                 795
Val Val Ser Leu Val Ser Ala Ala Cys Leu Leu Gly Gln Leu
            800                 805                 810
Gly Gln Gln Gly Val Thr Phe Asp Leu Gln Pro Met Glu Trp Met
            815                 820                 825
Ala Ala Ala Thr His Ala Leu Ser Ala Pro Ala Glu Val Arg Leu
            830                 835                 840
Thr Pro Pro Gly Ser Cys Gly Phe Tyr Asp Gly Leu Leu Ile Leu
            845                 850                 855
Leu Leu Gln Leu Leu Thr Glu Gln Gly Lys Ala Ser Leu Ile Arg
            860                 865                 870
Asp Met Ser Ser Ser Glu Met Trp Thr Val Leu Trp His Arg Phe
            875                 880                 885
Ser Met Val Leu Arg Leu Pro Glu Glu Ala Ser Ala Gln Glu Gly
            890                 895                 900
Glu Leu Ser Leu Ser Ser Pro Ser Pro Glu Pro Asp Trp Thr
            905                 910                 915
Leu Ile Ser Pro Gln Gly Met Ala Ala Leu Leu Ser Leu Ala Met
            920                 925                 930
Ala Thr Phe Thr Gln Glu Pro Gln Leu Cys Leu Ser Cys Leu Ser
            935                 940                 945
Gln His Gly Ser Ile Leu Met Ser Ile Leu Lys His Leu Leu Cys
            950                 955                 960
Pro Ser Phe Leu Asn Gln Leu Arg Gln Ala Pro His Gly Ser Glu
            965                 970                 975
Phe Leu Pro Val Val Leu Ser Val Cys Gln Leu Leu Cys Phe
            980                 985                 990
```

-continued

Pro Phe Ala Leu Asp Met Asp Ala Asp Leu Leu Ile Val Val Leu
                995                1000                1005

Ala Asp Leu Arg Asp Ser Glu Val Ala Ala His Leu Leu Gln Val
               1010                1015                1020

Cys Cys Tyr His Leu Pro Leu Met Gln Val Glu Leu Pro Ile Ser
               1025                1030                1035

Leu Leu Thr Arg Leu Ala Leu Met Asp Pro Thr Ser Leu Asn Gln
               1040                1045                1050

Phe Val Asn Thr Val Ser Ala Ser Pro Arg Thr Ile Val Ser Phe
               1055                1060                1065

Leu Ser Val Ala Leu Leu Ser Asp Gln Pro Leu Leu Thr Ser Asp
               1070                1075                1080

Leu Leu Ser Leu Leu Ala His Thr Ala Arg Val Leu Ser Pro Ser
               1085                1090                1095

His Leu Ser Phe Ile Gln Glu Leu Leu Ala Gly Ser Asp Glu Ser
               1100                1105                1110

Tyr Arg Pro Leu Arg Ser Leu Leu Gly His Pro Glu Asn Ser Val
               1115                1120                1125

Arg Ala His Thr Tyr Arg Leu Leu Gly His Leu Leu Gln His Ser
               1130                1135                1140

Met Ala Leu Arg Gly Ala Leu Gln Ser Gln Ser Gly Leu Leu Ser
               1145                1150                1155

Leu Leu Leu Leu Gly Leu Gly Asp Lys Asp Pro Val Val Arg Cys
               1160                1165                1170

Ser Ala Ser Phe Ala Val Gly Asn Ala Ala Tyr Gln Ala Gly Pro
               1175                1180                1185

Leu Gly Pro Ala Leu Ala Ala Ala Val Pro Ser Met Thr Gln Leu
               1190                1195                1200

Leu Gly Asp Pro Gln Ala Gly Ile Arg Arg Asn Val Ala Ser Ala
               1205                1210                1215

Leu Gly Asn Leu Gly Pro Glu Gly Leu Gly Glu Glu Leu Leu Gln
               1220                1225                1230

Cys Glu Val Pro Gln Arg Leu Leu Glu Met Ala Cys Gly Asp Pro
               1235                1240                1245

Gln Pro Asn Val Lys Glu Ala Ala Leu Ile Ala Leu Arg Ser Leu
               1250                1255                1260

Gln Gln Glu Pro Gly Ile His Gln Val Leu Val Ser Leu Gly Ala
               1265                1270                1275

Ser Glu Lys Leu Ser Leu Leu Ser Leu Gly Asn Gln Ser Leu Pro
               1280                1285                1290

His Ser Ser Pro Arg Pro Ala Ser Ala Lys His Cys Arg Lys Leu
               1295                1300                1305

Ile His Leu Leu Arg Pro Ala His Ser Met
               1310                1315

<210> SEQ ID NO 26
<211> LENGTH: 4586
<212> TYPE: DNA
<213> ORGANISM: Drosophila virilis

<400> SEQUENCE: 26
tgcagagtct gggccatcgg ctagctctgt agatgtgtaa tagaggcatc            50
ttcgcgcgca gcatcgattc gcgctccagt tggttgagat gccgaatgtt           100
ggtgcgcgtc tcaaagatga cgccgacatg gtgcatatac agaaaaaaga           150

```
aacccgagcc taatggccgc gtattatcgc tgaggcggcc ggcgattttc        200
aacaaatgct acttaccaat tagcgcgtgc gataaaatta cgtacaaatt        250
ggcgtcgcgc atatttctgg cgtttgtgtt gcgtgtatct agttagtggg        300
ctcgtctatt cattatttac ttttggggcg tctgtttgat caaattagca        350
gtgtctccta tgatatgcct gcagctttta cccgtaaaca aaattatttg        400
ccacagctga tttattcgtt gccatgtaga ttaatcagct gtttcgcaat        450
ttttaaaacc aggtgacttt ttaaaattgt accagctgtg tgtatcgatg        500
tgcaagcata ctcattacgc catatgctgg tatatttata tcgaatataa        550
acggttttgg tattttaata atcttaaaga agaaatagtt atgtgctgtg        600
tatatgttca tcaagaactg ttcaaaatgt gcgccatact gatgttaatt        650
ttgttttgct ggttttttttt gggaaaataa attgacgtgt tgatgtctcc        700
gaatatatcg atacaatagc tatcattcgg acaagatatc gatatgtgga        750
gtgtgttcgg tattttgcct ttagtttttt gtttttaaat tgcagtcaca        800
ctgcggctta ttgaatttaa ggcacttcaa agcgcatttt actgtagaaa        850
gttgagttct atttgcggtg acaatggacc gctacgcggt tagctctctg        900
gtaggacaag gctcatttgg ctgtgtgtac aaggcccagc ggcgcgatga        950
tgacaaagtg gtggccatca aagtcatatc aaaggtgagc tcaattgcat       1000
cccggcttag ctgaataaaa gagtattcta cgaattggcg tgttctttgt       1050
ttgcagcgtg gtcgttccaa tcgcgagctt aagaacctgc gtcgcgaatg       1100
tgacattcag gcgcgtctca agcatccgca tgttatagaa atggtggagt       1150
cgttcgaatc caaattcgat ttgttcgtgg tcaccgagtt cgctctaatg       1200
gacttgcatc gatatttgtc ctttaatggc gccatgcccg aggagcacgc       1250
acagcgtgtt gtctgtcatt tggtgtcggc gctctattat ctgcactcga       1300
atcgcatact gcatcgggat ctaaagccgc aaaatgtgct gttggacaaa       1350
aacatgcacg ccaagctctg cgactttggg ctggcacgca acatgacgat       1400
gggcacacat gtgttgactt ccataaaggg cacgccgctt tatatggcgc       1450
cggagctgct ggctgagcag ccgtacgatc accaggcaga tatgtggtcg       1500
ctgggatgca ttgcctatga gagtatggcg ggccagccgc cgttctgcgc       1550
aacctctata ctgcatctgg tgaagctgat caagcacgag gacgtcaaat       1600
ggccgagcac gctgagcagc gagtgccgtt ccttttttgca gggcttgctc       1650
gagaaggatc ctagcatgcg catctcatgg acgcagctgc tttgccatcc       1700
ttttgtcgag ggcaagctat acatagccga ggtacaggca gcacaaactt       1750
cgcccttat aaatccccag ctggccaagg acaccaaaaa atcacagcaa         1800
ttgaggtgcg tttataacgt gtactgtagc cagctccact tatcgttcaa       1850
tttttatgta ggcatgtagg cgcagatttg ggcgatgtct tggcagcgtt       1900
aaagttgagc gatgtggcca atgaaaaactt gagcacatcg cgagatagta       1950
tcaatgccat tgcgccgagt gacattgagc agctggaaac cgatgttgag       2000
gataatgtgc atcggcttat agtgccattt gcagatattt cctacagaga       2050
gttgccatgc ggcactgcag cagctgctcg tcgagctggt gccatgccac       2100
```

-continued

| | |
|---|---|
| tgattaattc gcaaacctgc tttgtaagtg gcaactccaa tatgatactc | 2150 |
| aatcatctga acgacaattt tgcaatcgaa gcgcctgctt cgagcgcaac | 2200 |
| caagtccatg aagtcgaagc tgaagctggc tctcaatata aaacagtcgc | 2250 |
| gtagcaagga tttggaaaag cgtaagctga gtcaaaattt ggataacttt | 2300 |
| tcgctgcgcc tgggacagag cattgacata gaagtgcagc gcaaaacaac | 2350 |
| tgagatgctc acgcagcaat cgcaggcaca acagctgcag gataggaaga | 2400 |
| cacagcagct gaagcaatcg atgcattcca ccaacgacga gaaattgagc | 2450 |
| agcgagtgag taaatgcatc catatttaaa agtgaagctc tctaaagcta | 2500 |
| tttggtttat aatagcaatt cgccgccttg tctgttgccc ggttgggaca | 2550 |
| gctgcgatga atctcagagc ccgcccattg agaatgacga gtggctggcg | 2600 |
| ttcttgcatc gctccataca ggagctgctg acggcgaat ttgattcgct | 2650 |
| gaagcagcac aatctagtca gcataattgt ggcgccattg cgaaactcca | 2700 |
| aggccatacc caaggtgctg cagagcgtgg cgcagctgct gtcgctgccc | 2750 |
| tttgtgctgg ccgaacagca tttggtagcg gaggccataa aaggagttta | 2800 |
| tattgatgtc aagctggtgc ccaacttaat gtacgcctgc aagctgcttc | 2850 |
| tctcgcagcg ccaccttacc gattcggctg cttcactgcc agccggcacg | 2900 |
| ggcgtctccc tgagtcgaac cgtacgcagc tgctccgacc tgagtgccga | 2950 |
| ggagatgagc accgcctgca gcctgtacga gctggtctgc catctggtcc | 3000 |
| atcagcagca gcagttcctc acccagttct gtgacgctgt ggcaatactc | 3050 |
| gccgtcaacg acatgttcat aaattttctt acacatggtg agcagctggc | 3100 |
| tggacacagt gtgagacgca agcttaacca ttccttgctt tgcagatttt | 3150 |
| aaggatagca ggccggtgcg actcgctagc tgcatgctgg cattgttctg | 3200 |
| ttgcgttttg cgtgaactac ccgagaacgc cgagctggtg gagaaaattg | 3250 |
| tatttgactc gcgcctacag ctggccgtcc tgctgcagag ccgtcatcat | 3300 |
| ttgttgcgtc agcgcgcctg tcaaatgctg ttgctattgg cacgctttag | 3350 |
| cctgcgcggc gtacagtgca tctggagtgg ggagctgaag agtgcgctcc | 3400 |
| aggcgtggcc gatgcagcaa acgtgtcaat cattgcgact ggaagccgcc | 3450 |
| caaacgctgg atgagcttag ccagttcagc ttctttgttg ctcaggcaac | 3500 |
| tgcttagtct ttattaataa ttgtacttgt atttgtttaa taaatcttaa | 3550 |
| tccttgtcta gccgaacaga ccttccaaat tgccttgaaa gtagtcgagc | 3600 |
| agctcgtcca gatagctgct aaagccatca aagcccaaaa ggtagctacc | 3650 |
| attacagtcc tgctcgtaca tctcgtttag tttcgaaata tccttatccg | 3700 |
| acagccgcgc gctggcccag tgaggcatac ggatcctaat gataatagca | 3750 |
| tgcattatta ttatttttca caatgtgtta ttcgtttaat acttataaaa | 3800 |
| ccttaaattg tatgcatgta tgtatctatc ttatacctaa ttaatgaatg | 3850 |
| aaatttatta acttgtctat ggatgtatgt gcatgtatgt atgtatgtat | 3900 |
| gtatgcataa aaatgtatgt tcatttataa caaacgcaga caaagataac | 3950 |
| gatctgctgc tctacttccc gaatctcata aattcaagta cgccccgcag | 4000 |
| atttcacgag tacatcacaa gtgttttttt ttaacaagta atgttggtat | 4050 |
| gtatttatgt atatatgtat ttaagtatgt atgtatttat gtatgtatgt | 4100 |

-continued

```
atgtatttat gtatgtatgt atttatgtat gtatgtattt atgtatgtat          4150
gtatttatgt atgtatttat ttatgtatat atgtatttaa gtatgtatgt          4200
atgtatttat gcatttatgt atttatgtat gtatgtataa gagtatgtgt          4250
gtgtgtagat acatgtatgt atgtatgtat gtatgcgtgt atatttattt          4300
atagtaaaca taccaacttt acttcccgct gccttgcgaa tttaaaataa          4350 cgtatttttta aatgatgccc tactcctcga ttctcaaaca tttaagtaag         4400
ctctacaggt ttttccgatt tgattgtttt gtaaagttgt gttttttttt          4450
ctgctcgatc tcttgtgtat tctctactct ttgtgtgcct ctctttagtt          4500
ttctctcctt ctctcttgct ctccctgtt ctctctctat ctctctccct           4550
ccctctttcc acctatctca ttctctttct aagctt                         4586
```

<210> SEQ ID NO 27
<211> LENGTH: 1055
<212> TYPE: PRT
<213> ORGANISM: Homo sapiens

<400> SEQUENCE: 27

```
Ile Thr Glu Pro Ala Gly Pro Asp Leu Gly Thr Pro Phe Thr Ser
  1               5                  10                  15

Arg Leu Pro Pro Glu Leu Gln Val Leu Lys Asp Glu Gln Ala His
             20                  25                  30

Arg Leu Ala Pro Lys Gly Asn Gln Ser Arg Ile Leu Thr Gln Ala
         35                  40                  45

Tyr Lys Arg Met Ala Glu Glu Ala Met Gln Lys Lys His Gln Asn
     50                  55                  60

Thr Gly Pro Ala Leu Glu Gln Glu Asp Lys Thr Ser Lys Val Ala
 65                  70                  75

Pro Gly Thr Ala Pro Leu Pro Arg Leu Gly Ala Thr Pro Gln Glu
             80                  85                  90

Ser Ser Leu Leu Ala Gly Ile Leu Ala Ser Glu Leu Lys Ser Ser
             95                 100                 105

Trp Ala Lys Ser Gly Thr Gly Glu Val Pro Ser Ala Pro Arg Glu
            110                 115                 120

Asn Arg Thr Thr Pro Asp Cys Glu Arg Ala Phe Pro Glu Glu Arg
            125                 130                 135

Pro Glu Val Leu Gly Gln Arg Ser Thr Asp Val Val Asp Leu Glu
            140                 145                 150

Asn Glu Glu Pro Asp Ser Asp Asn Glu Trp Gln His Leu Leu Glu
            155                 160                 165

Thr Thr Glu Pro Val Pro Ile Gln Leu Lys Ala Pro Leu Thr Leu
            170                 175                 180

Leu Cys Asn Pro Asp Phe Cys Gln Arg Ile Gln Ser Gln Leu His
            185                 190                 195

Glu Ala Gly Gly Gln Ile Leu Lys Gly Ile Leu Glu Gly Ala Ser
            200                 205                 210

His Ile Leu Pro Ala Phe Arg Val Leu Ser Ser Leu Ser Ser
            215                 220                 225

Cys Ser Asp Ser Val Ala Leu Tyr Ser Phe Cys Arg Glu Ala Gly
            230                 235                 240

Leu Pro Gly Leu Leu Leu Ser Leu Leu Arg His Ser Gln Glu Ser
            245                 250                 255
```

```
Asn Ser Leu Gln Gln Gln Ser Trp Tyr Gly Thr Phe Leu Gln Asp
            260                 265                 270
Leu Met Ala Val Ile Gln Ala Tyr Phe Ala Cys Thr Phe Asn Leu
            275                 280                 285
Glu Arg Ser Gln Thr Ser Asp Ser Leu Gln Val Phe Gln Glu Ala
            290                 295                 300
Ala Asn Leu Phe Leu Asp Leu Leu Gly Lys Leu Leu Ala Gln Pro
            305                 310                 315
Asp Asp Ser Glu Gln Thr Leu Arg Arg Asp Ser Leu Met Cys Phe
            320                 325                 330
Thr Val Leu Cys Glu Ala Met Asp Gly Asn Ser Arg Ala Ile Ser
            335                 340                 345
Lys Ala Phe Tyr Ser Ser Leu Leu Thr Thr Gln Gln Val Val Leu
            350                 355                 360
Asp Gly Leu Leu His Gly Leu Thr Val Pro Gln Leu Pro Val His
            365                 370                 375
Thr Pro Gln Gly Ala Pro Gln Val Ser Gln Pro Leu Arg Glu Gln
            380                 385                 390
Ser Glu Asp Ile Pro Gly Ala Ile Ser Ser Ala Leu Ala Ala Ile
            395                 400                 405
Cys Thr Ala Pro Val Gly Leu Pro Asp Cys Trp Asp Ala Lys Glu
            410                 415                 420
Gln Val Cys Trp His Leu Ala Asn Gln Leu Thr Glu Asp Ser Ser
            425                 430                 435
Gln Leu Arg Pro Ser Leu Ile Ser Gly Leu Gln His Pro Ile Leu
            440                 445                 450
Cys Leu His Leu Leu Lys Val Leu Tyr Ser Cys Cys Leu Val Ser
            455                 460                 465
Glu Gly Leu Cys Arg Leu Leu Gly Gln Glu Pro Leu Ala Leu Glu
            470                 475                 480
Ser Leu Phe Met Leu Ile Gln Gly Lys Val Lys Val Val Asp Trp
            485                 490                 495
Glu Glu Ser Thr Glu Val Thr Leu Tyr Phe Leu Ser Leu Leu Val
            500                 505                 510
Phe Arg Leu Gln Asn Leu Pro Cys Gly Met Glu Lys Leu Gly Ser
            515                 520                 525
Asp Val Ala Thr Leu Phe Thr His Ser His Val Val Ser Leu Val
            530                 535                 540
Ser Ala Ala Ala Cys Leu Leu Gly Gln Leu Gly Gln Gln Gly Val
            545                 550                 555
Thr Phe Asp Leu Gln Pro Met Glu Trp Met Ala Ala Ala Thr His
            560                 565                 570
Ala Leu Ser Ala Pro Ala Glu Val Arg Leu Thr Pro Pro Gly Ser
            575                 580                 585
Cys Gly Phe Tyr Asp Gly Leu Leu Ile Leu Leu Leu Gln Leu Leu
            590                 595                 600
Thr Glu Gln Gly Lys Ala Ser Leu Ile Arg Asp Met Ser Ser Ser
            605                 610                 615
Glu Met Trp Thr Val Leu Trp His Arg Phe Ser Met Val Leu Arg
            620                 625                 630
Leu Pro Glu Glu Ala Ser Ala Gln Glu Gly Glu Leu Ser Leu Ser
            635                 640                 645
```

```
Ser Pro Pro Ser Pro Glu Pro Asp Trp Thr Leu Ile Ser Pro Gln
                650                 655                 660
Gly Met Ala Ala Leu Leu Ser Leu Ala Met Ala Thr Phe Thr Gln
                665                 670                 675
Glu Pro Gln Leu Cys Leu Ser Cys Leu Ser Gln His Gly Ser Ile
                680                 685                 690
Leu Met Ser Ile Leu Lys His Leu Leu Cys Pro Ser Phe Leu Asn
                695                 700                 705
Gln Leu Arg Gln Ala Pro His Gly Ser Glu Phe Leu Pro Val Val
                710                 715                 720
Val Leu Ser Val Cys Gln Leu Cys Phe Pro Phe Ala Leu Asp
                725                 730                 735
Met Asp Ala Asp Leu Leu Ile Val Val Leu Ala Asp Leu Arg Asp
                740                 745                 750
Ser Glu Val Ala Ala His Leu Leu Gln Val Cys Cys Tyr His Leu
                755                 760                 765
Pro Leu Met Gln Val Glu Leu Pro Ile Ser Leu Leu Thr Arg Leu
                770                 775                 780
Ala Leu Met Asp Pro Thr Ser Leu Asn Gln Phe Val Asn Thr Val
                785                 790                 795
Ser Ala Ser Pro Arg Thr Ile Val Ser Phe Leu Ser Val Ala Leu
                800                 805                 810
Leu Ser Asp Gln Pro Leu Leu Thr Ser Asp Leu Leu Ser Leu Leu
                815                 820                 825
Ala His Thr Ala Arg Val Leu Ser Pro Ser His Leu Ser Phe Ile
                830                 835                 840
Gln Glu Leu Leu Ala Gly Ser Asp Glu Ser Tyr Arg Pro Leu Arg
                845                 850                 855
Ser Leu Leu Gly His Pro Glu Asn Ser Val Arg Ala His Thr Tyr
                860                 865                 870
Arg Leu Leu Gly His Leu Leu Gln His Ser Met Ala Leu Arg Gly
                875                 880                 885
Ala Leu Gln Ser Gln Ser Gly Leu Leu Ser Leu Leu Leu Gly
                890                 895                 900
Leu Gly Asp Lys Asp Pro Val Val Arg Cys Ser Ala Ser Phe Ala
                905                 910                 915
Val Gly Asn Ala Ala Tyr Gln Ala Gly Pro Leu Gly Pro Ala Leu
                920                 925                 930
Ala Ala Ala Val Pro Ser Met Thr Gln Leu Leu Gly Asp Pro Gln
                935                 940                 945
Ala Gly Ile Arg Arg Asn Val Ala Ser Ala Leu Gly Asn Leu Gly
                950                 955                 960
Pro Glu Gly Leu Gly Glu Glu Leu Leu Gln Cys Glu Val Pro Gln
                965                 970                 975
Arg Leu Leu Glu Met Ala Cys Gly Asp Pro Gln Pro Asn Val Lys
                980                 985                 990
Glu Ala Ala Leu Ile Ala Leu Arg Ser Leu Gln Gln Glu Pro Gly
                995                1000                1005
Ile His Gln Val Leu Val Ser Leu Gly Ala Ser Glu Lys Leu Ser
                1010                1015                1020
Leu Leu Ser Leu Gly Asn Gln Ser Leu Pro His Ser Ser Pro Arg
                1025                1030                1035
Pro Ala Ser Ala Lys His Cys Arg Lys Leu Ile His Leu Leu Arg
```

-continued

```
            1040              1045              1050
Pro Ala His Ser Met
            1055
```

FUSED POLYPEPTIDES

This application is a non-provisional application claiming priority under 35 U.S.C. §119(e) to provisional application No. 60/076,072 filed Feb. 26, 1998, the contents of which are incorporated herein by reference.

FIELD OF THE INVENTION

The present invention relates generally to signaling molecules, specifically to signaling and mediator molecules in the hedgehog (Hh) cascade which are involved in cell proliferation and differentiation.

BACKGROUND OF THE INVENTION

Development of multicellular organisms depends, at least in part, on mechanisms which specify, direct or maintain positional information to pattern cells, tissues, or organs. Various secreted signaling molecules, such as members of the transforming growth factor-beta (TGF-β), Wnt, fibroblast growth factors and hedgehog families have been associated with patterning activity of different cells and structures in Drosophila as well as in vertebrates. Perrimon, *Cell*: 80: 517–520 (1995).

Hedgehog (Rh) was first identified as a segment-polarity gene by a genetic screen in *Drosophila melanogaster*, Nusslein-Volhard et al., *Roux. Arch. Dev. Biol.* 193: 267–282 (1984), that plays a wide variety of developmental functions. Perrimon, supra. Although only one Drosophila Hh gene has been identified, three mammalian Hh homologues have been isolated: Sonic Hh (SHh), Desert Hh (DHh) and Indian Hh (IHh), Echelard et al., *Cell* 75: 1417–30 (1993); Riddle et al., *Cell* 75: 1401–16 (1993). SHh is expressed at high level in the notochord and floor plate of developing vertebrate embryos. In vitro explant assays as well as ectopic expression of SHh in transgenic animals show that SHh plays a key role in neuronal tube patterning, Echelard et al., supra., Krauss et al., *Cell* 75, 1431–44 (1993), Riddle et al., *Cell* 75: 1401–16 (1993), Roelink et al., *Cell* 81: 445–55 (1995). In vitro explant assays as well as ectopic expression of SHh in transgenic animals show that SHh plays a key role in neural tube patterning, Echelard et al. (1993), supra.; Ericson et al., *Cell* 81: 747–56 (1995); Marti et al., *Nature* 375: 322–5 (1995); Roelink et al. (1995), Hynes et al., *Neuron* 19: 15–26 (1997). Hh also plays a role in the development of limbs (Krauss et al., *Cell* 75: 1431–44 (1993); Laufer et al., *Cell* 79, 993–1003 (1994)), somites (Fan and Tessier-Lavigne, *Cell* 79 1175–86 (1994); Johnson et al., *Cell* 79: 1165–73 (1994)), lungs (Bellusci et al., *Develop.* 124: 53–63 (1997) and skin (Oro et al., *Science* 276: 817–21 (1997). Likewise, IHh and DHh are involved in bone, gut and germinal cell development, Apelqvist et al., *Curr. Biol.* 7: 801–4 (1997); Bellusci et al., *Development.* 124: 53–63 (1997); Bitgood et al., *Curr. Biol.* 6: 298–304 (1996); Roberts et al., *Development* 121: 3163–74 (1995). SHh knockout mice further strengthened the notion that SHh is critical to many aspect of vertebrate development, Chiang et al., *Nature* 383: 407–13 (1996). These mice show defects in midline structures such as the notochord and the floor plate, absence of ventral cell types in neural tube, absence of distal limb structures, cyclopia, and absence of the spinal column and most of the ribs.

At the cell surface, the Hh signals is thought to be relayed by the 12 transmembrane domain protein Patched (Ptch) [Hooper and Scott, *Cell* 59: 751–65 (1989); Nakano et al., *Nature* 341: 508–13 (1989)] and the G-protein coupled like receptor Smoothened (Smo) [Alcedo et al., *Cell* 86: 221–232 (1996); van den Heuvel and Ingham, *Nature* 382: 547–551 (1996)]. Both genetic and biochemical evidence support a receptor model where Ptch and Smo are part of a multicomponent receptor complex, Chen and Struhl, *Cell* 87: 553–63 (1996); Marigo et al., *Nature* 384: 176–9 (1996); Stone et al., *Nature* 384: 129–34 (1996). Upon binding of Hh to Ptch, the normal inhibitory effect of Ptch on Smo is relieved, allowing Smo to transduce the Hh signal across the plasma membrane. Loss of function mutations in the Ptch gene have been identified in patients with the basal cell nevus syndrome (BCNS), a hereditary disease characterized by multiple basal cell carcinomas (13CCs). Disfunctional Ptch gene mutations have also been associated with a large percentage of sporadic basal cell carcinoma tumors, Chidambaram et al., *Cancer Research* 56: 4599–601 (1996); Gailani et al., *Nature Genet.* 14: 78–81 (1996); Hahn et al., *Cell* 85: 841–51 (1996); Johnson et al., *Science* 272: 1668–71 (1996); Unden et al., *Cancer Res.* 56: 4562–5 (1996); Wicking et al., *Am. J. Hum. Genet.* 60: 21–6 (1997). Loss of Ptch function is thought to cause an uncontrolled Smo signaling in basal cell carcinoma Similarly, activating Smo mutations have been identified in sporatic BCC tumors (Xie et al., *Nature* 391: 90–2 (1998)), emphasizing the role of Smo as the signaling subunit in the receptor complex for SHh. However, the exact mechanism by which Ptch controls Smo activity still has yet to be clarified and the signaling mechanisms by which the Hh signal is transmitted from the receptor to downstream targets also remain to be elucidated. Genetic epistatic analysis in Drosophila has identified several segment-polarity genes which appear to function as components of the Hh signal transduction pathway, Ingham, *Curr. Opin. Genet. Dev.* 5: 492–8 (1995); Perrimon, supra. These include a kinesin-like molecule, Costal-2 (Cos-2) [Robbins et al., *Cell* 90: 225–34 (1997); Sisson et al., *Cell* 90: 235–45 (1997)], a protein designated fused [Preat et al., *Genetics* 135: 1047–62 (1993); Therond et al., *Proc. Natl Acad Sci. USA* 93: 4224–8 (1996)], a novel molecule with unknown function designated Suppressor of fused [Pham et al., *Genetics* 140: 587–98 (1995); Preat, *Genetics* 132: 725–36 (1992)] and a zinc finger protein Ci. [Alexandre et al., *Genes Dev.* 10: 2003–13 (1996); Dominguez et al., *Science* 272: 1621–5 (1996); Orenic et al., *Genes Dev.* 4: 1053–67 (1990)]. Additional elements implicated in Hh signaling include the transcription factor CBP [Akimaru et al., *Nature* 386: 735–738 (1997)], the negative regulator slimb [Jiang and Struhl, *Nature* 391: 493–496 (1998)] and the SHh response element COUP-TFII [Krishnan et al., *Science* 278: 1947–1950 (1997)].

Mutants in Cos-2 are embryonicly lethal and display a phenotype similar to Hh over expression, including duplications of the central component of each segment and expansion domain of Hh responsive genes. In contrast, mutant embryos for fused and Ci show a phenotype similar to Hh loss of function including deletion of the posterior part of each segment and replacement of a mirror-like image duplication of the anterior part or each segment and replacement of a mirror-like duplication of the anterior part, Busson et al., *Roux. Arch. Dev. Biol.* 197: 221–230 (1988). Molecular characterizations of Ci suggested that it is a transcription factor which directly activates Hh responsive genes such as Wingless and Dpp, Alexandre et al., (1996) supra, Dominguez et al., (1996) supra. Likewise, molecular analysis of fused reveals that it is structurally related to serine threonine kinases and that both intact N-terminal kinase domain and a C-terminal regulatory region are required for its proper function, Preat et al., *Nature* 347: 87–9 (1990); Robbins et al., (1997), supra; Therond et al., *Proc. Natl.*

Acad. Sci. USA 93: 4224–8 (1996). Consistent with the putative opposing functions of Cos-2 and fused, fused mutations are suppressed by Cos-2 mutants and also by Suppressor of fused mutants, Preat et al., *Genetics* 135: 1047–62 (1993). However, whereas fused null mutations and N-terminal kinase domain mutations can be fully suppressed by Suppressor of fused mutations, C-terminus mutations of fused display a strong Cos-2 phenotype in a Suppressor of fused background. This suggests that the fused kinase domain can act as a constitutive activator of SHh signaling when Suppressor of Fused is not present. Recent studies have shown that the 92 kDa Drosophila fused, Cos-2 and Ci are present in a microtubule associated multiprotein complex and that Hh signaling leads to dissociation of this complex from microtubules, Robbins et al., *Cell* 90: 225–34 (1997); Sisson et al., *Cell* 90: 235–45 (1997). Both fused and Cos-2 become phosphorylated in response to Hh treatment, Robbins et al., supra; Therond et al., *Genetics* 142: 1181–98 (1996), but the kinase(s) responsible for this activity(ies) remain to be characterized. To date, the only known vertebrate homologues for these components are members of the Gli protein family (e.g., Gli-1, Gli-2 and Gli-3). These are zinc finger putative transcription factors that are structurally related to Ci. Among these, Gli-1 was shown to be a candidate mediator of the SHh signal [Hynes et al., *Neuron* 15: 35–44 (1995), Lee et al., *Development* 124: 2537–52 (1997); Alexandre et al., *Genes Dev.* 10: 2003–13 (1996)] suggesting that the mechanism of gene activation in response to Hh may be conserved between fly and vertebrates. To determine whether other signaling components in the Hh cascade are evolutionarily conserved and to examine the function of fused in the Hh signaling cascade on the biochemical level, Applicants have isolated and characterized the human fused cDNA. Tissue distribution on the mouse indicates that fused is expressed in SHh responsive tissues. Biochemical studies demonstrate that fused is a functional kinase. Functional studies provide evidence that fused is an activator of Gli and that a dominant negative form of fused is capable of blocking SHh signaling in Xenopus embryos. Together this data demonstrated that fused is directly involved in Hh signaling.

Applicants have identified a cDNA encoding a human fused (h fused) polypeptide and thus have provided for the first time a vertebrate fused molecule.

SUMMARY OF THE INVENTION

In one embodiment, the invention provides an isolated nucleic acid molecule having at least about 80% sequence identity to (a) a DNA molecule encoding a fused polypeptide comprising the sequence of amino acids 1 to 260 of FIG. 1 (SEQ ID NO. 24), or (b) the complement of the DNA molecule of (a); and encoding a polypeptide having fused biological activity. The sequence identity preferably is about 85%, more preferably about 90%, most preferably about 95%. In one aspect, the isolated nucleic acid has at least about 80%, preferably at least about 85%, more preferably at least about 90%, and most preferably at least about 95% sequence identity with a polypeptide having amino acid residues 1 to about 1315 of FIG. 1 (SEQ ID NO. 2). Preferably, the highest degree of sequence identity occurs within the kinase domain (amino acids 1 to about 260 (SEQ ID NO:24 as shown in FIG. 1). Especially preferred are those nucleic acid molecule containing a coding sequence for a lysine at amino acid position 33. In a further aspect, the isolated nucleic acid molecule comprises DNA encoding a human fused polypeptide having amino acid residues 1 to about 260 (SEQ ID NO: 24 as shown in FIG. 1). In yet another aspect, the invention provides for an isolated nucleic acid comprising DNA having at least a 95% sequence identity to (a) a DNA molecule encoding the same mature polypeptide encoded by the cDNA in ATCC Deposit No. 209637 (designation: pRK5tkneo.hFused-1272), alternatively the coding sequence of clone pRK5tkneo.hFused-1272, deposited under accession number ATCC 209637. In a still further aspect, the invention provides for a nucleic acid comprising human fused encoding sequence of the cDNA in ATCC deposit No. 209637 (designation: pRK5tkneo.hFused-1272) or a sequence which hybridizes thereto under stringent conditions.

In another embodiment, the invention provides a vector comprising DNA encoding a vertebrate fused polypeptide. A host cell comprising such a vector is also provided. By way of example, the host cells may be mammalian cells, (e.g. CHO cells), prokaryotic cells (e.g., *E. coli*) or yeast cells (e.g., *Saccharomyces cerevisiae*). A process for producing vertebrate fused polypeptides is further provided and comprises culturing host cells under conditions suitable for expression of vertebrate fused and recovering the same from the cell culture.

In yet another embodiment, the invention provides an isolated vertebrate fused polypeptide. In particular, the invention provides isolated native sequence vertebrate fused polypeptide, which in one embodiment is a human fused including an amino acid sequence comprising residues 1 to about 1315 of FIG. 1 (SEQ ID NO. 2). Human and other native vertebrate fused polypeptides with or without the initiating methionine are specifically included. Alternatively, the invention provides a vertebrate fused polypeptide encoded by the nucleic acid deposited under accession number ATCC 209637.

In yet another embodiment, the invention provides chimeric molecules comprising a vertebrate fused polypeptide fused to a heterologous polypeptide or amino acid sequence. An example of such a chimeric molecule comprises a vertebrate fused polypeptide fused to an epitope tag sequence or a constant region of an immunoglobulin.

In yet another embodiment, the invention provides an expressed sequence tag (EST) comprising the nucleotide sequences identified in FIG. 2 as 2515662 (SEQ ID NO. 3).

In yet another embodiment, the invention provides for compounds and methods for developing antagonists against and agonist promoting fused modulation of Hedgehog signaling. In particular, an antagonist of vertebrate fused which blocks, prevents, inhibits and/or neutralized the normal functioning of fused in SH signaling pathway, including both small bioorganic molecules and antisense nucleotides.

In yet another embodiment, the invention provides for alternatively spliced variants of human fused. In still yet a further embodiment, the invention provides a method of screening or assaying for identifying molecules that modulate the fused activation of hedgehog signaling. Preferably, the molecules either prevent interaction of fused with its associative complexing proteins or prevent or inhibit dissociation of complexes. The assay comprises the incubation of a mixture comprising fused and a substrate (e.g, Gli, COUP-TFII, slimb, CBP, MBP) with a candidate molecule and detection of the ability of the candidate molecule to modulate fused phosphorylation of its substrate. The screened molecules preferably are small molecule drug candidates. In particular, the method relates to a technique for screening for antagonists or agonists of fused biological activity comprising:

(a) exposing the fused expressing target cells in culture to a candidate compound; and (b) analyzing cell lysates to asses the level and/or identity of phosphorylation; or (c) scoring phenotypic or functional changes in treated cells; and comparing the results to control cells which were not exposed to the candidate compound.

In yet another embodiment, the method relates to a technique of diagnosing to determine whether a particular disorder is modulated by hedgehog signaling, comprising:

(a) culturing test cells or tissues;

(b) administering a compound which can inhibit fused modulated hedgehog signaling; and (c) measuring the degree of kinase attenuation on the fused substrate in cell lysates or hedgehog mediated phenotypic effects in the test cells.

BRIEF DESCRIPTION OF THE DRAWINGS

FIGS. 1A–1F show the nucleotide (SEQ ID NO. 1) and derived amino acid sequence (SEQ ID NO. 2) of native sequence of human fused polypeptide. Included are the kinase domain (residues 1 to about 260) (SEQ ID NO 24) and the ATP binding site at about amino acid position 33.

FIG. 2 shows the EST 2515662 (SEQ ID NO. 3) that was used in the cloning of the human full-length sequence.

FIGS. 3A–3E show a comparison between human and Drosophila fused (SEQ ID NOS. 2 and 23, respectively). Gaps introduced for optimal alignment are indicated by dashes. Identical amino acids are boxed. The lysine residue mutated in fused-DN (dominant negative) is the lysine (K) residue appearing at position 33.

FIGS. 4A–4F show the sequence of DNA28495 (SEQ ID NO. 4) that was an incorrectly spliced variant of human fused isolated from a fetal lung library. This clone contains a potential initiation methionine at position 116 followed by an open reading frame of 1944 bp A second open reading frame is present from about position 2295 to 4349. There is one nucleotide difference between clone DNA28495 (SEQ ID NO. 4) and clone DNA28494 (SEQ ID NO. 6) located in the first ORF at position 1863 of clone 28495 (SEQ ID NO. 4) (A vs. G) which changes the encoded sequence at amino acid position 583 from Gln to Arg, respectively. The first open reading frame of DNA28494 (SEQ ID NO. 6) starts at residue 115 and is followed by a 647 amino acid long open reading frame.

FIGS. 5A–5F show sequence of DNA28494 (SEQ ID NO. 6) that was another incorrectly spliced variant of human fused isolated from a fetal lung library.

FIG. 6 is a western blot of the PCR product of an epitope tag of DNA28495 (SEQ ID NOS. 5 & 21) and DNA28494 (SEQ ID NOS. 7 & 22). A specific band of 150 kDa was detected in the cell pellet of cells transfected with the construct corresponding to clone DNA28494 (SEQ ID NO. 6) and a specific band of approximately 100 kDa could be detected for clone DNA28495 (SEQ ID NO. 4) (FIG. 6). These bands were not present in the mock transfected control. The presence of the 100 kDa band suggests the two open reading frames of DNA28494 (SEQ ID NO. 6) can be spliced together to direct the synthesis of a large protein of 150 kDa. The absence of this band for DNA28495 (SEQ ID NO. 4) suggested that this clone apparently cannot be correctly spliced.

FIG. 7 is a northern blot analysis of human fused (SEQ ID NO 1). Multiple human fetal and adult tissue northern blots were probes with a human fused cDNA probe.

FIGS. 8A–8F show is a photograph showing in situ hybridization of embryonic and adult tissues with fused (SEQ ID NO 1). Sagittal sections of E11.5 (FIG. 8A) and E13.5 (FIG. 8B) mouse embryos. Coronal section through the spinal chord of E11.5 (FIG. 8C) and E13.5 (FIG. 8D) mouse embryo. Sagittal section through P1 (FIG. 8E) and adult (FIG. 8F) mouse. Cp, choroid plexus; hb, hindbrain; hip, hippocampal formation; ht, heart; hy, hypothalamus; kd, kidney; lg, lung; mb, midbrain; md, midgut; mnd, mandibular component of first branchial arch; sc, spinal cord; st, stomach; tec, midbrain tectum; vh, ventral horn of spinal cord; vm, ventral midbrain. Scale bars: FIG. 8A, 1.0 mm; FIG. 8B, 1.62 mm; FIG. 8C, 0.14 mm; FIG. 8D, 0.17 mm; FIG. 8E, 2.0 mm; and FIG. 8F, 3.1 mm.

FIGS. 9A–9C are a photograph showing in situ hybridization showing the presence of fused mRNA in high levels in the adult mouse testes (FIG. 9A). High magnification reveals differences in levels of expression within seminiferous tubules (FIG. 9C). Hybridization of the testis with a sense strand control probe to fused gave no hybridization (FIG. 9B).

FIGS. 10A–10B are a bar graph representing the activation of Gli by fused. (FIG. 10A): C3H10T1/2 cells were cotransfected with a p9XGliLus, ptkRenilla luciferase and fused or various fused mutants. Cells were harvested 48h after transfection and the luciferase activity was assayed as described in Example 7. (FIG. 10B); Fused transactivation of a Gli reporter construct. C3H10T1/2 cells were cotransfected with a p9XGliLuc reporter construct, ptkRenilla luciferase and a CMV driven expression vector for fused or various fused mutants. Cells were harvested 48 hours after transfection and the luciferase activity was assayed as described in the Examples. The data represents the mean of duplicative determinations.

FIGS. 11A–11E are a photograph showing that fused-DN (SEQ ID NO 25) inhibits SHh signaling in early Xenopus development. Depicted are: (FIG. 11A) Dorsal view of tadpole stage embryos. Top embryo is fused-DN (SEQ ID NO 25) injection and bottom embryo is the control; (FIG. 11B) Side view of tadpole stage embryo. Top embryo is fused-DN (SEQ ID NO 25) injection and bottom embryo is the control; (FIGS. 11C & 11D) Pax-6 staining of stage 16 neurula embryos injected with control DNA and fused-DN (SEQ ID NO 25), respectively; (FIG. 11E) SHh expression in the floor plate of neurula stage control embryo (left) or fused-DN (SEQ ID NO 25) injected embryo (right).

FIG. 12 is a photograph which confirms the kinase activity of fused (SEQ ID NO 2) and its activation of Gli. Depicted are 293 cells transfected with HA tagged fused constructs as indicated in Example 10 and immunoprecipitated with anti-HA antibodies and protein A sepharose. Protein A beads were subjected to in vitro kinase assay as described in Example 10 in the presence of MBP.

DETAILED DESCRIPTION OF THE PREFERRED EMBODIMENTS

I. Definitions

The terms "vertebrate fused" and "vertebrate fused polypeptide" when used herein encompass native sequence vertebrate fused and vertebrate fused variants (which are further defined herein) having fused biological activity. Fused may be isolated from a variety of sources, such as from human tissue types or from another source, or prepared by recombinant or synthetic methods.

A "native sequence vertebrate fused" comprises a polypeptide having the same amino acid sequence as a vertebrate fused derived from nature. Such native sequence vertebrate fused can be isolated from nature or can be produced by recombinant and/or synthetic means. The term "native sequence vertebrate fused" specifically encompasses naturally occurring truncated forms of vertebrate fused, naturally occurring variant forms (e.g., alternatively spliced forms) and naturally-occurring allelic variants of vertebrate fused. Native vertebrate fused includes e.g., fused in mammals such as human, murine, bovine, porcine, equine, feline, canine, etc., and preferably refers to human. Thus, one embodiment of the invention, the native sequence human vertebrate fused is a mature or full-length native human vertebrate fused comprising amino acids 1 to 1315 of SEQ ID NO: 2 as shown in FIG. 1 with or without the initiating methionine at position 1.

"Vertebrate fused variant" means an active vertebrate fused as defined below having at least about 80% amino acid sequence identity to (a) a DNA molecule encoding a vertebrate fused polypeptide, or (b) the complement of the DNA molecule of (a). In a particular embodiment, the vertebrate fused variant has at least about 80% amino acid sequence homology with the vertebrate fused having the deduced amino acid sequence (SEQ ID NO:2) shown in FIG. 1 for a full-length native sequence vertebrate fused. Such vertebrate fused variants include, without limitation, vertebrate fused polypeptides wherein one or more amino acid residues are added, or deleted, at the N- or C-terminus of the sequence of FIG. 1 (SEQ ID NO 2). Preferably, the nucleic acid or amino acid sequence identity is at least about 85%, more preferably at least about 90%, and even more preferably at least about 95%.

"Percent (%) amino acid sequence identity" with respect to the vertebrate fused sequences identified herein is defined as the percentage of amino acid residues in a candidate sequence that are identical with the amino acid residues in the vertebrate fused sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. "Percent (%) nucleic acid sequence identity" with respect to the vertebrate fused sequences identified herein is defined as the percentage of nucleotides in a candidate sequence that are identical with the nucleotides in the vertebrate fused sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The term "epitope tagged" when used herein refers to a chimeric polypeptide comprising vertebrate fused polypeptide, or a portion thereof, fused to a "tag polypeptide". The tag polypeptide has enough residues to provide an epitope against which an antibody can be made, yet is short enough such that it does not interfere with activity of the vertebrate fused polypeptide. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

As used herein, the term "immunoadhesin" designates antibody-like molecules which combine the binding specificity of a heterologous protein (an "adhesin") with the effector functions of immunoglobulin constant domains. Structurally, the immunoadhesin comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesins may be obtained from any immunoglobulin, such as IgG-1, IgG-2, IgG-3 or IgG-4 subtypes, IgA (including IgA-1 and IgA-2, IgE, IgD or IgM. Immunoadhesion reported in the literature include fusions of the T cell receptor* [Gascoigne et al., Proc. Natl. Acad. Sci. USA 84: 2936–2940 (1987)]; CD4* [Capron et al., Nature 337: 525–531 (1989Traunecker et al., Nature 339: 68–70 (1989); Zettmeissl et al., DNA Cell Biol. USA 9: 347–353 (1990); Byrn et al., Nature 344, 667–670 (1990)]; L-selectin (homing receptor) [Watson et al., J. Cell. Biol. 110, 2221–2229 (1990); Watson et al., Nature 349, 164–167 (1991)]; CD44* [Aruffo et al., Cell 61, 1303–1313 (1990)]; CD28* and B7* [Linsley et al., J. Exp. Med. 173 721–730 (1991)]; CTLA-4* [Lisley et al., J. Exp. Med. 174, 561–569 (1991)]; CD22* [Stamenkovic et al., Cell 66. 1133–1144 (1991)]; TNF receptor [Ashkenazi et al., Proc. Natl. Acad. Sci USA 88, 10535–10539 (1991); Lesslauer et al., Eur. J. Immunol. 27, 2883–2886 (1991); Peppel et al., J. Exp. Med. 174, 1483–1489 (1991)]; NP receptors [Bennett et al., J. Biol. Chem. 266, 23060–23067 (1991) IgE receptor α-chain* [Ridgway and Gorman, J. Cell. Biol. 115, abstr. 1448 (1991)]; HGF receptor [Mark, M. R. et al., 1992, submitted], where the asterisk (*) indicates that the receptor is member of the immunoglobuln superfamily.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends upon the ability of denatured DNA to reanneal when complementary strands are present in an environment near but below their $T^m$ (melting temperature). The higher the degree of desired homology between the probe and hybridizable sequence, the higher the relative temperature which can be used. As a result, it follows that higher relative temperatures would tend to make the reaction conditions more stringent, while lower temperatures less so. Moreover, stringency is also inversely proportional to salt concentrations. For additional details and explanation of stringency of hybridization reactions, see Ausubel et al., Current Protocols in Molecular Biology (1995).

"Stringent conditions," as defined herein may be identified by those that: (1) employ low ionic strength and high. temperature for washing, for example 0.015 M sodium chloride/0.0015 M sodium citrate/0.1% sodium dodecyl sulfate at 50° C.; (2) employ during hybridization a denaturing agent, such as formamide, for example, 50% (vol/vol)

formamide with 0.1% bovine serum albumin/0.1% Ficoll/ 0.1% polyvinylpyrrolidone/50 mM sodium phosphate buffer at pH 6.5 with 750 mM sodium chloride, 75 mM sodium citratp at 42° C.; (3) employ 50% formamide, 5×SSC (0.75 M NaCl, 0.075 M sodium citrate), 5Q mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual (New York: Cold Spring Harbor Laboratory Press, 1989), and include the use of a washing solution and hybridization conditions (e.g., temperature, ionic strength and %SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the vertebrate fused natural environment will not be present. Ordinarily, however, isolated polypeptide will be prepared by at least one purification step.

An "isolated" vertebrate fused nucleic acid molecule is a nucleic acid molecule that is identified and separated from at least one contaminant nucleic acid molecule with which it is ordinarily associated in the natural source of the vertebrate fused nucleic acid. An isolated vertebrate fused nucleic acid molecule is other than in the form or setting in which it is found in nature. Isolated vertebrate fused nucleic acid molecules therefore are distinguished from the corresponding native vertebrate fused nucleic acid molecule as it exists in natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single monoclonal antibodies (including agonist and antagonist antibodies), antibody compositions with polyeptopic specificity, as well as antibody fragments (e.g., Fab, F(ab')$_2$ and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [U.S. Pat. No. 4,816,567; Cabilly et al.; Morrison et al., *Proc. Natl. Acad. Sci. USA* 81 6851–6855 (1984)].

"Humanized" forms of non-human (e.g. murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, corresponding non-human residues replace Fv framework residues of the human immunoglobulin.

Furthermore, humanized antibody may comprise residues that are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522–525 (1986); Reichmann et al., *Nature* 332, 323–329 (1988); Presta, *Curr. Op. Struct. Biol.* 2 593–596 (1992) and U.S. Pat. No. 5,225,539 (Winter) issued Jul. 6, 1993.

"Active" or "activity" for the purposes herein refers to form(s) of vertebrate fused which retain the biologic and/or immunologic activities of native or naturally occurring vertebrate fused. A preferred activity is the ability to bind to and affect, e.g., block or otherwise modulate, hedgehog signaling. The activity preferably involves the regulation of the pathogenesis of Basal cell carcinoma. Another preferred biological activity is the ability to phosphorylate or modulate the phosphorylation of Gli.

The term "antagonist" is used herein in the broadest sense to include any molecule which blocks, prevents, inhibits, neutralizes the normal functioning of fused in the Hh signaling pathway. One particular form of antagonist includes a molecule that interferes with the interaction between used and its binding or complexing proteins. In a similar manner, the term "agonist" is used herein to include any molecule which promotes, enhances or stimulates the normal functioning of fused in the Hh signaling pathway. Suitable molecules that affect the protein-protein interaction of fused and its binding proteins include fragments of the latter or small bioorganic molecules, e.g., peplidornimetics, which will prevent or enhance, as the case may be, the interaction of proper complex formation. Non-limiting examples include proteins, peptides, glycoproteins, glycopeptides, glycolipids, polysaccharides, oligosacchrides, nucleic acids, bioorganic molecules, peptidomimetics, pharmacological agents and their metabolites, transcriptional and translation control sequences, and the like. Another preferred form of antagonist includes antisense nucleotides that inhibit proper transcription of wild type fused. Preferred forms of antagonists are small molecules, which specifically bind to or block binding of the ATP binding site of fused.

The term "modulation" or "modulating" means upregulation or downregulation of a signaling pathway. Cellular processes under the control of signal transduction may include, but are not limited to, transcription of specific genes; normal cellular functions, such as metabolism, proliferation, differentiation, adhesion, apoptosis and survival, as well as abnormal processes, such as transformation, blocking of differentiation and metastasis.

The techniques of "polymerase chain reaction," or "PCR", as used herein generally refers to a procedure wherein minute amounts of a specific piece of nucleic acid, RNA and/or DNA are amplified as described in U.S. Pat. No. 4,683,195 issued Jul. 28. 1987. Generally, sequence information from the ends of the region of interest or beyond needs to be available, such that oligonucleotide primers can be designed; these primer will be identical or similar in sequence to opposite strands of the template to be amplified. The 5' terminal nucleotides of the two primers may coincide with the ends of the amplified material. PCR sequences form total genomic DNA, and cDNA transcribed from total cellular RNA, bacteriophage, or plasmid sequences, etc. See generally Mullis et al., *Cold Spring Harbor Symp. Quant. Biol.* 51: 263 (1987); Erlich, Ed., PCR Technology, (Stockton Press, NY, 1989). As used herein, PCR is considered to be one, but not the only, example of a nucleic acid test sample comprising the use of a known nucleic acid as a primer and a nucleic acid polymerase to amplify or generate a specific piece of nucleic acid.

II. Compositions and Methods of the Invention

A. Full-length Vertebrate Fused

The present invention provides newly identified and isolated nucleotide sequences encoding polypeptides referred to in the present application as human and vertebrate fused. In particular, Applicants have identified and isolated cDNA encoding a vertebrate fused polypeptide, as disclosed in further detail in the Examples below. Using BLAST, BLAST-2 and FastA sequence alignment computer programs, Applicants found that a full-length native sequence human fused (shown in FIG. 3 (SEQ ID NO 2)) has 28% amino acid sequence identity with Drosophila fused (SEQ ID NO 23). Accordingly, it is presently believed that the human fused disclosed in the present application is a newly identified member of the hedgehog signaling cascade.

The full-length native sequence of human vertebrate fused gene, or portions thereof, may be used as hybridization probes for a cDNA library to isolate the full-length gene or to isolate still other vertebrate homolog genes (for instance, those encoding naturally-occurring variants of vertebrate fused or vertebrate fused from other species) which have a desired sequence identity to the vertebrate fused sequence disclosed in FIG. 1 (SEQ ID NO 1). Optionally, the length of the probes will be about 20 to about 50 bases. The hybridization probes may be derived from the nucleotide sequence of FIG. 1 (SEQ ID NO 1) or from genomic sequences including promoters, enhancer elements and introns of native sequence vertebrate fused. By way of example, a screening method will comprise isolating the coding region of the vertebrate fused gene using the known DNA sequence to synthesize a selected probe of about 40 bases. Hybridization probes may be labeled by a variety of labels, including radionucleotides such as $^{32}$p or $^{35}$S, or enzymatic labels such as alkaline phosphatase coupled to the probe via avidin/biotin coupling systems. Labeled probes having a sequence complementary to that of the vertebrate fused gene of the present invention can be used to screen libraries of human cDNA, genomic DNA or mRNA to determine which members of such libraries the probe hybridizes to.

B. Vertebrate Fused Variants

In addition to the full-length native sequence vertebrate fused described herein, it is contemplated that vertebrate fused variants can be prepared. Vertebrate fused variants can be prepared by introducing appropriate nucleotide changes into a known vertebrate fused DNA, or by synthesis of the desired vertebrate fused polypeptides. Those skilled in the art will appreciate that amino acid changes may alter post-translational processes of the vertebrate fused.

Variations in the native full-length sequence vertebrate fused or in various domains of the vertebrate fused described herein, can be made, for example, using any of the techniques and guidelines for conservative and non-conservative mutations set forth, for instance, in U.S. Pat. No. 5,364,934. Variations may be a substitution, deletion or insertion of one or more codons encoding the vertebrate fused that results in a change in the amino acid sequence of the vertebrate fused as compared with the native sequence vertebrate fused. Optionally the variation is by substitution of at least one amino acid with any other amino acid in one or more of the domains of the vertebrate fused. Guidance in determining which amino acid residue may be inserted, substituted or deleted without adversely affecting the desired activity may be found by comparing the sequence of the vertebrate fused with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the vertebrate fused variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, The Proteins, (W. H. Freeman & Co., N.Y.); Chothia, *J. Mol. Biol.*, 150:1 (1976)]. If alanine substitution does not yield adequate amounts of variant, an isoteric amino acid can be used.

In the human fused sequence depicted in FIG. 1, the kinase domain is represented by amino acid residues 1–260 (SEQ ID NO 24) of which position lysine 33 appears to be necessary for ATP binding and thus enzymatic activity.

C. Modifications of Vertebrate Fused

Covalent modifications of vertebrate fused are included within the scope of this invention. One type of covalent modification includes reacting targeted amino acid residues of the vertebrate fused with an organic derivatizing agent that is capable of reacting with selected side chains or the N- or C- terminal residues of the vertebrate fused. Derivatization with bifunctional agents is useful, for instance, for crosslinking vertebrate fused to a water-insoluble support matrix or surface for use in the method for purifying anti-vertebrate fused antibodies, and vice-versa. Commonly used crosslinking agents include, e.g., 1,1-bis(diazo-acetyl)-2-phenylethane, glutaraldehyde, N-hydroxy-succinimide esters, for example, esters with 4-azido-salicylic acid, homobifunctional imidoesters, including disuccinimidyl esters such as 3,3'-dithiobis-(succinimidyl-propionate), bifunctional maleimides such as bis-N-maleimido-1,8-octane and agents such as methyl-3-[(p-azidophenyl)-dithio]propioimi-date.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of vertebrate fused comprises linking the vertebrate fused polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337. Such modifications would be expected in increase the half-life of the molecules in circulation in a mammalian system; Extended half-life of fused molecules might be useful under certain circumstances, such as where the fused variant is administered as a therapeutic agent.

The vertebrate fused of the present invention may also be modified in a way to form a chimeric molecule comprising vertebrate fused bonded to another, heterologous polypeptide or amino acid sequence. In one embodiment, such a chimeric molecule comprises a fusion of the vertebrate fused with a tag polypeptide, which provides an epitope to which an anti-tag antibody can selectively bind. The epitope tag is generally placed at the amino- or carboxyl- terminus of the vertebrate fused. The presence of such epitope-tagged forms of the vertebrate fused can be detected using an antibody against the tag polypeptide. Also, provision of the epitope tag enables the vertebrate fused to be readily purified by affinity purification using an anti-tag antibody or another type of affinity matrix that binds to the epitope tag. In an alternative embodiment, the chimeric molecule may comprise a fusion of the vertebrate fused with an immunoglobulin or a particular region of an immunoglobulin. For a bivalent form of the chimeric molecule, such a fusion could be to the Fc region of an IgG molecule. Ordinarily, the C-terminus of a contiguous amino acid sequence of a ligand-(IFN-γ-) binding domain of an IFN-γ receptor is fused to the N-terminus of a contiguous amino acid sequence of an immunoglobulin constant region, in place of the variable region(s), however N-terminal fusions are also possible.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, immunoadhesins may be synthesized according to known methods.

The precise site at which the fusion is made is not critical; particular sites are well known and may be selected in order to optimize the biological activity, secretion or binding characteristics of the immunoadhesins.

In a preferred embodiment, the C-terminus of a contiguous amino acid sequence which comprises the binding site(s) for IFN-γ is fused, at the N-terminal end, to the C-terminal portion of an antibody (in particular the Fc domain), containing the effector functions of an immunoglobulin, e.g. immunoglobulin $G_1$ (IgG-1). As hereinabove mentioned, it is possible to fuse the entire heavy chain constant region to the sequence containing the binding site(s). However, more preferably, a sequence beginning in the hinge region just upstream of the papain cleavage site (which defines IgG Fc chemically; residue 216, taking the first residue of heavy chain constant region to be 114 [Kobet et al., supra], or analogous sites of other immunoglobulins) is used in the fusion. Although it was earlier thought that in immunoadhesins the immunoglobulin light chain would be required for efficient secretion of the heterologous protein-heavy chain fusion proteins, it has been found that even the immunoadhesins containing the whole IgG1 heavy chain are efficiently secreted in the absence of light chain. Since the light chain is unnecessary, the immunoglobulin heavy chain constant domain sequence used in the construction of the immunoadhesins of the present invention may be devoid of a light chain binding site. This can be achieved by removing or sufficiently altering immunoglobulin heavy chain sequence elements to which the light chain is ordinarily linked so that such binding is no longer possible. Thus, the CH1 domain can be entirely removed in certain embodiments of the IFN-γ receptor-immunoglobulin chimeras.

In a particularly preferred embodiment, the amino acid sequence containing the extracellular domain of an IFN-γ receptor is fused to the hinge region and CH2, CH3; or CH1, hinge, CH2 and CH3 domains of an IgG-1, IgG-2, IgG-3, or IgG-4 heavy chain. The construction of a typical structure is disclosed in Example 1.

In some embodiments, the IFN-γ receptor-immunoglobulin molecules (immunoadhesins) are assembled as monomers, dimers or multimers, and particularly as dimers or tetramers. Generally, these assembled immunoadhesins will have known unit structures similar to those of the corresponding immunoglobulins. A basic four chain structural unit (a dimer of two immunoglobulin heavy chain-light chain pairs) is the form in which IgG, IgA and IgE exist. A four chain unit is repeated in the high molecular weight immunoglobulins; IgM generally exists as a pentamer of basic four-chain units held together by disulfide bonds. IgA globulin, and occasionally IgG globulin, may also exist in a multimeric form in serum. In the case of multimers, each four chain unit may be the same or different.

It is not necessary that the entire immunoglobulin portion of the IFN-γ receptor-immunoglobulin chimeras be from the same immunoglobulin. Various portions of different immunoglobulins may be combined, and variants and derivatives of native immunoglobulins can be made as hereinabove described with respect to IFN-γ, in order to optimize the properties of the immunoadhesin molecules. For example, immunoadhesin constructs in which the hinge of IgG-1 was replaced with that of IgG-3 were found to be functional and showed pharmacokinetics comparable to those of immunoadhesins comprising the entire IgG-1 heavy chain.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., Bio Technology, 6:1204–1210 (1988)]; the KT3 epitope peptide [Martin et al., Science 255:192–194 (1992)]; an α-tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)]. A preferred tag is the influenza HA tag.

D. Preparation of Vertebrate Fused

The description below relates primarily to production of a particular vertebrate fused by culturing cells transformed or transfected with a vector containing vertebrate fused nucleic acid. It is, of course, contemplated that alternative methods, which are well known in the art, may be employed to prepare vertebrate fused. For instance, the vertebrate fused sequence, or portions thereof, may be produced by direct peptide synthesis using solid-phase techniques [see, e.g., Stewart et al., Solid-Phase Peptide Synthesis, W. H. Freeman Co., San Francisco, Calif. (1969); Merrifield, J. Am. Chem. Soc., 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the vertebrate fused may be chemically synthesized separately and combined using chemical or enzymatic methods to produce the full-length vertebrate fused.

1. Isolation of DNA Encoding Vertebrate Fused

DNA encoding vertebrate fused may be obtained from a cDNA library prepared from tissue believed to possess the vertebrate fused mRNA and to express it at a detectable level. Accordingly, human vertebrate fused DNA can be conveniently obtained from a cDNA library prepared from human tissue, such as described in the Examples. The vertebrate fused-encoding gene may also be obtained from a genomic library or by oligonucleotide synthesis.

Libraries can be screened with probes (such as antibodies to the vertebrate fused or oligonucleotides of at least about 20–80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding vertebrate used is to use PCR methodology [Sambrook et al., supra; Dieffenbach et al., PCR Primer: A Laboratory Manual (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for vertebrate fused production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 June 1989. For mammalian cells without such cell walls, the calcium phosphate precipitation method of Graham and van der Eb, *Virology* 52:456457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for vertebrate fused-encoding vectors. *Saccharomyces cerevisiae* is a commonly used lower eukaryotic host microorganism.

Suitable host cells for the expression of vertebrate fused are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding vertebrate fused may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques, which are known to the skilled artisan.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells. A preferred replicable expression vector is the plasmid is pRK5. Holmes et al., *Science*, 253:1278–1280 (1991).

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the vertebrate fused nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the vertebrate fused nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci USA*, 80:21–25 (1983)]. Promoters for use in bacterial systems also will contain a Shine-Dalgarno (S.D.) sequence operably linked to the DNA encoding vertebrate fused.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Vertebrate fused transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Inserting an enhancer sequence into the vector may increase transcription of a DNA encoding the vertebrate fused by higher eukaryotes. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the vertebrate fused coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding vertebrate fused.

Still other methods, vectors, and host cells suitable for adaptation to the synthesis of vertebrate fused in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence vertebrate fused polypeptide or against a synthetic peptide based on the DNA sequences provided herein or against exogenous sequence fused to vertebrate fused DNA and encoding a specific antibody epitope.

5. Purification of Polypeptide

Forms of vertebrate fused may be recovered from host cell lysates. If membrane-bound, it can be released from the membrane using a suitable detergent solution (e.g. Triton-X 100) or by enzymatic cleavage. Cells employed in expression of vertebrate fused can be disrupted by various physical or chemical means, such as freeze-thaw cycling, sonication, mechanical disruption, or cell lysing agents.

It may be desired to purify vertebrate fused from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the vertebrate fused. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular vertebrate fused produced.

E. Uses for Vertebrate Fused (1) Fused is Universal Mediator of Hh Signaling

The human fused full length molecule of (FIG. 1 (SEQ ID NO 1)) encodes a protein with a predicted molecular weight of 150 kDa, which is significantly larger that Drosophila fused (100 kDa, d fused (SEQ ID NO 23)). Human fused (h fused) shows notable homology to the Drosophila homologue in the kinase domain, but little homology with doused or any other known protein over the remaining ≈1000 amino acids. The kinase domain extends from residue 1 to about residue 260, as is represented in FIG. 1 (SEQ ID NOS. 24 & 2). This divergence at the C-terminus of the molecules is unexpected given that the C-terminus of the Drosophila molecule is required for its activity, Preat et al., *Nature* 347: 87–9 (1990). An ATP binding site is at about amino acid position 33 and is required for kinase activity.

Prior studies in Drosophila indicate that d fused is necessary for Hh signal to occur but have not addressed the issue whether fused is sufficient to activate this signaling system. As depicted in the Examples, applicants have herein used a Gli DNA binding element present in the HNF3β promoter, in front of a luciferase mediator of the Hh cascade, which clearly demonstrates that fused alone is capable of activating Gli mediated transcription in this system. It is further apparent that both an intact kinase domain and an intact C-terminal non-catalytic domain are required for this activation, which supports the notion that fused functions as a kinase and that the C-terminus may play a role in the substrate recognition or in regulating the kinase activity.

Applicants have shown in the present application that h fused is a kinase which is capable of phosphorylating artificial substrates such as MBP. However, the identity of the physiological substrate for h fused remains to be determined. One obvious candidate is Gli-1 itself, as Gli-1 phosphorylation by h fused can be detected in vitro.

To determine if human fused is essential for Hh signaling in vertebrates, a mutant was constructed by altering a conserved lysine in the ATP binding site (about amino acid residue 33). Typically, such mutants act as inhibitor of the corresponding wild type kinase by blocking access to substrate and/or regulatory factors, He et al., *Nature* 374, 617–22 (1995). When overexpressed in 2-cell stage Xenopus embryos, the most remarkable phenotype was the presence of fused eyes in about 30% of the injected embryos. Several lines of evidence indicate that this phenotype is likely to result from the inhibition of Hh signaling. First, SHh knockouts display a cyclopia phenotype attributed recently to mutations in the SHh gene, Chiang et al., *Nature* 383: 407–13 (1996). Second, zebrafish embryos (cyclops) with reduced expression of SHh or injected with constitutively active form of PKA, a negative regulator of the Hh pathway are cyclops. Third, SHh, emanating from prechordal plate, has been shown to inhibit expression of Pax-6, a key transcription factor required for eye development, in the center of a continuous eyefield, Ekker et al., *Curr. Biol.* 5: 944–55 (1995); Li et al., *Development* 124: 603–15 (1997); Macdonald et al., *Development* 121: 3267–78 (1995). Finally, staining for Pax-6 embryos injected with fused-DN revealed a single field of expression suggesting a failure of SHh emanating from the prechordal plate to downregulate the expression of Pax-6 at the center of the eyefield.

To confirm the position of fused in the Hh signaling pathway, expression of SHh in the floor plate of Xenopus embryos injected with h fused-DN could be rescued by coinjection of Gli-1. This suggests that fused acts in association with Gli in the SHh signaling pathway.

The tissue distribution of fused shows that it is expressed in all SHh responsive cells. In particular, its expression pattern overlaps well with Ptch, the binding component of the Hh receptor which is itself a target gene of the SHh signaling pathway. These data suggest that fused is involved in mediating a wide variety of effect SHh has on different tissues. Functionally, this was observed again in frog embryos where, fused-DN inhibited eye development as well as SHh expression in the floor plate.

hFused-DN also appears to affect normal development of tissues such as the frog gut which is regulated by Indian Hh. This, combined with the fact that fused is expressed in the gut and testis, sites of IHh and DHh action respectively, suggest that fused may be a universal mediator of signaling for all members of the Hh protein family.

Very high levels of fused mRNA was found on germ cell, the development of which appears to be regulated by DHh. Homozygous mutant mice for DHh fail to develop germ cells and are viable but sterile (Bitgood et al., *Curr. Biol.* 6: 298–304 (1996). However, Patched, a Hedgehog receptor is expressed on interstitial Leydig cells and not on germ cells where fused is expressed, Bitgood et al., supra. This discrepancy suggests that there may be additional hedgehog receptors.

Applicants have shown in the Examples that wild type h fused is capable of activating Gli in a reporter assay. Furthermore, expression of SHh in the floor plate of frog embryos injected with h fused-DN could be rescued by coinjection of Gli-1. Taken together these observations are consistent with the assertion that fused acts downstream of Smo and upstream of Gli in this signaling pathway, which is consistent with the genetic evidence in Drosophila to date.

(2) General uses for Vertebrate Fused

Nucleotide sequences (or their complement) encoding vertebrate fused have various applications in the art of molecular biology, including uses as hybridization probes, in chromosome and gene mapping and in the generation of anti-sense RNA and DNA. Vertebrate fused nucleic acid will also be useful for the preparation of vertebrate fused polypeptides by the recombinant techniques described herein.

The full-length native sequence vertebrate fused gene, or portions thereof, may be used as hybridization probes for a cDNA library to isolate the full-length gene or to isolate still other genes (for instance, those encoding naturally-occurring variants of vertebrate fused or vertebrate fused from other species) which have a desired sequence identity to the vertebrate fused sequence disclosed in FIG. 1 (SEQ ID NO 1). Optionally, the length of the probes will be about 20 to about 50 bases. The hybridization probes may be derived from the nucleotide sequence of FIG. 1 (SEQ ID NO 1) or from genomic sequences including promoters, enhancer elements and introns of native sequence vertebrate fused. By way of example, a screening method will comprise isolating the coding region of the vertebrate fused gene using the known DNA sequence to synthesize a selected probe of about 40 bases. Hybridization probes may be labeled by a variety of labels, including radionucleotides such as $^{32}$P or $^{35}$S, or enzymatic labels such as alkaline phosphatase coupled to the probe via avidin/biotin coupling systems. Labeled probes having a sequence complementary to that of the vertebrate fused gene of the present invention can be used to screen libraries of human cDNA, genomic DNA or mRNA to determine to which members of such libraries the probe hybridizes. Hybridization techniques are described in further detail in the Examples below.

The probes may also be employed in PCR techniques to generate a pool of sequences for identification of closely related vertebrate fused sequences.

Nucleotide sequences encoding a vertebrate fused can also be used to construct hybridization probes for mapping the gene, which encodes vertebrate fused and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Vertebrate fused polypeptides can be used in assays to identify the other proteins or molecules involved in complexing with fused which ultimately results in the modulation of hedgehog signaling. Alternatively, these molecules can modulate the fused kinase phosphorylation of its substrate. By such method's, inhibitors of the binding interaction can be identified. Proteins involved in such binding interactions can also be used to screen for peptide or small molecule inhibitors or agonists of the binding interaction.

Also, the substrate of vertebrate fused can be used to isolate correlative complexing proteins. Screening assays can be designed to find lead compounds that mimic the biological activity of a native vertebrate fused or to find those that act as a substrate for vertebrate fused. Such screening assays will include assays amenable to high-throughput screening of chemical libraries, making them particularly suitable for identifying small molecule drug candidates. Such small molecule inhibitors could block the enzymatic action of fused, and thereby inhibit hedgehog signaling. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode vertebrate fused or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding vertebrate fused can be used to clone genomic DNA encoding vertebrate fused in accordance with established techniques and the genomic sequences used to generate transgenic animals that contain cells which express DNA encoding vertebrate fused. Methods for generating transgenic animals, particularly animals such as mice or rats, have become conventional in the art and are described, for example, in U.S. Pat. Nos. 4,736,866 and 4,870,009. Typically, particular cells would be targeted for vertebrate fused transgene incorporation with tissue-specific enhancers. Transgenic animals that include a copy of a transgene encoding vertebrate fused introduced into the germ line of the animal at an embryonic stage can be used to examine the effect of increased expression of DNA encoding vertebrate fused. Such animals can be used as tester animals for reagents thought to confer protection from, for example, pathological conditions associated with its overexpression. For example, for basal cell carcinoma, fused can be overexpressed in the basal cell layer of the skin using a Keratin 5 or 14 promoter. In accordance with this facet of the invention, an animal is treated with the reagent and a reduced incidence of the pathological condition, compared to untreated animals bearing the transgene, would indicate a potential therapeutic intervention for the pathological condition.

Non-human homologues of vertebrate fused can be used to construct a vertebrate fused "knock out" animal which has a defective or altered gene encoding vertebrate fused as a result of homologous recombination between the endogenous gene encoding vertebrate fused and altered genomic DNA encoding vertebrate fused introduced into an embryonic cell of the animal. For example, cDNA encoding vertebrate fused can be used to clone genomic DNA encoding vertebrate fused in accordance with established techniques. A portion of the genomic DNA encoding vertebrate fused can be deleted or replaced with another gene, such as a gene encoding a selectable marker that can be used to monitor integration. Typically, several kilobases of unaltered flanking DNA (both at the 5' and 3' ends) are included in the vector [see e.g. Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see eg., Li et al., Cell, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the vertebrate fused polypeptide.

As fused has been implicated as a universal mediator for all members of the Hh family (SHh, IHh, DHh), disease states or disorders which are associated with general Hh signaling, would also be treatable with fused and antagonists and agonists thereof For example, SHh activation (e.g. fused agonists) has recently been promoted as a treatment for various degenerative disorders of the nervous system, e.g., Parkinson's disease, memory deficits, Alzheimer's disease, Lou Gebrig's disease, Huntington's disease, schizophrenia, stroke and drug addiction. Recent studies suggest that Dhh mutant males are infertile due to the failure of spermatocytes to complete their differentiation into mature sperm, Bitgood et al., *Curr. Biol.* 6: 298–304 (1996); Bitgood et al., *Dev. Biol.* 172: 126–138 (1995). Additionally, fused agonists could be used to great gut diseases, bone diseases, skin diseases, diseases of the testis, ulcers, lung diseases, diseases of the pancreas, diabetes, osteoporosis.

The presence of the protein kinase domain suggests that fused may act similarly as members of the protein kinase family in the modulation of Hh signaling. Protein kinases are essential elements of regulatory circuits in differentiated as well as growing cells; Preat et al., *Nature* 347: 87–89 (1990). Many of these enzyme are involved in transduction of extracellular signals and operate through a cascade of phosphorylation events that amplify and disseminate the effects of a primary signal. As described earlier, Drosophila fused bears significant homology to other intracellular serine/threonine kinases. Many serine/threonine kinases are implicated in cell-cycle control in yeasts and in mammals, Hunter, *Cell* 50: 823–829 (1987); Dunphy & Newport, *Cell* 55: 925–928 (1988); Lee & Nurse, *Trend Genet.* 4: 287–290 (1988).

Suppression or inhibition of Hh signaling is also an objective of therapeutic strategies. Since inactive fused has been shown to inhibit Hh signaling, it follows that a fused antagonist would also be expected to be antagonistic to Hh signaling. Limiting Hh signaling would be useful in disease states or disorders characterized by Hh signaling. For example, SHh is known to be active in Basal Cell Carcinoma; DHh is known to be active in spermatogenesis. Inhibitor or antagonist of Hh signaling would be effective therapeutics in the treatment of Basal Cell Carcinoma or male contraception, respectively.

The stimulation of Hh signaling is also an objective of therapeutic strategies. Activating Hh signaling would be useful in disease states or disorders characterized by inactive or insufficient Hh signaling. For example, degenerative disorders of the nervous system, e.g. Parkinson's disease, memory deficits, Alzheimer's disease, Lou Gehrig's disease, Huntington's disease, schizophrenia, stroke and drug addiction. Additionally, fused agonists could be used to great gut diseases, bone diseases, skin diseases, diseases of the testis (including infertility), ulcers, lung diseases, diseases of the pancreas, diabetes, osteoporosis.

F. Anti-vertebrate Fused Antibodies

The present invention further provides anti-vertebrate fused antibodies. Exemplary antibodies include polyclonal, monoclonal, humanized, bispecific, and heteroconjugate antibodies.

1. Polyclonal Antibodies

The anti-vertebrate fused antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the vertebrate fused polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-vertebrate fused antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the vertebrate fused polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the un fused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against vertebrate fused. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-vertebrate fused antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boemer et al. are also available for the preparation of human monoclonal antibodies (Cole et al., *Monoclonal Antibodies and Cancer Therapy*, Alan R. Liss, p. 77 (1985) and Boemer et al., *J. Immunol.*, 147(1):86–95 (1991)].

4. Bispecific Antibodies

Bispecific antibodies are monoclonal, preferably human or humanized, antibodies that have binding specificities for at least two different antigens. In the present case, one of the binding specificities is for the vertebrate used, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-tansfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for Anti-vertebrate Fused Antibodies

The anti-vertebrate fused antibodies of the invention have various utilities. For example, anti-vertebrate fused antibodies may be used in diagnostic assays for vertebrate fused, e.g. detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-vertebrate fused antibodies also are useful for the affinity purification of vertebrate fused from recombinant cell culture or natural sources. In this process, the antibodies against vertebrate fused are immobilized on a suitable support, such a Sephadex resin or filter paper, using methods well known in the art. The immobilized antibody then is contacted with a sample containing the vertebrate fused to be purified, and thereafter the support is washed with a suitable solvent that will remove substantially all the material in the sample except the vertebrate fused, which is bound to the immobilized antibody. Finally, the support is washed with another suitable solvent that will release the vertebrate fused from the antibody.

H. Fused Antagonists

Several approaches may be suitably employed to create the used antagonist and agonist compounds of the present invention. Any approach where the antagonist molecule can be targeted to the interior of the cell, which interferes or prevents wild type fused from normal operation is suitable. For example, competitive inhibitors, including mutant fused such as dominant negative mutant identified in the Examples, which prevent fused from properly binding with other proteins necessary for Hh signaling. Additional properties of such antagonist or agonist molecules are readily determinable by one of ordinary skill, such as size, charge and hydrophobicity suitable for transmembrane transport.

Where mimics or other mammalian homologues of fused are to be identified or evaluated, the cells are exposed to the test compound and compared to positive controls which are exposed only to human fused, and to negative controls which were not exposed to either the compound or the natural ligand. Where antagonists or agonists of fused signal modulation are to be identified or evaluated, the cells are exposed to the compound of the invention in the presence of the natural ligand and compared to controls which are not exposed to the test compound.

Detection assays may by employed as a primary screen to evaluate the phosphatase inhibition/enhancing activity of the antagonist/agonist compounds of the invention. The assays may also be used to assess the relative potency of a compound by testing a range of concentrations, in a range from 100 mM to 1 pM, for example, and computing the concentration at which the amount of phosphorylation or signal transduction is reduced or increased by 50% ($IC_{50}$) compared to controls.

Assays can be performed to identify compounds that affect phosphorylation of fused substrates. Specifically, assays can be performed to identify compounds that increase the phosphorylation activity of fused or assays can be performed to identify compounds that decrease the phosphorylation of fused substrates. These assays can be performed either on whole cells themselves or on cell extracts. The assays can be performed in a variety of formats, including protein-protein binding assays, biochemical screening assays, immunoassays, cell based assays, etc. Such assay formats are well known in the art.

The screening assays of the present invention are amenable to high-throughput screening of chemical libraries, and are particularly suitable for identifying small molecule drug candidates.

(1) Antagonist and Agonist Molecules

To screen for antagonists and/or agonists of fused signaling, the assay mixture is incubated under conditions whereby, but for the presence of the candidate pharmacological agent, fused induces hedgehog signaling with a reference activity. The mixture components can be added in any order that provides for the requisite hedgehog activity. Incubation may be performed at any temperature that facilitates optimal binding, typically between about 4° and 40° C., more commonly between about 15° and 40° C. Incubatio periods are likewise selected for optimal binding but also minimized to facilitate rapid, high-throughput screening, and are typically between about 0.1 and 10 hours, preferably less than 5 hours, more preferably less than 2 hours. After incubation, the effect of the candidate pharmacological agent on the fused signaling is determined in any convenient way. For cell-free binding-type assays, a separation step is often used to separate bound and unbound components. Separation may, for example, be effected by precipitation (e.g. TCA precipitation, immunoprecipitation, etc.), immobilization (e.g. on a solid substrate), followed by washing. The bound protein is conveniently detected by taking advantage of a detectable label attached to it, e.g. by measuring radioactive emission, optical or electron density, or by indirect detection using, e.g. antibody conjugates.

For example, a method of screening for suitable fused antagonists and/or agonists could involve the application of agents present in the fused activating Gli reporter assay described in the Examples. Such a screening assay could compare in sift hybridization in the presence and absence of the candidate antagonist and/or agonist in a fused expressing tissue as well as confirmation or absence of fused modulated cellular development. Typically these methods involve exposing an immobilized fused to a molecule suspected of binding thereto and determining binding or phosphorylation of the molecule to the immobilized fused and/or evaluating whether or not the molecule activates (or blocks activation of) fused. In order to identify such used binding ligands, fused can be expressed on the surface of a cell and used to screen libraries of synthetic candidate compounds or naturally-occurring compounds (e g., from endogenous sources such as serum or cells).

Suitable molecules that affect the protein-protein interaction of fused and its binding proteins include fragments of the latter or small molecules, e.g., peptidomimetics, which will prevent interaction and proper complex formation. Such small molecules, which are usually less than 10 K molecular weight, are preferable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Many pharmaceutical companies have extensive libraries of such molecules, which can be conveniently screened by using the assays of the present invention. Non-limiting examples include proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like.

A preferred technique for identifying molecules which bind to fused utilizes a chimeric substrate (e.g., epitope-tagged fused or fused immunoadhesin) attached to a solid phase, such as the well of an assay plate. The binding of the candidate molecules, which are optionally labeled (e.g., radiolabeled), to the immobilized receptor can be measured. Alternatively, competition for activation of Gli can be measured. In screening for antagonists and/or agonists, fused can be exposed to a fused substrate followed by the putative antagonist and/or agonist, or the fused binding protein and antagonist and/or agonist can be added simultaneously, and the ability of the antagonist and/or agonist to block fused activation can be evaluated.

(2) Detection Assays

The fused polypeptides are useful in assays for identifying lead compounds for therapeutically active agents that modulate fused hedgehog signaling. Specifically, lead compounds that either prevent the formation of fused signaling complexes or prevent or attenuate fused modulated hedgehog signaling (e.g, binding to fused itself or to a substrate) can be conveniently identified.

Various procedures known in the art may be used for identifying, evaluating or assaying the inhibition of activity of the fused proteins of the invention. As fused is believed to operate in a similar manner as other kinases, techniques known for use with identifying kinase/phosphatase modulators may also be employed with the present invention. In general, such assays involve exposing target cells in culture to the compounds and a) biochemically analyzing cell lysates to assess the level and/or identity of phosphorylation; or (b) scoring phenotypic or functional changes in treated cells as compared to control cells that were not exposed to the test substance. Such screening assays are described in U.S. Pat. No. 5,602171, U.S. Pat. No. 5,710,173, WO 96/35124 and WO 96/40276.

(a) Biochemical Detection Techniques

Biochemical analysis techniques can be evaluated by a variety of techniques. One typical assay mixture which can be used with the present invention contains fused and a protein with which fused is normally associated (e.g. Gli), usually in an isolated, partially pure or pure form. One or both of these components may be fused to another peptide or polypeptide, which may, for example, provide or enhance protein-protein binding, improve stability under assay conditions, etc. In addition, one of the components usually comprises or is coupled to a detectable label. The label may provide for direct detection by measuring radioactivity, luminescence, optical or electron density, etc., or indirect detection such as an epitope tag, an enzyme, etc. The assay mixture can additionally comprise a candidate pharmacological agent, and optionally a variety of other components, such as salts, buffers, carrier proteins, e.g. albumin, detergents, protease inhibitors, nuclease inhibitors, antimicrobial agents, etc., which facilitate binding, increase stability, reduce non-specific or background interactions, or otherwise improve the efficiency or sensitivity of the assay.

The following detection methods may also be used in a cell-free system wherein cell lysate containing the signal transducing substrate molecule and fused is mixed with a compound of the invention. The substrate is phosphorylated by initiating the kinase reaction by the addition of adenosine triphosphate (ATP). To assess the activity of the compound, the reaction mixture may be analyzed by the SDS-PAGE technique or it may be added to substrate-specific anchoring antibody bound to a solid support, and a detection procedure as described above is performed on the separated or captured substrate to assess the presence or absence of pSer/Thr. The results are compared to those obtained with reaction mixtures to which the compound is not added. The cell-free system does not required the natural ligand or knowledge of its identity. The cell-free system does not require mixtures to which the compound is not added. The cell-free system does not require the natural ligand or knowledge of its identity. For example, Posner et al. (U.S. Pat. No. 5,155,031 describes the use of insulin receptor as a substrate and rat adipocytes as target cells to demonstrate the ability of pervanadate to inhibit PTP activity. Another example, Burke et al., *Biochem. Biophys. Res. Comm.* 204: 129–134 (1994) describes the use of autophosphorylated insulin receptor and recombinant PTP1B in assessing the inhibitory activity of a phophotyrosyl mimetic.

(i) Whole Cell Detection

A common technique involves incubating cells with vertebrate fused and radiolabeled phosphate, lysing the cells, separating cellular protein components of the lysate using an SDS-polyacrylamide gel (SDS-PAGE) technique, in either one or two dimensions, and detecting the presence of phosphorylated proteins by exposing X-ray film. Detection can also be effected without using radioactive labeling. In such a technique, the protein components (e.g., separated by SDS-PAGE) are transferred to a nitrocellulose membrane where the presence of phosphorylated serine/threonines is detected using an antiphosphoserine/threonine antibody (anti-pS/T).

Alternatively, the anti-pS/T can be conjugated with an enzyme, such as horseradish peroxidase, and detected by subsequent addition of a colorimetric substrate for the enzyme. A further alternative involves detecting the anti-PS/T by reacting with a second antibody that recognizes the anti-PS/T, this second antibody being labeled with either a radioactive moiety or an enzyme as previously described. Examples of these and similar techniques are described in Hansen et al., *Electrophoresis* 14: 112–126 (1993); Campbell et al., *J. Biol. Chem.* 268: 7427–7434 (1993); Donato et al., *Cell Growth Diff.* 3: 258–268 (1992); Katagiri et al., *J. Immunol.* 150: 585–593 (1993). Additionally, the anti-pS/T can be detected by labeling it with a radioactive substance, followed by scanning the labeled nitrocellulose to detect radioactivity or exposure of X-ray film.

(ii) Kinase Assays

When the screening methods of the present invention for fused antagonists/agonists are carried out as an ex vivo assay, the target kinase (e.g. fused) can be a substantially purified polypeptide. The kinase substrate (e.g., MBP, Gli) is a substantially purified substrate, which in the assay is phosphorylated in a reaction with a substantially purified phosphate source that is catalyzed by the kinase. The extent of phosphorylation is determined by measuring the amount of substrate phosphorylated in the reaction. A variety of possible substrates may be used, including the kinase itself in which instance the phosphorylation reaction measured in the assay is autophosphorylation. Exogenous substrates may also be used, including standard protein substrates such as myelin basic protein (MBP); yeast protein substrates; synthetic peptide substrates, and polymer substrates. Of these, MBP and other standard protein substrates may be regarded as preferred (see Example 10). Other substrates may be identified, however, which are superior by way of affinity for the kinase, minimal perturbation of reaction kinetics, possession of single or homogenous reaction sites, ease of handling and post-reaction recover, potential for strong signal generation, and resistance or inertness to test compounds.

Measurement of the amount of substrate phosphorylated in the ex vivo assay of the invention may be carried out by means of immunoassay, radioassay or other well-known methods. In an immunoassay measurement, an antibody (such as a goat or mouse anti-phosphoserine/threonine antibody) may be used which is specific for phosphorylated moieties formed during the reaction. Using well-known ELISA techniques, the phosphoserine/threonine antibody complex would itself be detected by a further antibody linked to a label capable of developing a measurable signal (as for example a fluorescent or radioactive label). Additionally, ELISA-type assays in microtitre plates may be used to test purified substrates. Peraldi et al., *J. Biochem.* 285: 71–78 (1992); Schraag et al., *Anal. Biochem.* 211: 233–239 (1993); Cleavland, *Anal. Biochem.* 190: 249–253 (1990); Farley, *Anal. Biochem.* 203: 151–157 (1992) and Lozaro, *Anal. Biochem.* 192: 257–261 (1991).

For example, detection schemes can measure substrate depletion during the kinase reaction. Initially, the phosphate source may be radiolabeled with an isotope such as $^{32}$P or $^{33}$P, and the amount of substrate phosphorylation may be measured by determining the amount of radiolabel incorporated into the substrate during the reaction. Detection may be accomplished by: (a) commercially available scintillant-containing plates and beads using a beta-counter, after adsorption to a filter or a microtitre well surface, or (b) photometric means after binding to a scintillation proximity assay bead or scintillant plate. Weernink and Kijken, *J. Biochem. Biophs. Methods* 31: 49, 1996; Braunwalder et al., *Anal. Biochem.* 234: 23 (1996); Kentrup et al., *J. Biol. Chem.* 271: 3488 (1996) and Rusken et al., *Meth. Enzymol.* 200: 98 (1991).

Preferably, the substrate is attached to a solid support surface by means of non-specific or, preferably, specific binding. Such attachment permits separation of the phosphorylated substrate from unincorporated, labeled phosphate source (such as adenosine triphosphate prior to signal detection. In one embodiment, the substrate may be physically immobilized prior to reaction, as through the use of Nunc™ high protein binding plate (Hanke et al., *J. Biol. Chem.* 271: 695 (1996)) or Wallac ScintiStrip™ plates (Braunwalder et al., *Anal. Biochem.* 234: 23 (1996). Substrate may also be immobilized after reaction by capture on, for example, P81 phophocellulose (for basic peptides), PEI/acidic molybdate resin or DEAE, or TCA precipitation onto Whatman™ 3MM paper, Tiganis et al., *Arch. Biochem. Biophys.* 325: 289 (1996); Morawetz et al., *Mol. Gen. Genet.* 250; 17 (1996); Budde et al., *Int J. Pharmacognosy* 33: 27 (1995) and Casnellie, *Meth. Enz.* 200: 115 (1991). Yet another possibility is the attachment of the substrate to the support surface, as by conjugation with binding partners such as glutathione and streptavidin (in the case of GST and biotin), respectively) which have been attached to the support, or via antibodies specific for the tags which are likewise attached to the support.

Further detection methods may be developed which are preferred to those described above. Especially for use in connection with high-throughput screening, it is expected that such methods would exhibit good sensitivity and specificity, extended linear range, low background signal, minimal fluctuation, compatibility with other reagents, and compatibility with automated handling systems.

The in vivo efficacy of the treatment of the present invention can be studied against chemically induced tumors in various rodent models. Tumor cell lines propagated in in vitro cell cultures can be introduced in experimental rodents, e.g. mice by injection, for example by the subcutaneous route. Techniques for chemical inducement of tumors in experimental animals are well known in the art.

(b) Biological Detection Techniques:

The ability of the antagonist/agonist compounds of the invention to modulate the activity fused, which itself modulates hedgehog signaling, may also be measured by scoring for morphological or functional changes associated with ligand binding. Any qualitative or quantitative technique known in the art may be applied for observing and measuring cellular processes which comes under the control of fused. The activity of the compounds of the invention can also be assessed in animals using experimental models of disorders caused by or related to dysfunctional hedgehog signaling. For example, ineffective DHh hedgehog signaling in mice leads to viable but sterile mice. The effects of mutant fused (h fused-DN) also affects gut development, which is regulated by IHh expression. Additionally, proper SHh signaling is critical to murine embryonic development at the notochord and floor plate, neural tube, distal limb structures, spinal column and ribs. Improper SHh signaling, is also correlative with cyclopia. Any of these phenotypic properties could be evaluated and quantified in a screening assay for fused antagonists and/or agonist. Disease states associated with overexpression of hedgehog is associated with basal cell carcinoma while inactive sonic hedgehog signaling leads to improper neural development.

The data obtained from these cell culture assays and animal studies can be used in formulating a range of dosages for use in humans. The dosage of the compounds of the invention should lie within a range of circulating concentrations with little or no toxicity. The dosage may vary within this range depending on the dosage form employed and the route of administration.

(2) Antisense Nucleotides

Another preferred class of antagonists involves the use of gene therapy techniques, include the administration of antisense nucleotides. Applicable gene therapy techniques include single or multiple administrations of therapeutically effective DNA or mRNA. Antisense RNAs and DNAs can be used as therapeutic agents for blocking the expression of certain genes in vivo. Short antisense oligonucleotides can be imported into cells where they act as inhibitors, despite their low intracellular concentrations caused by restricted uptake by the cell membrane, Zamecnik et al., *Proc. Natl. Acad. Sci. USA* 83: 4143–4146 (1986). The oligonucleotides can be modified to enhance their uptake, e.g., by substituting their negatively charged phosphodiester groups by uncharged groups.

There are a variety of techniques known for introducing nucleic acids into viable cells. The techniques vary depending upon whether the nucleic acid is transferred into cultured cells in vitro, ex vivo, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection, Dzau et al., *Trends Biotech.* 11: 205–210 (1993). In some situations it is desirable to provide the nucleic acid source with an agent that targets the target cells, such as an antibody specific for a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262: 4429–4432 (1987); Wagner et al., *Proc. Natl. Acad. Sci. USA* 87: 3410–3414 (1990). For a review of known gene marking and gene therapy protocols, see Anderson et al., *Science* 256: 808–813 (1992).

In one embodiment, fused antagonist and/or agonist molecules may be used to bind endogenous ligand in the cell, thereby causing the cell to be unresponsive to fused wild type, especially when the levels of fused in the cell exceed normal physiological levels. Also, it may be beneficial to bind endogenous fused substrates or complexing agents that are activating undesired cellular responses (such as proliferation of tumor cells).

In a further embodiment of the invention, fused expression may be reduced by providing fused-expressing cells with an amount of fused antisense RNA or DNA effective to reduce expression of the fused protein.

I. Diagnostic Uses

Another use of the compounds of the invention (e.g., human and vertebrate fused, vertebrate fused variant and anti-vertebrate fused antibodies) described herein is to help diagnose whether a disorder is driven, to some extent, fused or hedgehog signaling. For example, basal cell carcinoma cells are associated with active hedgehog signaling.

A diagnostic assay to determine whether a particular disorder is driven by hedgehog signaling, can be carried out using the following steps: (1) culturing test cells or tissues; (2) administering a compound which can inhibit fused modulated hedgehog signaling; and (3) measuring the degree of kinase attenuation on the fused substrate in cell lysates or hedgehog mediated phenotypic effects in the test cells. The steps can be carried out using standard techniques in light of the present disclosure. For example, standard techniques can be used to isolate cells or tissues and culturing or in vivo.

Compounds of varying degree of selectivity are useful for diagnosing the role of fused. For example, compounds which inhibit fused in addition to another form of kinase can be used as an initial test compound to determine if one of several serine/threonine kinases drive the disorder. The selective compounds can then be used to further eliminate the possible role of the other serine/threonine kinases in driving the disorder. Test compounds should be more potent in inhibiting serine/threonine kinase activity than in exerting a cytotoxic effect (e.g., an $IC_{50}/LD_{50}$ of greater than one). The $IC_{50}$ and $LD_{50}$ can be measured by standard techniques, such as an MTT assay, or by measuring the amount of LDH released. The degree of $IC_{50}/LD_{50}$ of a compound should be taken into account in evaluating the diagnostic assay. Generally, the larger the ratio the more relative the information. Appropriate controls take into account the possible cytotoxic effect of a compound of a compound, such as treating cells not associated with a cell proliferative disorder (e.g., control cells) with a test compound, can also be used as part of the diagnostic assay. The diagnostic methods of the invention involve the screening for agents that modulate the effects of fused upon hedgehog signaling. Exemplary detection techniques include radioactive labeling and immunoprecipitating (U.S. Pat. No. 5,385,915).

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturers instructions unless otherwise indicated. The source of those cells identified in the following examples, and throughout the specification, by ATCC accession numbers is the American Type Culture Collection, Rockville, Md.

Example 1

Isolation of Human Fused cDNA Clones

An expressed sequence tag (EST) DNA database (LIFESEQ®, Incyte Pharmaceuticals, Palo Alto, Calif.) was searched for a human homologue of the Drosophilu segment polarity gene fused (SEQ ID NO: 26) (Preat et al., Nature 347: 87–9 (1990)). The EST Incyte #2515662 (FIG. 2) (SEQ ID NO. 3) was identified as a potential candidate. In order to identify human cDNA libraries containing human fused clones, human cDNA libraries in pRK5 were first screened by PCR using the following primers:

h-FUSED.f (SEQ ID NO.8)
5'-CAATACAATGGTGCTGACATCCATCAAAG GCA-3'
h-FUSED.r (SEQ ID NO.9)
5'-'GAAGGGAGGGGTGCCTACTGCCA-3'

A fetal lung library was selected and enriched for fused cDNA clones by extension of single stranded DNA from plasmid libraries grown in dug⁻/bung⁻ host using the h-FUSED.f primer (SEQ ID NO. 8) in a reaction containing 10 μl of 10×PCR Buffer (Perkin Elmer), 1 μl dNTP (20 mM), 1 μl library DNA (200 ng), 0.5 ml primer, 86.5

μl H$_2$O and 1 μl of Amplitaq® (Perkin Elmer) added after a hot start. The reaction was denatured for 1 min. at 95° C., annealed for 1 min. at 60° C. then extended for 20 min. at 72° C. DNA was extracted with phenol/CHCl$_3$, ethanol precipitated, then transformed by electroporation into DH10B host bacteria. Colonies from each transformation were plated and lifted on nylon membranes and screened with an oligo probe derived from the EST sequence of the following sequence:

h-FUSED.p (SEQ ID NO. 10):
5'-CTCCAGCTCTGGAGACATATAGAGTGGTGTG CCTTTGA-3'

The oligo probe was labeled with [γ-$^{32}$P]-ATP and T4 polynucleotide kinase. Filters were hybridized overnight at 42° C. in 50% formamide, 5×SSC, 10×Denhardt's, 0.05M sodium phosphate (pH 6.5), 0.1% sodium pyrophosphate, 50 μg/ml of sonicated salmon sperm DNA. The filters were then rinsed in 2×SSC and washed in 0.1×SSC, 0.1% SDS then exposed to Kodak®X Ray films. Two positive clones (DNA28494, SEQ ID NO. 6) and DNA28495 (SEQ ID NO. 4)—FIGS. 5 & 4, respectively) containing an insert of approximately 5 kb were isolated and sequenced. The sequence of clone DNA28495 (SEQ ID NO. 4) contains a potential initiation methionine at position 116 followed by an open reading frame of 1944 bp (FIG. 4). However, this open reading frame (ORF) encodes a protein that is only 648 amino acids long, somewhat shorter than the 795 amino acid sequence of the Drosphila Jused. Interestingly, a second open reading frame is present in the 3' region of the cDNA, from nucleotide 2295 to 4349 (FIG. 4), which suggests that the cDNA may have been improperly spliced and that an intron remains between the 2 ORFs, or correspond to an alternatively spliced variant of fused. The sequence of clone DNA28494 (SEQ ID NO. 6) is very similar. There is one nucleotide difference between clone DNA28495 (SEQ ID NO. 4) and clone DNA28494 (SEQ ID NO. 6) located in the first ORF at position 1863 of clone 28495 (SEQ ID NO. 4) (A vs. G) which changes the encoded sequence at amino acid position 583 from Gln to Arg, respectively. (Compare FIGS. 4–5). This change is likely due to an allelic variation. The first open reading frame of DNA28494 (SEQ ID NO. 6) starts at residue 115 and is followed by a 647 amino acid long open reading frame. The sequences are identical except for the one change described above at position 583 and for the last 9 residues in the first open reading frame.

Example 2

Expression of Fused Clones

In order to determine the size of the protein expressed from the cDNA corresponding to DNA28495 (SEQ ID NO.

4) and DNA28494 (SEQ ID NO. 6), an HA epitope tag was inserted at the N-terminus of the protein by PCR using the following primers:

Hfus.Cla-HA.F: (SEQ ID NO. 11)
5'-CCATCGATGTACCCATACCACGTCCCAGACTA CGCTGAAAAGTACCACGTGTTGGAGATG-3'
and hFus.Xba.R: (SEQ ID NO. 12)
5'-GCTCTAGACTAAGGGCGCAGGTCCTGTGTTC TG-3'.

The PCR product was purified, digested with ClaI-SmaI and subcloned into the pRK5 plasmids containing DNA28494 (SEQ ID NO. 6) and DNA28495 (SEQ ID NO. 4). DNA from each of the constructs was transfected overnight into 293 cells using the $CaPO_4$ method (Sambrook et al., supra; Ausuble et al., supra). After about 24 h to 48 h. after transfection, the cells were harvested and the cell pellet was lysed in I ml of lysine buffer (50 mM Tris pH 8.0, 150 mM NaCl, 1 mM EDTA, 1% NP40, Aprotinin, Leupeptin, -PMSF, 1 mM NaF and 1 mM Sodium Vanadate) for 20 min at 4° C. The extract was spun for 10 min at 10K then the supernatant was transferred to a new tube and precleared with 20 μl Protein A sepharose for 1 h. The protein A sepharose was spun down and 1 μl of anti-HA antibody (5 μg, Boehringer) was added to each tube. After overnight incubation at 4° C., 30 μl of Protein G sepharose was added and the tubes incubated at 4° C. for 1 hour. The protein G beads were then spun down for 1 min., washed 3 times with lysis buffer, resuspended in 20 μl of laemli buffer in the presence of β-mercapto-ethanol. Samples were denatured for 5 min. at 100° C. then loaded on a 6% polyacrylamide gel. Proteins were then transferred to nitrocellulose and analyzed by Western blot using the same anti-HA antibody overnight at 1 μg/ml in blocking buffer (PBS, 0.5% Tween®, 5% non fat dry milk, 3% goat serum followed by an anti-mouse HRP. ECL was used for the detection and the membrane was exposed for 90 seconds to X-Ray films. A specific band of 150 kDa was detected in the cell pellet of cells transfected with the construct with construct corresponding to clone DNA28494 (SEQ ID NO. 6) and a specific band of approximately 100 kDa could be detected for clone DNA28495 (SEQ ID NO. 4) (FIG. 6). These bands were not present in the mock transfected control. The presence of the 150 kDa band suggests the two open reading frames of DNA28494 (SEQ ID NO. 6) can be spliced together to direct the synthesis of a large protein of 150 kDa. The absence of this band for DNA28495 (SEQ ID NO. 4) suggested that this clone apparently cannot be correctly spliced. Alternative splicing of the used gene seems to lead to the production of several different products and may be a mechanism or regulation of fused activity. Specific regions at the C-terminus of the Drosophila fused protein is known to be required for the activity of the molecule, Therond et al., *Genetics* 142: 1181–1198 (1996); Robbins et al., *Cell* 90: 225–234 (1997). Shorter fused molecules truncated at the C-terminus may therefore correspond to inactive or to dominant negative forms of the molecule.

Example 3

Northern Blots

In order to determine the best tissue source to isolate more fused cDNAs and to identify a transcript encoding a full length 150 kDa fused molecule, human multiple tissue northern blots I, II and fetal blot from Clontech were probed with a 1.6 kb, ClaI-AccI fragment derived from clone DNA28494 (SEQ ID NO. 6) labeled by random priming. The blots were hybridized in 50% formamide, 5×SSC, 10×Denhardt's, 0.05M Sodium phosphate (pH 6.5), 0.1% Sodium pyrophosphate, 50 mg/ml sonicated salmon sperm DNA, all in the presence of $1\times10^6$ cpm/ml $^{32}$P-labeled probe at 42° C. overnight. The blots were washed in 2×SSC at RT for 10 minutes and washed in 0.2×SSC/0.1% SDS at 42° C. for 30 minutes then exposed to x-ray film overnight. FIG. 7 shows that the fused message is expressed at high levels in testis and at low levels in most other tissues, including fetal tissues. (FIG. 7).

Example 4

PCR on Different Tissues to Identify the Correct Splice Form

In order to isolate a cDNA where the 2 potential ORFs were spliced together correctly, we designed the following primers flanking the potential intron and amplified various tissues including human fetal brain, brain, keratinocyte, testis, ovary, fetal liver, and lung templates.

F1 (SEQ ID NO. 13)
5'-CTGACGACACAGCAGGTTGTC-3'
R4 (SEQ ID NO. 14)
5'-CAGATGCTTCAGGATGGACAT-3'

Two microliters of each cDNA library was used as the template and PCR was done with Klentaq® polymerase. PCR was performed for 45 cycles of amplification with 94° C. denaturation for 1 min., 55° C. annealing for 1 min., and 68° C. extensions for 2 min. One fifth of the reaction was loaded on 1% agarose gel and was Southern blotted. The blot was hybridized overnight with full-length fused probe labeled by random priming as described for the Northern blot.

A 1 kb PCR fragment was identified in fetal brain, testis and ovary. This fragment was gel-purified and subjected to direct PCR sequencing using both the F1 and R4 primers (SEQ ID NOS. 13 and 14) identified above as well a the following primers:

hf16 (SEQ ID NO. 15)
5'-AGAGTAGCAACGTCACTGC-3'
hf8 (SEQ ID NO. 16)
5'-CCTCACTGACAAGGCAGCAGG-3'
hf19 (SEQ ID NO. 17)
5'-CCCGAGGAGGCATCTGCACAG-3'

The sequence of this 1 kb fragment revealed that intron sequences were absent and that the 2 ORFs were connected together in the same reading frame. The sequence of the correctly spliced sequence is shown in FIG. 1 (SEQ ID NO. 1). The initiator ATG is present at position 161 and is followed by an ORF of 3945 nucleotides which encodes a 1315 amino acid long protein with a predicted molecular weight of 144 kDa.

The overall similarity with Drosophila fused (SEQ ID NO. 23) is 28% (FIG. 2). The N-terminal 263 amino acid domain of the protein containing the kinase domain is 55% homologous to the Drosophila fused kinase domain. The remaining 1052 amino acids portion of the protein is not appreciably homologous to other known proteins and, interestingly, is not homologous to the corresponding region in Drosophila fused. Interestingly, this region of non-homology includes the very C-terminus of the fly protein which appears to be required for activity, Robbins et al., *Cell* 90: 225–34 (1997); Therond et al., *Genetics* 142: 1181–98 (1996). The improperly spliced cDNAs described above may reflect alternative splicing of the fused gene which leads to the production of a molecule with a truncated C-terminus and may be a mechanism to regulate fused activity.

Example 5

Reconstitution of the Correctly Spliced Full Length Human Fused

The fused clone DNA28495 (SEQ ID NO. 4) was subcloned from the pRK5B plasmid into pRK5.tkneo using ClaI-HindIII. PCR was performed using human testis cDNA as a template and the primers h*B* (SEQ ID NO. 18) (CAGAACTTCAGGTCCTAAAGG) and R4 (sequence see above, Example 4). PCR conditions were 45 cycles of (94° C., 1 min, 46° C. to 68° C. temperature gradient annealing and 68° C., 4 min). The PCR fragment was digested with AccI and ligated in the pRK5.tkneo. fused plasmid cut with AccI in order to replace the region containing the intron with the correct spliced form. Two subclones were sequenced between the two AccI site and had the same correct sequence.

Example 6

In situ Hybridization

E11.3 and E 13.5 mouse embryos were immersion-fixed overnight at 4° C. in 4% paraformaldehyde, cryoprotected overnight in 15% sucrose, embedded in O.T.C. and frozen on liquid nitrogen. Adult mouse brains were fresh frozen with powdered dry ice. P1 mouse brains, adult mouse testis and adult rat spinal cords were embedded in O.T.C. and frozen on liquid nitrogen. Sections were cut at 16 mm, and processed for in situ hybridization for fused by the method of Phillips et al., *Science* 250: 290–294 (1990). RNA probes were labeled with $^{33}$P-UTP as described by Melton et al., *Nucleic Acids Res.* 12: 7035–7052 (1984). Sense and antisense probes were synthesized from a mouse fused DNA fragment using T3 and T7, respectively, corresponding to the region encoding amino acid residues 317–486 of the human sequence.

FIG. 8 reveals that the mouse fused mRNA is widely distributed in SHh responsive tissues, including the neural tube, pre-somitic mesoderm, somites, developing limb buds and skin. Transcripts for fused were also found in the embryonic gut, testis, cartilage and muscle—Tissues that are exposed to the other members of the Hh protein family: Desert and Indian. In the E11-5 mouse nervous system, high levels of fused transcripts were detected throughout the forebrain, midbrain, hindbrain and spinal cord. These high levels of expression were retained in embryonic day 13.5. In both embryonic days 11.5 and 13.5, fused mRNA was detected mainly in the ventral aspect of the neural tube, in regions that are likely to be exposed to the ventral midline-derived SH/h. By post natal day—1, widespread expression of fused is still maintained throughout the brain with high levels of transcripts detected in the cortex, hypocampus, ependima and choroid plexus. In the adult, low levels of fused expression are detected all through the brain with higher levels confined to the ependyma.

The tissue distribution of fused and the Hh receptor components, Smo and Ptch show considerable overlap. All of them are initially expressed through the neural tube as well as in other Hh responsive tissues. However, whereas Smo mRNA was evenly distributed along the dorso-ventral axis, Ptch and fused mRNAs are found at higher levels ventrally, suggesting that they may be upregulated by Hh. In addition while by day E12, expression of both Smo and Ptch is found mainly in cells which are in close proximity to the ventricular zone, fused mRNA is still widely expressed and its levels decline only later. In the adult expression of both Smo and fused is confined to the ependima where neurogenesis continues.

Detailed analysis of fused expression in adult testis was also performed by in situ hybridization (FIG. 9). fused was found to be expressed at very high levels on stages I and II germ cells in the seminiferous tubules. Levels of fused vary in different seminiferous tubules, suggesting that its expression is regulated according to the germinal cell state of differentiation.

Example 7

Gli Luciferase Assay

Given the low homology between d fused and h fused, it was prudent to determine whether in fact the isolated h fused is indeed a mediator of Hh signaling. The following assay was developed to measure the activation of the transcription factor GLI, the mammalian homologue of the Drosophila cubitus interruptus (Ci). It has been shown that GLI is a transcription factor activated upon SHh stimulation of cells.

Nine (9) copies of a GLI binding site present in the HNF3β enhancer, (Sasaki et al., *Development* 124: 1313–1322 (1997)), were introduced in front of a thymidine kinase minimal promoter driving the luciferase reporter gene in the pGL3 plasmid (Promega). The sequence of the GLI binding sequence was: TCGACAAGCAGGGAACAC-CCAAGTAGAAGCTC (p9XGliLuc) (SEQ ID NO. 19), while the negative control sequence was: TCGACAAG-CAGGGAAGTGGGAAGTAGAAGCTC (p9XmGliLuc) (SEQ ID NO. 20). These constructs were cotransfected with the full length fused construct or with a plasmid encoding sonic hedgehog in C3H10T1/2 cells grown in F12, DMEM (50:50), 10% FCS heat inactivated. The day before transfection 1×105 cells per well was inoculated in 6 well plates, in 2 ml of media. The following day, 1 µg of each construct was cotransfected in duplicate with 0.025 mg ptkRenilla luciferase plasmid using lipofectamine (Gibco-BRL) in 100 µl OptiMem (with GlutaMAX) as per manufacturer's instructions for 3 hours at 37° C. Serum (20%, 1 ml) was then added to each well and the cells were incubated for 3 more hours at 37° C. Cells were then washed twice with PBS, then incubated for 48 hours at 37° C. in 2 ml of media. Each well was then washed with PBS, and the cells lysed in 0.5 ml Passive Lysis Buffer (Promega) for 15 min. at room temperature on a shaker. The lysate was transferred in eppendorf tubes on ice, spun in a refrigerated centrifuge for 30 seconds and the supernatant saved on ice. For each measure, 20 µl of cell lysate was added to 100 µl of LARII (luciferase assay reagent, Promega) in a polypropylene tube and the luciferase light activity measured. The reaction was stopped by the addition of Stop and Glow buffer (Promega), mixed by pipetting up and down 3 to 5 times and Renilla luciferase lights activity was measured on the luminometer.

As shown in FIG. 6, fused can induce GLI activity (9.5 fold) in a similar manner as SHh (5.5 fold) This result suggests that the fused gene isolated is a mediator of SHh signaling. An irrelevant serine-threonine kinase, Akt, was not active in this assay (data not shown). The fused activity is dependent on an intact kinase domain as molecules with deletion of this region (fused C-term) (SEQ ID NO. 27) or mutation of a conserved lysine residue at about amino acid position 33 in the ATP binding site (fused-DN (SEQ ID NO. 25)) were not able to activate GLI. Similarly, the C-terminal tail of the protein is necessary for this activity since the kinase domain alone was not active in this assay (fused KD) (SEQ ID NO. 24). Expression of each protein was verified by Western blot using an HA tag inserted at the N-terminus of the molecule (data not shown). These results substantiate the conclusion that the homologue of the d fused isolated by Applicants is indeed hFused. Furthermore, these results indicate that fused is capable of and sufficient for the activation of Gli, the major target of SHh signaling and is thus likely to be a direct mediator of the SHh signal in vertebrates.

Example 8

Induced Cyclopia in Frog Embryos

Introduction:

In order to demonstrate that the human fused gene is not only capable of but also required to transduce the SHh signal in vertebrates, a mutant version of fused known as fused-DN (dominant negative) having a mutation of the lysine at position 33 in the ATP binding site was created (SEQ ID NO. 25). This residue is conserved among all kinases and is necessary for kinase activity (Hanks et al., Methods Enzymol. 200: 38–62 (1991) and its conversion to any other residue in most cases results in the creation of dominant negative mutants.

Methods:

Plasmid Construction:

Wild type fused cDNA (SEQ ID NO. 1) with an HA tag inserted at the carboxy terminus was subcloned into pRK5 and a dominant negative form was generated by conversion of lysine at positive 33 to an arginine. Supercoiled plasmid DNA was prepared by Qiagen and used for injection into Xenopus laevis embryo.

Manipulation of Xenopus embryos:

Adult female frogs were boosted with 200 I.U. pregnant mare serum 3 days before use and with 800 I.U. of human chorionic gonadotropin the night before injection. Fresh oocytes were squeezed out from female frogs the next morning and in vitro fertilization of oocytes was performed by mixing oocytes with minced testis from sacrificed male frogs. Developing embryos were maintained and staged according to Nieuwkoop and Faber, Normal Table of Xenopus laevis, N.-H. P. Co., ed. (Amsterdam, 1967).

Fertilized eggs were dejellied with 2% cysteine (pH 7.8) for 10 minutes, washed once with distilled water and transferred to 0.1×MBS with 5% Ficoll. Fertilized eggs were lined on injection trays in 0.1×MBS with 5% Ficoll. Two-cell stage developing Xenopus embryos were injected with 200 pg of either pRK5 containing wild type fused (WT (SEQ ID NO. 1)) or dominant negative fused (DN (SEQ ID NO. 25)). Injected embryos were kept on trays for another 6 hours, after which they were transferred to 0.1×MBS with 50 mg/ml gentamycin for 3 days until reaching Nieukwkoop stage 35 when eye development is complete.

Results:

To test whether human fused gene acts as a signal transducer of Hedgehog signaling, we injected wild type or dominant negative form of human fused in developing frog embryos. Embryos injected with 120 pg of DNA divided normally in blastula stage and gastrulate normally. While eye development was normal in wild type, fused (SEQ ID NO. 2) injected and mock injected embryos, about 30% (Table 1) of the embryos that were injected with fused-DN showed fused eye structure or two eyes connected by some pigmented retina tissue (FIG. 11A). In Table 1,200 pg of plasmid DNA was delivered to the animal pole of 2-cell stage embryos. Each sample represents the results of at least 3 independent experiments. Embryos were scored visually for cyclopia defects.

TABLE 1

Fusion-DN Induced Cyclopia in Xenopus Embryos

| Injected DNA | Normal | Cyclop | n |
|---|---|---|---|
| Hu-fused (SEQ ID NO. 2) | 45 | 0 | 45 |
| kinase domain (SEQ ID NO. 24) | 43 | 0 | 43 |
| C-terminus (SEQ ID NO. 27) | 53 | 1 | 54 |
| fused DN (SEQ ID NO. 25) | 32 | 15 | 47 |
| uninjected | 61 | 0 | 61 |

The observed cyclopia phenotype is strikingly similar to the one of mouse embryos deficient in SHh (Chiang et al., Nature 383: 407–13 (1996) and of zebrafish embryos where SHh signaling has been blocked by overexpression of a constitutive active PKA, Hammerschmidt et al., Genes Dev. 10: 647–58 (1996); Ungar and Moon, Dev. Biol. 178: 186–91 (1996). In addition, both brain (forebrain) and gut development appeared normal at later stages of tadpole development in the fused-DN (SEQ ID NO. 25) injected embryos (FIG. 11B). In contrast, embryos overexpressing either wild type fused (SEQ ID NO. 2) or N or C-terminal terminal truncation mutants (SEQ ID NOS. 27 & 24, respectively) did not present any abnormalities.

During normal development of the Xenopus eye, the eye primordium starts as a single field expressing transcription factor Pax-6, which is a vertebrate homologue of Drosophila eyeless, Li et al., Development, 124: 603–15 (1997). At the neurula stage, this eye field is separated into two eye primordia due to an inhibiting signal from prechordal mesoderm. It has been further demonstrated that SHh is the prechordal mesoderm derived signal that is responsible for the inhibition of Pax-6 expression in the midline of the eyefield.

To further understand how overexpression of fused-DN (SEQ ID NO: 25) induced a fused eye in Xenopus embryos, whole mount in situ hybridization was performed in order to determine the expression pattern of Pax-6 in injected embryos. As shown in FIG. 11C, Pax-6 expression in embryos injected with fused-DN (SEQ ID NO: 25) remains as a single field (FIG. 11D). Thus fused-DN (SEQ ID NO: 25) induces a cyclopia phenotype by most likely preventing SHh from inhibiting Pax-6 expression in the midline of the eyefield.

Example 9

Rescue of Fused-DN (SEQ ID NO. 25) Injected Xenopus Embryos by Gli

SHh expression in early floor plate cells is induced by SHh produced by the notochord. To test whether SHh expression in the floor plate will also be inhibited when SHh signaling is blocked, early neurula stage embryos injected with fused-DN or wild-type constructs were stained for SHh expression (See Example 8 for procedure). SHh expression in floor plate cells or early neurula stage embryos was completely suppressed in 26 out of 28 embryos injected when the mutated fused is overexpressed (Table 2, FIG. 11C, left embryo), while the expression of SHh was unaffected in control embryos (FIG. 6E, right embryo). Table 2 represents scored data from three independent experiments. 100 pg of fused-DN, 100 pg of fused-wt or 50 pg of Gli-1 plasmid were injected in 2-cell stage embryos. Embryos were harvested at early neurula stage for SHh staining.

TABLE 2

Wild type fused and Gli rescue SHh expression in
floor plate when coexpressed with fused-DN

|  | SHh staining | percentage |
| --- | --- | --- |
| fused-DN | 2/28 | 7% |
| fused-DN + fused WT | 20/24 | 83% |
| fused-DN + Gli | 36/36 | 100 |

To confirm that this phenotype was due to specific inhibition of the SHh signaling pathway in the floor plate, we attempted to rescue the phenotype by coinjection of wt fused RNA with fused-DN RNA in a 1:1 ratio. Table 2 shows that more than 80% of the embryos coinjected with wt fused and fused-DN RNAs show normal SHh staining in the floor plate. This demonstrates that SHh expression in fused-DN injected embryos is specifically blocked by inhibition of endogenous fused activity.

To further demonstrate that the observed phenotype of fused-DN are due to disruption of the SHh signal cascade and to confirm that h fused works upstream of Gli in this pathway, we asked whether the overexpression of Gli can also rescue the phenotype of Xenopus embryos injected with fused-DN. As shown in Table 2, the rescue of SHh expression in the floor plate of fused-DN injected embryos is complete when Gli is overexpressed. Taken together, these findings are consistent with Applicants hypothesis that vertebrate fused functions in the SHh pathway and that is a necessary mediator in the SHh signal transduction pathway, which acts upstream of Gli.

Example 10

Immunoprecipitations and In Vitro Kinase Assay

To directly determine whether h fused has kinase activity, fused (SEQ ID NO. 2), fused-DN (SEQ ID NO. 25) and fused-kd (SEQ ID NO. 24) cDNAs were tagged with the influenza HA epitope tag and transiently transfected into 293 cells. Immunoprecipitates were tested for kinase activity in the presence of myelin basic protein (MBP) and [$\gamma$-$^{32}$P]-ATP. The amount of 32P incorporated into MBP was determined after SDS-PAGE and found to be was about 3 times higher than in fused-KD (SEQ ID NO. 24) and 2 times higher in wt fused (SEQ ID NO. 2) containing extracts compared to controls, while mutation of Lys33 to Arg (fused-DN (SEQ ID NO. 25)) neutralizes the activity (FIG. 12).

For immunoprecipitation experiments human embryonic kidney 293 cells were transiently transfected with the various expression plasmids. After 24 hours, the transfected cells were collected and lysed for 20 min. at 4° C. in 1 ml of lysis buffer (50 mM Tris, pH 8.0), 150 mM NaCl, 1 mM EDTA, sodium fluoride, 1 mM sodium orthovanadate, 1 mM PMSF and protease inhibitors (Complete, Boehringer Mannheim) containing 1% NP-40, 0.5% deoxycholic acid. Cell debris was removed by centrifugation for 10 min. at 10,000 rpm and the sodium chloride concentration of the cell lysates was increased to 250 mM. The supernatant was precleared for 1 hour with 20 $\mu$l Protein A Sepharose (Pharmacia). Lysates were immunoprecipitated using anti-HA antibodies followed by Protein A Sepharose. The beads were washed twice with lysis buffer containing 250 mM sodium chloride, twice with lysis buffer containing 1 M sodium chloride, and then twice with kinase assay buffer (20 mM HEPES, pH 7.6), 1 mM DTT, 1 mM NaF and 1 mM sodium orthovanadate). After the last wash, the beads were resuspended in 20 $\mu$l kinase assay buffer supplemented with 10 mCi [$\gamma$-$^{32}$P]-ATP, 20 mM $\beta$-glycerophosphate, 20 mM PNPP, 20 mM MgCl$_2$, EGTA, 100 $\mu$M cold ATP and 0.5 mg/ml Myelin Basic Protein (Sigma), and incubated for 20 min. at 37° C. Reactions were stopped with 20 $\mu$l SDS-sample buffer, run on a denaturing 4–20% SDS polyacrylamide gel, and analyzed by phosphoimager.

Example 11

Expression of Fused in E. coli

The DNA sequence encoding human fused is initially amplified using selected PCR primers. The primers should contain restriction enzyme sites that correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences that encode for an antibiotic resistance gene, a trp promoter, a polyhis leader (including the first six STII codons, polyhis sequence, and enterokinase cleavage site), the vertebrate fused coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confumed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized vertebrate fused protein can then be purified using a metal chelating column under conditions that allow tight binding of the protein.

Example 12

Expression of Fused in Mammalian Cells

The vector, pRK5 (see EP 307,247, published Mar. 15, 1989), is employed as the expression vector. Optionally, the vertebrate fused DNA is ligated into pRK5 with selected restriction enzymes to allow insertion of the vertebrate fused DNA using ligation methods such as described in Sambrook et al., supra. The resulting vector is called pRK5-fused.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 $\mu$g pRK5-fused DNA is mixed with about 1 $\mu$g DNA encoding the VA RNA gene [Thimmappaya et al., Cell, 31:543 (1982)] and dissolved in 500 $\mu$l of 1 mM Tris-HCl, 0.1 mM EDTA, 0.227 M CaCl$_2$. To this mixture is added, dropwise, 500 $\mu$l of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 $\mu$Ci/ml 35S-cysteine and 200 $\mu$Ci/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of vertebrate fused polypeptide. The cultures containing transfected cells may undergo further incubation (in serum free medium) and the medium is tested in selected bioassays.

In an alternative technique, vertebrate fused may be introduced into 293 cells transiently using the dextran sulfate method described by Somparyrac et al., Proc. Natl. Acad. Sci., 12:7575 (1981). 293 cells are grown to maximal density in a spinner flask and 700 $\mu$g pRK5-fused DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 $\mu$g/ml bovine insulin and 0.1 $\mu$g/ml bovine transferrin. After about four days, the conditioned media is centrifuged and filtered to remove cells and debris. The sample containing expressed vertebrate fused can then be concentrated and purified by any selected method, such as dialysis and/or column chromatography.

In another embodiment, vertebrate fused can be expressed in CHO cells. The pSUi-fused can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of vertebrate fused polypeptide, the culture medium may be replaced with serum free medium. Preferably, the cultures are incubated for about 6 days, and then the conditioned medium is harvested. The medium containing the expressed vertebrate fused can then be concentrated and purified by any selected method.

Epitope-tagged vertebrate fused may also be expressed in host CHO cells. The vertebrate fused may be subcloned out of the pRK5 vector. The subclone insert can undergo PCR to fuse in frame with a selected epitope tag such as a poly-his tag into an expression vector. The poly-his tagged vertebrate fused insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged vertebrate fused can then be concentrated and purified by any selected method, such as by Ni$^{2+}$-chelate affinity chromatography.

Example 13

Expression of Vertebrate Fused in Yeast

The following method describes recombinant expression of vertebrate fused in yeast.

First, yeast expression vectors are constructed for intracellular production or secretion of vertebrate fused from the ADH2/GAPDH promoter. DNA encoding vertebrate fused, a selected signal peptide and the promoter is inserted into suitable restriction enzyme sites in the selected plasmid to direct intracellular expression of vertebrate fused. For secretion, DNA encoding vertebrate fused can be cloned into the selected plasmid, together with DNA encoding the ADH2/GAPDH promoter, the yeast alpha-factor secretory signal/leader sequence, and linker sequences (if needed) for expression of vertebrate fused.

Yeast cells, such as yeast strain AB 110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant vertebrate fused can subsequently be isolated and purified by removing the yeast cells from the fermentation medium by centrifugation and then concentrating the medium using selected cartridge filters. The concentrate containing vertebrate fused may further be purified using selected column chromatography resins.

Example 14

Expression of Vertebrate Fused in Baculovirus-Infected Insect Cells

The following method describes recombinant expression of vertebrate fused in Baculovirus-infected insect cells.

The vertebrate fused is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the vertebrate fused or the desired portion of the vertebrate fused (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold® virus DNA (Pharmingen) into *Spodoptera frugiperda* ("Sf9") cells (ATCC CRL 1711) using lipofectin (commercially available from GIBCO-BRL). After 4- 5 days of incubation at 28° C., the released viruses are harvested and used for further amplifications. Viral infection and protein expression is performed as described by O'Reilley et al., *Baculovirus expression vectors: A Laboratory Manual*, Oxford: Oxford University Press (1994).

Expressed poly-his tagged vertebrate fused can then be purified, for example, by Ni$^{2+}$-chelate affinity chromatography as follows. Extracts are prepared from recombinant virus-infected Sf9 cells as described by Rupert et al., *Nature*, 362:175–179 (1993). Briefly, Sf9 cells are washed, resuspended in sonication buffer (25 mL Hepes, pH 7.9; 12.5 mM MgCl$_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 $\mu$m filter. A Ni$^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged vertebrate fused are pooled and dialyzed against loading buffer. Alternatively, purification of the IgG tagged (or Fc tagged) vertebrate fused can be performed using known chromatography techniques, including for instance, Protein A or protein G column chromatography Example 15

Preparation of Antibodies that Bind Vertebrate Fused

This example illustrates preparation of monoclonal antibodies, which can specifically bind vertebrate fused.

Techniques for producing the monoclonal antibodies are known in the art and are described, for instance, in Goding, supra. Immunogens that may be employed include purified vertebrate fused, fusion proteins containing vertebrate fused, and cells expressing recombinant vertebrate fused on the cell surface. Selection of the immunogen can be made by the skilled artisan without undue experimentation.

Mice, such as Balb/c, are immunized with the vertebrate fused immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect vertebrate fused antibodies.

After a suitable antibody titer has been detected, the animals "positive" for antibodies can be injected with a final intravenous injection of vertebrate fused. Three to four days later, the mice are sacrificed and the spleen cells are harvested. The spleen cells are then fused (using 35% polyethylene glycol) to a selected murine myeloma cell line such as P3x63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against vertebrate fused. Determination of "positive" hybridoma cells secreting the desired monoclonal antibodies against vertebrate fused is within the skill in the art.

The positive hybridoma cells can be injected intraperitoneally into syngeneic Balb/c mice to produce ascites containing the anti- vertebrate fused monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Deposit of Material

The following materials have been deposited with the American Type Culture Collection, 12301 Parklawn Drive, Rockville, Md., USA (ATCC):

| Designation: | ATCC Dep. No. | Deposit Date |
|---|---|---|
| pRK5tkneo.hFused-1272 | 209637 | 2/19/98 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. Isolated fused polypeptide comprising amino acid residues selected from the group consisting of:
   (a) SEQ ID NO:24;
   (b) SEQ ID NO:24 with one to five conservatively substituted amino acid residues;
   (c) SEQ ID NO:24 with an addition or deletion of one to five amino acid residues;
   (d) an amino acid sequence encoded by a nucleic acid sequence which hybridizes under stringent conditions to the complement of nucleotides 161–940 of the nucleotide sequence SEQ ID NO:1 and which modulates hedgehog signaling;
   (e) SEQ ID NO:2;
   (f) SEQ ID NO:2 with one to five conservatively substituted amino acid residues;
   (g) SEQ ID NO:2 with an addition or deletion of one to five amino acid residues; and
   (h) an amino acid sequence encoded by a nucleic acid sequence which hybridizes under stringent conditions to the complement of nucleotides 161–1315 of the nucleotide sequence SEQ ID NO:1 and which modulates hedgehog signaling;
   and wherein said stringent conditions are defined by:
      (i) 0.015M sodium chloride, 0.0015M sodium citrate, 0.1% sodium dodecyl sulfate at 50° C.; or
      (ii) 50% vol./vol. formamide with 0.1% bovine serum albumin, 0.1% Ficoll, 0.1% polyvinylpyrrolidone, 50 mM sodium phosphate buffer at pH 6.5 with 750 mM sodium chloride, 75 mM sodium citrate at 42° C.; or
      (iii) 50% formamide, 5×SSC (0.75 M NaCl, 0.075M sodium citrate), 50 mM sodium phosphate (pH 6.8), 0.1% sodium pyrophosphate, 5×Denhardt's solution, sonicated salmon sperm DNA (50 µg/ml), 0.1% SDS, 10% dextran sulfate at 42° C., wherein (i), (ii) or (iii) is followed with washes at 42° C. in 0.2×SSC and 50% formamide at 55° C., followed by a wash of 0.1×SSC containing EDTA at 55° C.

2. A chimeric molecule comprising the fused polypeptide of claim 1 fused to a heterologous amino acid sequence.

3. The chimeric molecule of claim 2 wherein said heterologous amino acid sequence is an epitope tag sequence.

4. The chimera of claim 3 wherein the epitope tag is selected from the group consisting of: polyhistidine; polyhistidine-glycine; flu HA; c-myc; Herpes Simplex virus glycoprotein D; FLAG; KT3; α- tubulin; T7 gene 10 protein peptide tag and influenza HA.

5. The chimeric molecule of claim 2 wherein said heterologous amino acid sequence is a constant region of an immunoglobulin.

6. The chimera of claim 5 wherein the immunoglobulin constant region is selected from the group consisting of: IgG-1, IgG-2, IgG-3, IgG-4, IgA-1, IgA-2, IgE, IgD, and IgM.

7. The polypeptide of claim 1 comprising an amino acid sequence having a lysine at amino acid position 33 of SEQ ID NO:24.

8. The polypeptide of claim 1 comprising SEQ ID NO:24.

9. The polypeptide of claim 1 comprising SEQ ID NO:24 with from one to five conservatively substituted amino acid residues.

10. The polypeptide of claim 1 comprising SEQ ID NO:24 with an addition of one to five amino acid residues.

11. The polypeptide of claim 1 comprising SEQ ID NO:24 with a deletion of one to five amino acid residues.

12. The polypeptide of claim 1 comprising an amino acid sequence having a lysine at amino acid position 33 of SEQ ID NO:2.

13. The polypeptide of claim 1 comprising SEQ ID NO:2.

14. The polypeptide of claim 1 comprising SEQ ID NO:2 with an addition or deletion of one to five amino acid residues.

15. The polypeptide of claim 1 comprising SEQ ID NO:2 with from one to five conservatively substituted amino acid residues.

16. Isolated native sequence human fused polypeptide encoded by the cDNA insert of the nucleic acid deposited under accession number ATCC 209637.

17. A polypeptide encoded by the cDNA insert of ATCC Deposit No. 209637 with one to five conservatively substituted amino acid residue.

18. A polypeptide encoded by the cDNA insert of ATCC Deposit No. 209637 with an addition or deletion of one to five amino acid residues.

19. A polypeptide encoded by the cDNA insert of ATCC Deposit No. 209637.

* * * * *